United States Patent
Liu et al.

(10) Patent No.: US 10,472,315 B2
(45) Date of Patent: Nov. 12, 2019

(54) INHIBITORS OF METHIONINE AMINOPEPTIDASES AND METHODS OF TREATING DISORDERS

(75) Inventors: Jun O. Liu, Clarksville, MD (US); Omonike Arike Olaleye, Houston, TX (US); Shridhar Bhat, Cockeysville, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 13/388,941

(22) PCT Filed: Aug. 5, 2010

(86) PCT No.: PCT/US2010/044547
§ 371 (c)(1),
(2), (4) Date: Feb. 3, 2012

(87) PCT Pub. No.: WO2011/017519
PCT Pub. Date: Feb. 10, 2011

(65) Prior Publication Data
US 2012/0196852 A1    Aug. 2, 2012

Related U.S. Application Data

(60) Provisional application No. 61/231,516, filed on Aug. 5, 2009.

(51) Int. Cl.
| | | |
|---|---|---|
| *C07C 50/12* | (2006.01) | |
| *C07D 277/42* | (2006.01) | |
| *C07D 277/44* | (2006.01) | |
| *C07D 277/46* | (2006.01) | |
| *C07D 277/84* | (2006.01) | |
| *C07D 295/116* | (2006.01) | |
| *C07D 513/04* | (2006.01) | |

(52) U.S. Cl.
CPC ............ *C07C 50/12* (2013.01); *C07D 277/42* (2013.01); *C07D 277/44* (2013.01); *C07D 277/46* (2013.01); *C07D 277/84* (2013.01); *C07D 295/116* (2013.01); *C07D 513/04* (2013.01)

(58) Field of Classification Search
CPC .. A61K 31/425; C07D 277/60; C07D 277/42; C07D 277/44; C07D 277/46; C07D 277/84; C07D 295/116; C07D 513/04; C07C 50/12

USPC ......... 544/106; 548/150, 149, 151; 514/366, 514/229.5, 239.5, 312, 319, 617, 657, 681
See application file for complete search history.

(56) References Cited

U.S. PATENT DOCUMENTS

| | | | | |
|---|---|---|---|---|
| 3,021,216 A | * | 2/1962 | Rosenthal ............ | A23K 20/132 426/72 |
| 8,729,097 B2 | * | 5/2014 | Liu ........................ | A61K 31/47 514/312 |
| 2010/0063008 A1 | * | 3/2010 | Matteliano ........... | A61K 9/0014 514/159 |
| 2015/0141415 A1 | * | 5/2015 | Olaleye ................ | C07D 498/04 514/229.8 |

FOREIGN PATENT DOCUMENTS

| | | | | |
|---|---|---|---|---|
| JP | 58-184948 | * | 10/1983 | |
| JP | 58184948 A | | 10/1983 | |
| WO | WO-2009140215 A2 | * | 11/2009 | ............. A61K 31/47 |

OTHER PUBLICATIONS

Goblyos et al., Bioorg. Med. Chem. 13 (2005) 1079-1087.*
Ramalingam et al., Journal of Medicinal Chemistry, 1977, vol. 20, No. 5.*
STN/CAS results, Gross et al, WO 2006082588, (2006).*
Hashem et al., Journal of Medicinial Chemistry 1976, vol. 19, No. 2, pp. 229-239.*
Olaleye et al., "Characterization of clioquinol and analogues as novel inhibitors of methionine aminopeptidases from *Mycobacterium tuberculosis*", 2011, Tuberculosis, 91(1), pp. S61-S65. (Year: 2011).*
Bhat et al., "Analogs of N0-hydroxy-N-(4H,5H-naphtho[1,2-d]thiazol-2-yl)methanimidamide inhibit *Mycobacterium tuberculosis* methionine aminopeptidases", 2012, Bioorganic & Medicinal Chemistry, 20(14), pp. 4507-4513. (Year: 2012).*
Bakunina et al., "Effect of 5-Hydroxy- and 5,8-Dihydroxy-1,4-Naphthoquinones on the Hydrolytic Activity of a-Galactosidase", Chemistry of Natural Compounds, vol. 45, No. 1, pp. 69-73 (2009).

* cited by examiner

*Primary Examiner* — My-Chau T. Tran
(74) *Attorney, Agent, or Firm* — John Hopkins Technology Ventures

(57) ABSTRACT

The invention is directed towards novel naphthoquinone and naphthothiazole compounds, and methods of treating disorders related to MetAP, including tuberculosis and bacterial infection, using various naphthoquinone, hydroxyquinonline, and naphthothiazole compounds.

5 Claims, 9 Drawing Sheets
Specification includes a Sequence Listing.

```
MtMetAP1c   --------------------MPSRTALSPGVLS----------------------------  13
HsMetAP1    MAAVETRVCETDGCSSEAKLQCPTCIKLGIQGSYFCSQECFKGSWATHKLLHKKAKDEKA 60
MtMetAP1a   ------------------------------------------------------------
EcMetAP1    ------------------------------------------------------------

MtMetAP1c   -------------------------------------PTRPVPNWIARPEYVGKPAAQEGSEP  39
HsMetAP1    KREVSSWTVEGDINTDPWAGYRYTGKLRPHYPLMPTRPVPSYIQRPDYADHPLGMSESEQ 120
MtMetAP1a   ----------------------------------MRPLARLRGRRVVPQR---------  16
EcMetAP1    ---------------------------------------------MIICK---------   5

MtMetAP1c   WVQ---------TPEVIEKMRVAGRIAAGALAEAGKAVAPGVTTDELDRIAHEYLVDNGAY  91
HsMetAP1    ALKGTSQIKLLSSEDIEGMRLVCRLAREVLDVAAGMIKPGVTTEEIDHAVHLACIARNCY 180
MtMetAP1a   -----------SAGELDAMAAAGAVVAAALRAIRAAAAPGTSSLSLDEIAESVIRESGAT  65
EcMetAP1    -----------TPRELGIMREAGRIVALTHEELKKHIKPGISTKELDQIAERFIKKQGAI  54

MtMetAP1c   PSTLGYKGFPKSCCTSLNEVICHGIPD-STVITDGDIVNIDVTAYIGGVHGDTNATFPAG 150
HsMetAP1    PSPLNYYNFPKSCCTSVNEVICHGIPD-RRPLQEGDIVNVDITLYRNGYHGDLNETFFVG 239
MtMetAP1a   PSFLGYHGYPASICASINDRVVHGIPSTAEVLAPGDLVSIDCGAVLDGWHGDAAITFGVG 125
EcMetAP1    PSFKGYNGFRGSICVSVNEELVHGIPG-SRVLKDGDIISIDIGAKLNGYHGDSAWTYPVG 113
                                                 *            *

MtMetAP1c   DVADEHRLLVDRTREATMRAINTVKPGRALSVIGRVIESYANRFG------YNVVRDFTG 204
HsMetAP1    EVDDGARKLVQTTYECLMQAIDAVKPGVRYRELGNIIQKHAQANG------FSVVRSYCG 293
MtMetAP1a   ALSDADEALSEATRESLQAGIAAMVVGNRLTDVAHAIETGTRAAELRYGRSFGIVAGYGG 185
EcMetAP1    NISDDDKKLLEVTEESLYKGLQEAKPGERLSNISHAIQTYVENEQ------FSVVREYVG 167

MtMetAP1c   HGIGTTFHNGLVVLHYDQPAVETIMQPGMTFTIEPMINLGALDYEIWDDGWTVVTKDRKW 264
HsMetAP1    HGIHKLFHTAPNVPHYAKNKAVGVMKSGHVFTIEPMICEGGWQDETWPDGWTAVTRDGKR 353
MtMetAP1a   HGIGRQMHMDPFLPNEGAPGRGPLLAAGSVLAIEPMLTLGTTKTVVLDDKWTVTTADGSR 245
EcMetAP1    HGVGQDLHEDPQIPHYGPPNKGPRLKPGMVLAIEPMVNAGSRYVKTLADNWTVVTVDGKK 227
            *                              *

MtMetAP1c   TAQFEHTLLVTDTGVEILTCL------------ 285
HsMetAP1    SAQFEHTLLVTDTGCEILTRRLDSARPHFMSQF 386
MtMetAP1a   AAHWEHTVAVTDDGPRILTLG------------ 266
EcMetAP1    CAHFEHTIAITETGFDILTRV------------ 248
               *
```

Figure 1

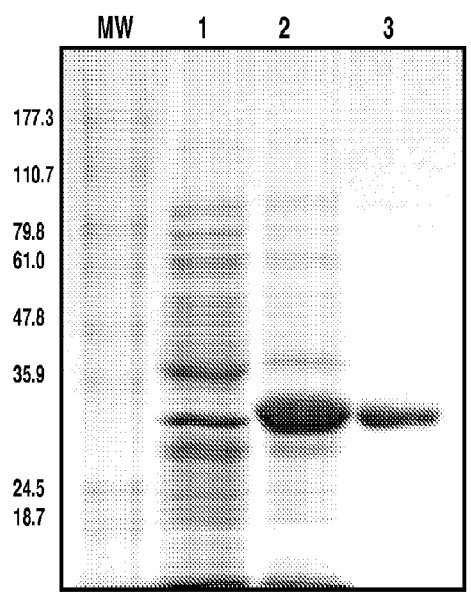
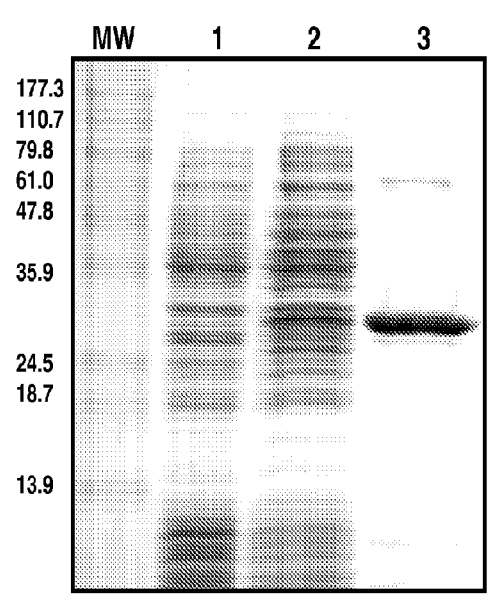
Figure 2

A i.
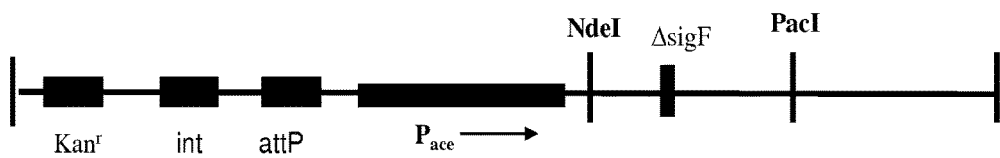
A ii.
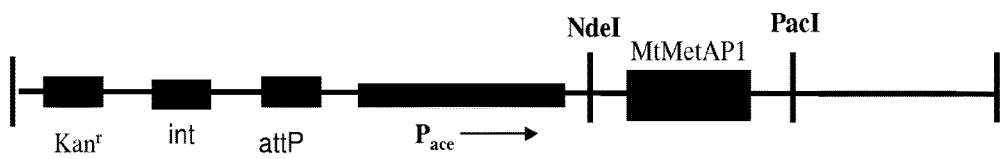
A iii.
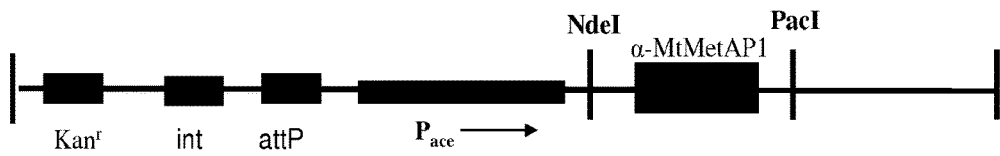
Figure 3

B.
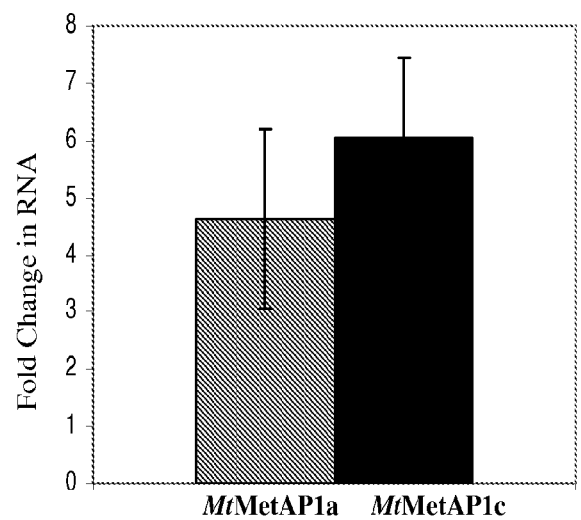
C.
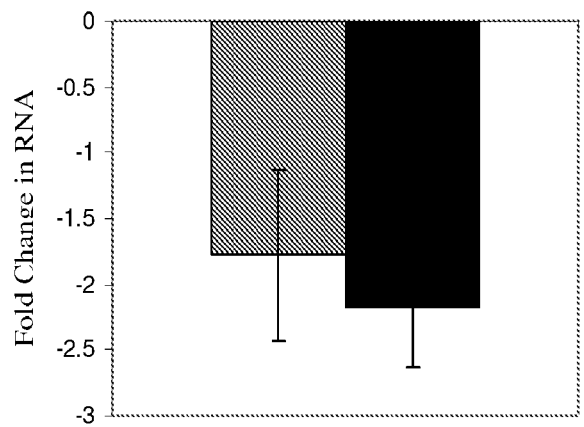
Figure 3 (cont.)

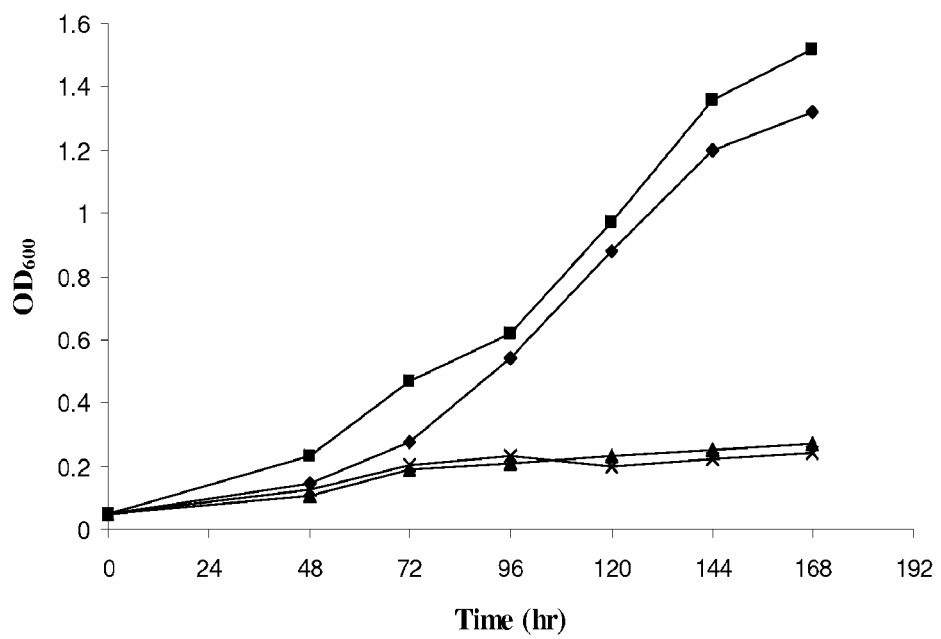
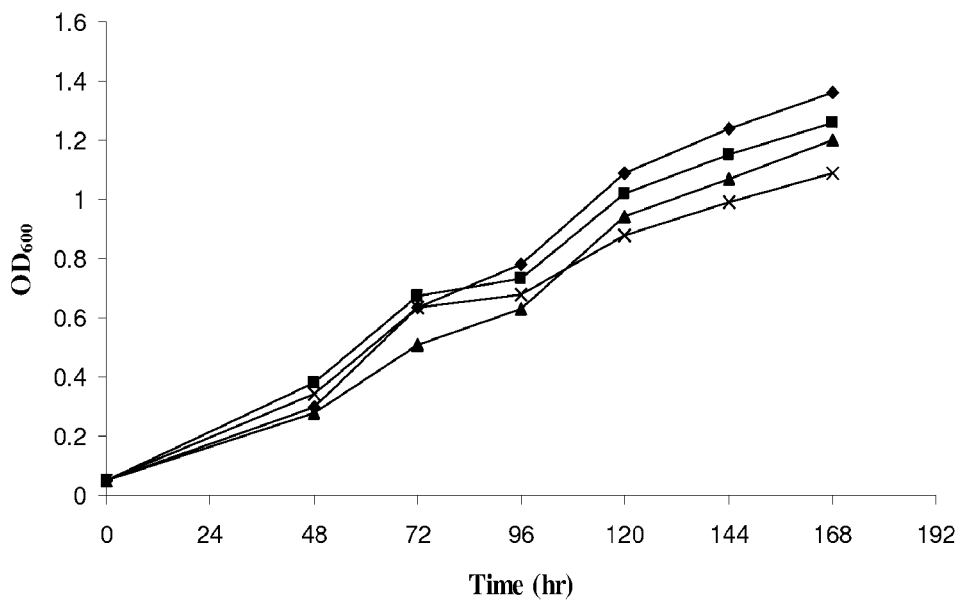
Figure 4.

MtMetAP Inhibitors

| Entry | Structure | Substituent(s) | CAS # | IC$_{50}$ (μM) MtMetAP1a | IC$_{50}$ (μM) MtMetAP1c | Other Data |
|---|---|---|---|---|---|---|
| 37 | 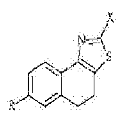 | R=H; X=NH$_2$·HBr | 40353-70-6 | ND | > 10 | |
| 38 | | R=OMe; X=NH$_2$·HBr | 376348-30-3 | ND | > 10 | |
| 39 | | R=OMe; X=NHCOMe | 300664-42-0 | ND | > 10 | |
| 40 | | R=OMe; X=NHCO(CH$_2$)$_2$Me | 300541-89-3 | ND | > 10 | |
| 41 | | R=H; X=NHCO(CH$_2$)$_2$Me | 300541-94-0 | ND | > 10 | |
| 42 | | R=OMe; X=NHCO-(S)-CH(OH)Me | new | >50 | > 10 | BaMetAP1: > 250 μM |
| 43 | | R=OMe; X=NHCH$_2$(2-furyl) | new | >50 | > 50 | |
| 44 | | R=H; X= N=CHNMe$_2$ | 300541-99-5 | | > 10 | |
| 45 | | R=OMe; X= N=CH(2-furyl) | 344895-73-4 | >50 | > 50 | |
| 46 | | R=OMe; X= N=CH(2-hydroxyphenyl) | 344895-84-7 | >50 | > 50 | |
| 47 | 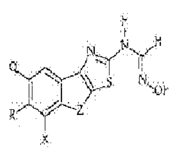 | Q,R,X=H; Z=(CH$_2$)$_2$ | 300664-34-0 | 7.03 | 0.36 | hMetAP1 & 2: >30 μM; MIC (μg/mL): TB, 50.0 |
| 48 | | Q,X=H; R=OMe; Z=(CH$_2$)$_2$ | 300664-33-9 | 34.68 | 0.30 | hMetAP1 & 2: >30 μM; BaMetAP1: 15.05 μM; MIC (μg/mL): TB, 25.0; Ef, 32 |
| 49 | | Q=OMe; R,X=H; Z=(CH$_2$)$_2$ | new | 24.59 | 0.82 | BaMetAP1: 16.98 μM |
| 50 | | Q,R=H; X=OMe; Z=(CH$_2$)$_2$ | new | ND | 0.51 | |
| 51 | | Q,R=OMe; X=H; Z=(CH$_2$)$_2$ | new | ND | 0.36 | |
| 52 | | Q-R=OCH$_2$O; X=H; Z=(CH$_2$)$_2$ | new | ND | | |
| 53 | | Q-R=OCH$_2$O; X=H; Z=OCH$_2$ | new | 1.77 | 0.13 | |
| 54 | | Q,X=H; R=OMe; Z=OCH$_2$ | new | >50 | 2.28 | |
| 55 | | Q,X=H; R=OMe; Z=OCH(Ph) | new | >50 | >25 | |
| 56 | | Q,X=H; R=OMe; Z=CH$_2$ | new | >50 | > 25 | |
| 57 | | Q-R=OCH$_2$O; X=H; Z=(CH$_2$)$_3$ | new | 0.95 | 0.80 | |
| 58 | | Q-R=OCH$_2$O; X=H; Z=O(CH$_2$)$_3$ | new | 0.76 | 0.06 | |
| 59 | | | | new | >50 | > 10 | |

Figure 6.

MtMetAP Inhibitors

| Entry | Structure Substituent(s) | CAS # | IC$_{50}$ (µM) Co$^{2+}$-MtMetAP1a | IC$_{50}$ (µM) Co$^{2+}$-MtMetAP1c | IC$_{50}$ (µM) Mn$^{2+}$-MtMetAP1c | Other Data |
|---|---|---|---|---|---|---|
| 60 | X=Cl; Y=Z= -CH$_2$N(cyclohexyl)CH$_2$- | 379253-06-2 | 4.20 | 3.76 | 23.83 | |
| 61 | X=Cl; Y=CH$_2$N(CH$_2$CH$_2$)$_2$O; Z=H | 6596-37-2 | ND | ND | ND | |
| 62 | X=Cl; Y=CH$_2$N(CH$_2$CH$_2$)$_2$NCH$_3$; Z=H | 92556-96-2 | ND | ND | ND | |
| 63 | X=Cl; Y=CH(Ph)N(CH$_2$CH$_2$)$_2$O; Z=H | 1221161-34-7 | ND | ND | ND | |
| 64 | X=Cl; Y=H; Z=CH$_2$CH$_2$OH | 82488-72-0 | ND | ND | ND | |
| 65 | X=Cl; Y=H; Z=OCONHPh | 99541-05-6 | ND | ND | ND | |
| 66 | X,Y=Cl; Z=COCH$_3$ | 52174-94-4 | 4.87 | 4.92 | 36.40 | |
| 67 | X,Y=Br; Z=H | 521-74-4 | ND | ND | ND | |
| 68 | X,Y=I; Z=H | 83-73-8 | ND | ND | ND | |
| 69 | X=Cl; Y=Br; Z=H | 7640-33-7 | 5.44 | 4.92 | 63.60 | hMetAP1/2: 105.3/112.2 µM; MIC (µg/mL): TB, 5.0; dormant-TB, 0.65–1.62 |
| 70 | X=Cl; Y=I; Z=H | 130-26-7 | 9.25 | 11.16 | 75.28 | hMetAP1/2: 84.7/80.4 µM; MIC (µg/mL): TB, 10.0 |

Figure 7.

```
                        SEQUENCE LISTING

<160> NUMBER OF SEQ ID NOS: 16

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gcgggatccc ctagtcgtac cgcgctc                                           27

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gcgctcgagc tacagacagg tcaggatc                                          28

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gcgccatggg cccactggca cggctgcggg gtc                                    33

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gcgctcgaga ccgagcgtca gaattcgggg ccc                                    33

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cgcattaatg cccactggca cggctgcggg gtc                                    33

<210> SEQ ID NO 6
```

```
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ccttaattaa ctaaccgagc gtcagaattc ggggc                              35

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggaattccat atgcctagtc gtaccgcgc                                     29

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ccttaattaa ctacagacag gtcaggatc                                     29

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ccgaggtgct cgcgcccggt g                                             21

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ttcgatggca tgcgcgacg                                                19

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gctgggctac aagggattcc cgaag                                         25

<210> SEQ ID NO 12
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tccggtcaac gagcaaccgg tg                                                    22

<210> SEQ ID NO 13
<211> LENGTH: 285
<212> TYPE: PRT
<213> ORGANISM: Mycobacterium tuberculosis

<400> SEQUENCE: 13
```

Met Pro Ser Arg Thr Ala Leu Ser Pro Gly Val Leu Ser Pro Thr Arg
1               5                   10                  15

Pro Val Pro Asn Trp Ile Ala Arg Pro Glu Tyr Val Gly Lys Pro Ala
            20                  25                  30

Ala Gln Glu Gly Ser Glu Pro Trp Val Gln Thr Pro Glu Val Ile Glu
        35                  40                  45

Lys Met Arg Val Ala Gly Arg Ile Ala Ala Gly Ala Leu Ala Glu Ala
50                  55                  60

Gly Lys Ala Val Ala Pro Gly Val Thr Thr Asp Glu Leu Asp Arg Ile
65                  70                  75                  80

Ala His Glu Tyr Leu Val Asp Asn Gly Ala Tyr Pro Ser Thr Leu Gly
                85                  90                  95

Tyr Lys Gly Phe Pro Lys Ser Cys Cys Thr Ser Leu Asn Glu Val Ile
            100                 105                 110

Cys His Gly Ile Pro Asp Ser Thr Val Ile Thr Asp Gly Asp Ile Val
        115                 120                 125

Asn Ile Asp Val Thr Ala Tyr Ile Gly Gly Val His Gly Asp Thr Asn
130                 135                 140

Ala Thr Phe Pro Ala Gly Asp Val Ala Asp Glu His Arg Leu Leu Val
145                 150                 155                 160

Asp Arg Thr Arg Glu Ala Thr Met Arg Ala Ile Asn Thr Val Lys Pro
                165                 170                 175

Gly Arg Ala Leu Ser Val Ile Gly Arg Val Ile Glu Ser Tyr Ala Asn
            180                 185                 190

Arg Phe Gly Tyr Asn Val Val Arg Asp Phe Thr Gly His Gly Ile Gly
        195                 200                 205

Thr Thr Phe His Asn Gly Leu Val Val Leu His Tyr Asp Gln Pro Ala
210                 215                 220

Val Glu Thr Ile Met Gln Pro Gly Met Thr Phe Thr Ile Glu Pro Met
225                 230                 235                 240

Ile Asn Leu Gly Ala Leu Asp Tyr Glu Ile Trp Asp Asp Gly Trp Thr
                245                 250                 255

Val Val Thr Lys Asp Arg Lys Trp Thr Ala Gln Phe Glu His Thr Leu
            260                 265                 270

Leu Val Thr Asp Thr Gly Val Glu Ile Leu Thr Cys Leu
        275                 280                 285

```
<210> SEQ ID NO 14
<211> LENGTH: 386
<212> TYPE: PRT
<213> ORGANISM: Homo sapiens

<400> SEQUENCE: 14
```

```
Met Ala Ala Val Glu Thr Arg Val Cys Glu Thr Asp Gly Cys Ser Ser
1               5                   10                  15

Glu Ala Lys Leu Gln Cys Pro Thr Cys Ile Lys Leu Gly Ile Gln Gly
            20                  25                  30

Ser Tyr Phe Cys Ser Gln Glu Cys Phe Lys Gly Ser Trp Ala Thr His
        35                  40                  45

Lys Leu Leu His Lys Lys Ala Lys Asp Glu Lys Ala Lys Arg Glu Val
    50                  55                  60

Ser Ser Trp Thr Val Glu Gly Asp Ile Asn Thr Asp Pro Trp Ala Gly
65                  70                  75                  80

Tyr Arg Tyr Thr Gly Lys Leu Arg Pro His Tyr Pro Leu Met Pro Thr
                85                  90                  95

Arg Pro Val Pro Ser Tyr Ile Gln Arg Pro Asp Tyr Ala Asp His Pro
            100                 105                 110

Leu Gly Met Ser Glu Ser Glu Gln Ala Leu Lys Gly Thr Ser Gln Ile
        115                 120                 125

Lys Leu Leu Ser Ser Glu Asp Ile Glu Gly Met Arg Leu Val Cys Arg
    130                 135                 140

Leu Ala Arg Glu Val Leu Asp Val Ala Ala Gly Met Ile Lys Pro Gly
145                 150                 155                 160

Val Thr Thr Glu Glu Ile Asp His Ala Val His Leu Ala Cys Ile Ala
                165                 170                 175

Arg Asn Cys Tyr Pro Ser Pro Leu Asn Tyr Tyr Asn Phe Pro Lys Ser
            180                 185                 190

Cys Cys Thr Ser Val Asn Glu Val Ile Cys His Gly Ile Pro Asp Arg
        195                 200                 205

Arg Pro Leu Gln Glu Gly Asp Ile Val Asn Val Asp Ile Thr Leu Tyr
    210                 215                 220

Arg Asn Gly Tyr His Gly Asp Leu Asn Glu Thr Phe Phe Val Gly Glu
225                 230                 235                 240

Val Asp Asp Gly Ala Arg Lys Leu Val Gln Thr Thr Tyr Glu Cys Leu
                245                 250                 255

Met Gln Ala Ile Asp Ala Val Lys Pro Gly Val Arg Tyr Arg Glu Leu
            260                 265                 270

Gly Asn Ile Ile Gln Lys His Ala Gln Ala Asn Gly Phe Ser Val Val
        275                 280                 285

Arg Ser Tyr Cys Gly His Gly Ile His Lys Leu Phe His Thr Ala Pro
    290                 295                 300

Asn Val Pro His Tyr Ala Lys Asn Lys Ala Val Gly Val Met Lys Ser
305                 310                 315                 320

Gly His Val Phe Thr Ile Glu Pro Met Ile Cys Glu Gly Gly Trp Gln
                325                 330                 335

Asp Glu Thr Trp Pro Asp Gly Trp Thr Ala Val Thr Arg Asp Gly Lys
            340                 345                 350

Arg Ser Ala Gln Phe Glu His Thr Leu Leu Val Thr Asp Thr Gly Cys
        355                 360                 365

Glu Ile Leu Thr Arg Arg Leu Asp Ser Ala Arg Pro His Phe Met Ser
    370                 375                 380

Gln Phe
385

<210> SEQ ID NO 15
<211> LENGTH: 266
```

<212> TYPE: PRT
<213> ORGANISM: Mycobacterium tuberculosis

<400> SEQUENCE: 15

Met Arg Pro Leu Ala Arg Leu Arg Gly Arg Arg Val Val Pro Gln Arg
1               5                   10                  15

Ser Ala Gly Glu Leu Asp Ala Met Ala Ala Gly Ala Val Val Ala
            20                  25                  30

Ala Ala Leu Arg Ala Ile Arg Ala Ala Ala Pro Gly Thr Ser Ser
        35                  40                  45

Leu Ser Leu Asp Glu Ile Ala Glu Ser Val Ile Arg Glu Ser Gly Ala
    50                  55                  60

Thr Pro Ser Phe Leu Gly Tyr His Gly Tyr Pro Ala Ser Ile Cys Ala
65                  70                  75                  80

Ser Ile Asn Asp Arg Val Val His Gly Ile Pro Ser Thr Ala Glu Val
                85                  90                  95

Leu Ala Pro Gly Asp Leu Val Ser Ile Asp Cys Gly Ala Val Leu Asp
            100                 105                 110

Gly Trp His Gly Asp Ala Ala Ile Thr Phe Gly Val Gly Ala Leu Ser
        115                 120                 125

Asp Ala Asp Glu Ala Leu Ser Glu Ala Thr Arg Glu Ser Leu Gln Ala
    130                 135                 140

Gly Ile Ala Ala Met Val Val Gly Asn Arg Leu Thr Asp Val Ala His
145                 150                 155                 160

Ala Ile Glu Thr Gly Thr Arg Ala Ala Glu Leu Arg Tyr Gly Arg Ser
                165                 170                 175

Phe Gly Ile Val Ala Gly Tyr Gly Gly His Gly Ile Gly Arg Gln Met
            180                 185                 190

His Met Asp Pro Phe Leu Pro Asn Glu Gly Ala Pro Gly Arg Gly Pro
        195                 200                 205

Leu Leu Ala Ala Gly Ser Val Leu Ala Ile Glu Pro Met Leu Thr Leu
    210                 215                 220

Gly Thr Thr Lys Thr Val Val Leu Asp Asp Lys Trp Thr Val Thr Thr
225                 230                 235                 240

Ala Asp Gly Ser Arg Ala Ala His Trp Glu His Thr Val Ala Val Thr
                245                 250                 255

Asp Asp Gly Pro Arg Ile Leu Thr Leu Gly
            260                 265

<210> SEQ ID NO 16
<211> LENGTH: 248
<212> TYPE: PRT
<213> ORGANISM: Escherichia coli

<400> SEQUENCE: 16

Met Ile Ile Cys Lys Thr Pro Arg Glu Leu Gly Ile Met Arg Glu Ala
1               5                   10                  15

Gly Arg Ile Val Ala Leu Thr His Glu Glu Leu Lys Lys His Ile Lys
            20                  25                  30

Pro Gly Ile Ser Thr Lys Glu Leu Asp Gln Ile Ala Glu Arg Phe Ile
        35                  40                  45

Lys Lys Gln Gly Ala Ile Pro Ser Phe Lys Gly Tyr Asn Gly Phe Arg
    50                  55                  60

Gly Ser Ile Cys Val Ser Val Asn Glu Glu Leu Val His Gly Ile Pro
65                  70                  75                  80

```
Gly Ser Arg Val Leu Lys Asp Gly Asp Ile Ile Ser Ile Asp Ile Gly
                85              90              95

Ala Lys Leu Asn Gly Tyr His Gly Asp Ser Ala Trp Thr Tyr Pro Val
            100             105             110

Gly Asn Ile Ser Asp Asp Asp Lys Lys Leu Leu Glu Val Thr Glu Glu
            115             120             125

Ser Leu Tyr Lys Gly Leu Gln Glu Ala Lys Pro Gly Glu Arg Leu Ser
    130             135             140

Asn Ile Ser His Ala Ile Gln Thr Tyr Val Glu Asn Glu Gln Phe Ser
145             150             155             160

Val Val Arg Glu Tyr Val Gly His Gly Val Gly Gln Asp Leu His Glu
                165             170             175

Asp Pro Gln Ile Pro His Tyr Gly Pro Pro Asn Lys Gly Pro Arg Leu
            180             185             190

Lys Pro Gly Met Val Leu Ala Ile Glu Pro Met Val Asn Ala Gly Ser
            195             200             205

Arg Tyr Val Lys Thr Leu Ala Asp Asn Trp Thr Val Val Thr Val Asp
    210             215             220

Gly Lys Lys Cys Ala His Phe Glu His Thr Ile Ala Ile Thr Glu Thr
225             230             235             240

Gly Phe Asp Ile Leu Thr Arg Val
                245
```

INHIBITORS OF METHIONINE AMINOPEPTIDASES AND METHODS OF TREATING DISORDERS

RELATED APPLICATIONS

The present application is a 35 U.S.C. § 371 U.S. national entry of International Application PCT/US2010/044547 (WO 2011/017519) having an International filing date of Aug. 5, 2010 which claims the benefit of U.S. Provisional application No. 61/231,516, filed on Aug. 5, 2009. The entire contents of the aforementioned applications are incorporated herein by reference.

TECHNICAL FIELD

The present invention relates to novel and known inhibitors of methionine aminopeptidases (MetAPs), and methods of treating disorders, including tuberculosis and as antibacterial agents.

BACKGROUND OF THE INVENTION

*Mycobacterium tuberculosis*, the etiological agent of tuberculosis, is one of the oldest pathogens that have impacted humans globally and the re-emergence of *M. tuberculosis* has become a primary public health burden (National Institute of Allergy and Infectious Diseases, Tuberculosis Health Matters 2002. Fact sheets and brochure; Raviglione, M. C., 2003, Tuberculosis 83:4-14; World Health Organization. 2005. WHO declares TB an emergency in Africa: Call for "urgent and extraordinary actions" to halt worsening epidemic. WHO Media centre News). The rise in multi-drug resistant and extensively drug-resistant strains of *M. tuberculosis* has reduced the impact of current treatment options (Cole, S. T. et al. 1998. *Nature* 393:537-544; Fauci, A. S., 2008. Perspective JID 197:1493-1498; Zhang, Y. 2005. *Annu. Rev. Pharmacol. Toxicol.* 45:529-564). Therefore, the development of antibiotics with novel mechanisms of action that will be effective for short term therapy is essential to effectively treat patients with tuberculosis (TB).

Methionine Aminopeptidase (MetAP) is a dinuclear metalloprotease that removes the N-terminal methionine from polypeptides and proteins (Giglione, C., A. Boularot, and T. Meinnel. 2004. *Cell. Mol. Life. Sci.* 61:1455-1474; Lowther, W. T., and B. W. Matthews. 2000. *Bioch Biophys. Acta.* 1477:157-167). MetAP is conserved in all microbial genomes that have been sequenced to date. There are two classes of MetAPs, MetAP1 and MetAP2 that differ in the presence of an internal polypeptide insertion present within the catalytic domain of MetAP2 (Addlagatta, A., et al. 2005. *Biochemistry* 44:14741-14749; Arfin, S. M., et al. 1995. *Proc. Natl. Acad. Sci.* 92:7714-7718; Liu, S., et al. 1998. *Science* 282:1324-1327). Eukaryotes possess both classes while prokaryotes have homologs of either MetAP1 (eubacteria) or MetAP2 (archeabacteria) (Lowther, W. T., and B. W. Matthews. 2000. *Biochim. Biophys. Acta.* 1477:157-167). Variants of MetAP1 are further classified as MetAP1a, MetAP1b and MetAP1c (Addlagatta, et al. 2005. *Biochemistry* 44:7166-7174), which are distinguished by the existence of an N-terminal extension in MetAP1b and MetAP1c, and a unique zinc finger domain in MetAP1b. Recently, the X-ray crystal structures of the apo- and methionine-bound forms of *M. tuberculosis* MetAP1c were solved (Addlagatta, et al. 2005. *Biochemistry* 44:7166-7174). The X-ray structure revealed the existence of a highly conserved proline rich N-terminal extension in MtMetAP1c which is absent in MtMetAP1a but has sequence homology with the linker region of human MetAP1 (HsMetAP1).

Genetic studies have shown that deletion of MetAP from *Escherichia coli* and *Salmonella typhimurium* is lethal (Chang, S. Y., E. C. McGary, and S. Chang. 1989. *J. Bacteriol.* 171:4071-4072; Miller, C. G., J. L. Kukral, and N. R. Movva. 1989. *J. Bacteriol.* 171:5215-5217). In yeast, deletion of either ScMetAP1 or ScMetAP2 results in a slow-growth phenotype, while disruption of both genes is lethal. In *Caenorhabditis elegans*, MetAP2 is essential for germ cell development. In mammalian cells both HsMetAP1 and HsMetAP2 have been shown to be required for cell proliferation. Moreover, HsMetAP2 is essential for endothelial cell growth and angiogenesis. Recent studies from our lab have also shown that HsMetAP1 is involved in G(2)/M phase of the cell cycle.

The essential role of MetAPs in prokaryotes makes this enzyme an attractive target for the development of new antibiotics. In prokaryotes, where protein synthesis begins with an N-formylated methionine, peptide deformylase (PDF) catalyzes the removal of the formyl group before MetAP activity (Giglione, C., et al. 2003. *EMBO J.* 22:13-23; Solbiati, J., et al. 1999. *J. Mol. Biol.* 290:607-614). Unlike most other prokaryotes, *M. tuberculosis* possesses two MetAPs: MtMetAP1a and MtMetAP1c. They share about 33% sequence identity. Both MtMetAPs have less than 45% similarity to *E. coli* MetAP1 (EcMetAP1), less than 48% similarity to human MetAP1 (hMetAP1) and less than 30% similarity to human MetAP2 (hMetAP2). Given the presence of the two MetAP genes in *M. tuberculosis*, it was unclear whether inhibition of either or both MtMetAPs is sufficient to inhibit bacterial growth.

SUMMARY OF THE INVENTION

In one aspect, the invention provides a compound of formula I-B:

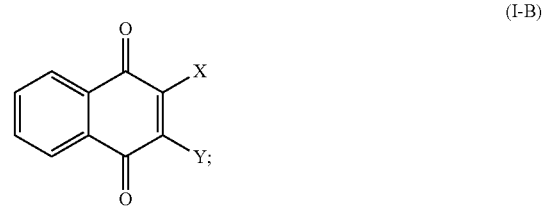

(I-B)

or a pharmaceutically acceptable salt thereof, wherein,

X is halo, an optionally substituted aryloxy, an optionally substituted aryl, an optionally substituted heteroaryl, C(O)OR$_B$, C(O)R$_A$, OR$_B$, NR$_A$R$_B$, NR$_A$C(O)R$_A$, or SO$_3$R$_A$;

Y is halo, an optionally substituted aryloxy, an optionally substituted aryl, an optionally substituted heteroaryl, optionally substituted heterocycloalkyl, C(O)OR$_A$, C(O)R$_A$, OR$_A$, NR$_A$R$_A$, NR$_A$C(O)R$_A$, or SO$_3$R$_A$;

each R$_A$ is independently H, OH, halo, an optionally substituted alkyl, or an optionally substituted aryl; and each R$_B$ is independently H, optionally substituted alkyl, optionally substituted aralkyl, or optionally substituted aryl.

In another aspect, the invention provides a compound of formula II:

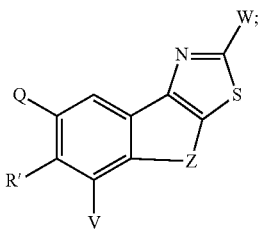

or a pharmaceutically acceptable salt thereof,
wherein,

Z is absent, $(CR_BR_C)_m$, $O(CR_BR_C)_m$, or $NR_D(CR_BR_C)_m$;

W is $NR_DR_D$, $NR_DC(O)R_D$, $N=C(R_E)$alkyl, $N=C(R_E)$aryl, $N=C(R_E)$heteroaryl, $N=C(R_E)$aralkyl, or $NR_DCR_B=N-OH$;

R' is H, $OR_B$, or $NR_AR_B$;

Q is H, $C(O)OR_B$, $C(O)R_A$, $OR_B$, $NR_AR_B$, $NR_AC(O)R_A$, or $SO_3R_A$; or

R' and Q, together with the atoms to which each is attached, forms a heterocycloalkyl, or heteroaryl, each of which is optionally substituted;

V is H, $C(O)OR_B$, $C(O)R_A$, $OR_B$, $NR_AR_B$, $NR_AC(O)R_A$, or $SO_3R_A$;

each m is independently 1, 2, or 3;

each $R_B$ is independently H, optionally substituted alkyl, optionally substituted aralkyl, or optionally substituted aryl;

each $R_C$ is independently H, optionally substituted alkyl, optionally substituted aralkyl, or optionally substituted aryl;

each $R_D$ is independently H, optionally substituted alkyl, optionally substituted aralkyl, optionally substituted heteroaralkyl, or optionally substituted aryl;

each $R_E$ is independently H, optionally substituted alkyl, optionally substituted aralkyl, optionally substituted heteroaralkyl, or optionally substituted aryl; and each $R_A$ is independently H, OH, halo, an optionally substituted alkyl, or an optionally substituted aryl.

In another aspect, the invention provides a pharmaceutical composition comprising a therapeutically effective amount of a compound described herein, or an embodiment or example described herein, or a pharmaceutically acceptable salt, ester, or prodrug thereof, in combination with a pharmaceutically acceptable carrier or excipient.

In one aspect, the invention provides a method of treating a disease or disorder associated with methionine aminopeptidase (MetAP) in a subject, the method comprising the step of administering to the subject an effective amount of a compound of formula I:

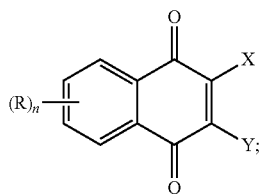

or a pharmaceutically acceptable salt thereof,
wherein,

R is H, hydroxy, nitro, halo, an optionally substituted alkyl, an optionally substituted cycloalkyl, an optionally substituted alkenyl, an optionally substituted aryl, an optionally substituted heteroaryl, optionally substituted heterocycloalkyl, $OR_B$, or $NR_AR_B$;

X is H, halo, nitro, halo, hydroxy, an optionally substituted alkyl, an optionally substituted cycloalkyl, an optionally substituted aryloxy, an optionally substituted alkenyl, an optionally substituted aryl, an optionally substituted heteroaryl, optionally substituted heterocycloalkyl, $C(O)OR_B$, $C(O)R_A$, $OR_B$, $NR_AR_B$, $NR_AC(O)R_A$, or $SO_3R_A$;

Y is H, halo, nitro, halo, hydroxy, an optionally substituted alkyl, an optionally substituted cycloalkyl, an optionally substituted aryloxy, an optionally substituted alkenyl, an optionally substituted aryl, an optionally substituted heteroaryl, optionally substituted heterocycloalkyl, $C(O)OR_B$, $C(O)R_A$, $OR_B$, $NR_AR_B$, $NR_AC(O)R_A$, or $SO_3R_A$;

each $R_A$ is independently H, OH, halo, an optionally substituted alkyl, or an optionally substituted aryl;

each $R_B$ is independently H, optionally substituted alkyl, optionally substituted aralkyl, or optionally substituted aryl; and n is 1, 2, or 3;

formula II:

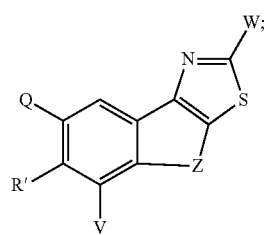

or a pharmaceutically acceptable salt thereof,
wherein,

Z is absent, $(CR_BR_C)_m$, $O(CR_BR_C)_m$, or $NR_D(CR_BR_C)_m$;

W is $NR_DR_D$, $NR_DC(O)R_D$, $N=C(R_E)$alkyl, $N=C(R_E)$aryl, $N=C(R_E)$heteroaryl, $N=C(R_E)$aralkyl, or $NR_DCR_B=N-OH$;

R' is H, hydroxy, nitro, halo, an optionally substituted alkyl, an optionally substituted cycloalkyl, an optionally substituted alkenyl, an optionally substituted aryl, an optionally substituted heteroaryl, optionally substituted heterocycloalkyl, $OR_B$, or $NR_AR_B$;

Q is H, halo, nitro, halo, hydroxy, an optionally substituted alkyl, an optionally substituted cycloalkyl, an optionally substituted aryloxy, an optionally substituted alkenyl, an optionally substituted aryl, an optionally substituted heteroaryl, optionally substituted heterocycloalkyl, $C(O)OR_B$, $C(O)R_A$, $OR_B$, $NR_AR_B$, $NR_AC(O)R_A$, or $SO_3R_A$; or R' and Q, together with the atoms to which each is attached, forms a cycloalkyl, heterocycloalkyl, aryl, or heteroaryl, each of which is optionally substituted;

V is H, halo, nitro, halo, hydroxy, an optionally substituted alkyl, an optionally substituted cycloalkyl, an optionally substituted aryloxy, an optionally substituted alkenyl, an optionally substituted aryl, an optionally substituted heteroaryl, optionally substituted heterocycloalkyl, $C(O)OR_B$, $C(O)R_A$, $OR_B$, $NR_AR_B$, $NR_AC(O)R_A$, or $SO_3R_A$;

each $R_B$ is independently H, optionally substituted alkyl, optionally substituted aralkyl, or optionally substituted aryl;

each $R_C$ is independently H, optionally substituted alkyl, optionally substituted aralkyl, or optionally substituted aryl;

each $R_D$ is independently H, optionally substituted alkyl, optionally substituted aralkyl, optionally substituted heteroaralkyl, or optionally substituted aryl;

each $R_E$ is independently H, optionally substituted alkyl, optionally substituted aralkyl, optionally substituted heteroaralkyl, or optionally substituted aryl; and each $R_4$ is independently H, OH, halo, an optionally substituted alkyl, or an optionally substituted aryl; or formula III:

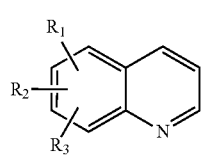

or a pharmaceutically acceptable salt thereof,
wherein, $R_1$ is H, hydroxy, nitro, halo, an optionally substituted alkyl, an optionally substituted cycloalkyl, an optionally substituted alkenyl, an optionally substituted aryl, an optionally substituted heteroaryl, optionally substituted heterocycloalkyl, $OR_B$, or $NR_AR_B$;

$R_2$ is H, hydroxy, nitro, halo, an optionally substituted alkyl, an optionally substituted cycloalkyl, an optionally substituted alkenyl, an optionally substituted aryl, an optionally substituted heteroaryl, optionally substituted heterocycloalkyl, $OR_B$, or $NR_AR_B$;

$R_3$ is $OR_B$ or $NR_AR_B$; or $R_2$ and $R_3$, together with the atoms to which each is attached, may form an optionally substituted heterocyclic or an optionally substituted heteroaryl;

each $R_A$ is independently H, OH, halo, an optionally substituted alkyl, or an optionally substituted aryl, C(O)$NR_BR_B$, or C(O)$R_B$; and each $R_B$ is independently H, optionally substituted alkyl, optionally substituted aralkyl, or optionally substituted aryl.

In another aspect, the invention provides a method of treating a disease or disorder associated with methionine aminopeptidase in a subject, wherein the subject is identified as being in need of a type 2 methionine aminopeptidase inhibitor, the method comprising the step of administering to the subject an effective amount of a compound of formula I, formula II, or formula III, as described herein.

In another aspect, the invention provides a method of treating tuberculosis in a subject, the method comprising the step of administering to the subject an effective amount of a compound of formula I, formula II, or formula III, as described herein.

In another aspect, the invention provides a method of treating bacterial infection in a subject, the method comprising the step of administering to the subject an effective amount of a compound of formula I, formula II, or formula III, as described herein.

In certain aspects, the invention provides a method of inhibiting or reducing methionine aminopeptidase in a subject, the method comprising the step of administering to the subject an effective amount of a compound of formula I, formula II, or formula III, as described herein.

In another aspect, the invention provides for the use of a compound in the manufacture of a medicament for inhibiting type 2 methionine aminopeptidase in a patient, wherein the compound is a compound of formula I, formula II, or formula III.

BRIEF DESCRIPTION OF THE DRAWINGS

FIG. 1: Multiple Sequence Alignment of MtMetAP1a (SEQ ID NO: 15), MtMetAP1c (SEQ ID NO: 13), HsMetAP1 (SEQ ID NO: 14) and EcMetAP1 (SEQ ID NO: 161. The alignment was generated using ClustalW (www.ebi.ac.uk). Both MtMetAPs share a 33% similarity and the metal-chelating residues necessary for catalysis are conserved (*). MtMetAP1a and EcMetAP1 lack the N-terminal extension with a PXXPXP motif present in MtMetAP1c and HsMetAP1 (underlined). Both MtMetAPs have less than 45% similarity to E. coli MetAP1 (EcMetAP1), and less than 48% similarity to human MetAP1 (HsMetAP1).

FIG. 3Ai-iii: Schematic Representation of Plasmids used for In Vivo Target Validation. i. Control plasmid: pSCW35ΔsigF. ii. Sense Construct: pSCW35ΔsigF-(MtMetAP1). iii. Anti-sense Construct: pSCW35ΔsigF-(α-MtMetAP1). The MtMetAP genes were inserted downstream of the acetamide regulated promoter ($P_{ace}$) in pSCW35ΔsigF. FIG. 3B, C. The Expression of MtMetAP1a and MtMetAP1c mRNA in M. tuberculosis as Determined by Quantitative Real-Time RT-PCR. The levels of MtMetAP1a and MtMetAP1c were measured in M. tuberculosis strains transformed with vectors over-expressing the two genes in the sense (FIG. 3Aii) and anti-sense (FIG. 3Aiii) orientation. The quantities of mRNA are shown as fold change compared to the expression in the wild-type with standard error from two independent experiments.

FIG. 4. In Vivo Target Validation of Naphthoquinone Inhibitors. M. tuberculosis knock-in strains of MtMetAP1a and MtMetAP1c and controls were grown in liquid media in the presence of 10 µg/mL compound 4 and DMSO (Table 2). Over-expression of MtMetAP1a (diamonds), Over-expression of MtMetAP1c (squares), Wild-type strain (stars), and sigma factor-F lacking mutant (triangles).

FIG. 6. Effect of Thiazoles on MtMetAPs.

FIG. 7. Effect of Hydroxyquinolines on MtMetAPs.

DETAILED DESCRIPTION OF THE INVENTION

Figure 2:
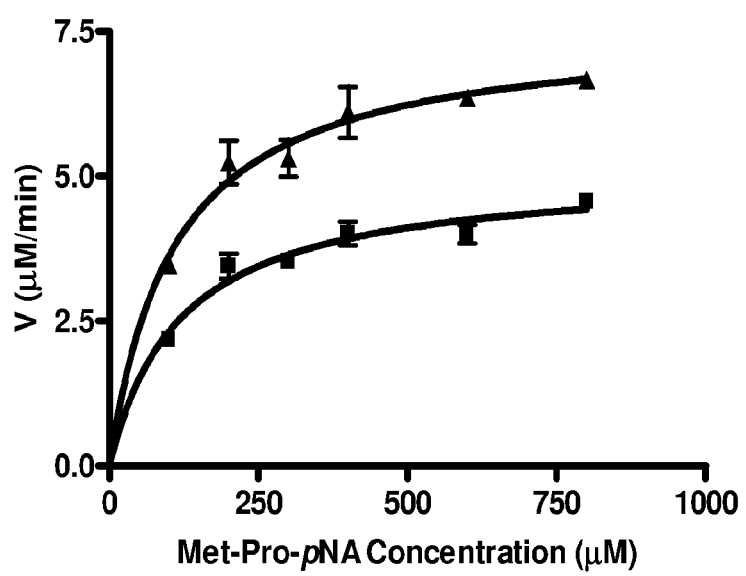
FIG. 2A, B: Purification of Recombinant MetAPs from M. tuberculosis: The recombinant MtMetAP1s were over-expressed in E. coli BL21 cells and purified by affinity chromatography as described in the methods section. A. polyHis-tagged-MtMetAP1c (~32 kDa). B. polyHis-tagged-MtMetAP1a (~28 kDa): Molecular weight marker, Lane 1-un-induced whole cell lysate, Lane 2-induced cell lysate, Lane 3-elution of purified polyHis-tagged MtMetAP1. The SDS-PAGE gel was stained with Coomassie blue.
FIG. 2C. Determination of Kinetic Constants of MtMetAPs. Velocity versus substrate concentration plot for methionine aminopeptidases from M. tuberculosis: MtMetAP1a (triangles) and MtMetAP1c (squares). The total reaction volume was 100 µL (each reaction contained 40 mM HEPES buffer (pH 7.5), 100 mM NaCl, 1 µM $CoCl_2$, 100 µg/mL BSA, 0.1 U/mL ProAP, and 0-800 µM H-Met-Pro-pNA). The background hydrolysis was corrected. The data were from quadruplet experiments and was fitted against the Michealis-Menten equation: V=Vmax*[S]/(Km+[S]) using the Graphpad Prism software for one-site binding hyperbola.

In one aspect, the invention provides a compound of formula I-B:

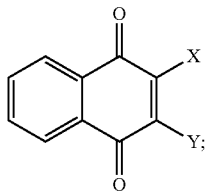

(I-B)

or a pharmaceutically acceptable salt thereof,
wherein,

X is halo, an optionally substituted aryloxy, an optionally substituted aryl, an optionally substituted heteroaryl, C(O)OR$_B$, C(O)R$_A$, OR$_B$, NR$_A$R$_B$, NR$_A$C(O)R$_A$, or SO$_3$R$_A$;

Y is halo, an optionally substituted aryloxy, an optionally substituted aryl, an optionally substituted heteroaryl, optionally substituted heterocycloalkyl, C(O)OR$_A$, C(O)R$_A$, OR$_A$, NR$_A$R$_A$, NR$_A$C(O)R$_A$, or SO$_3$R$_A$;

each R$_A$ is independently H, OH, halo, an optionally substituted alkyl, or an optionally substituted aryl; and each R$_B$ is independently H, optionally substituted alkyl, optionally substituted aralkyl, or optionally substituted aryl.

In one embodiment, X is Cl, Br, F, COOH, an optionally substituted aryloxy, or NR$_A$C(O)R$_A$.

In a further embodiment, aryloxy or R$_A$ is substituted with alkyl, cycloalkyl, heterycycloalkyl, aryl, heteroaryl, halo, haloalkyl, or aralkyl.

In another embodiment, Y is Cl, Br, F, O-Ph, NH(alkyl), NH(aryl), NHCO(aryl), piperidyl, imidazolyl; furanyl; thiophenyl; oxazolyl; isoxazolyl; thiazolyl; pyridinyl; pyrazinyl; pyrimidinyl; pyridazinyl; 1,3,5-, 1,2,4-, 1,2,3-triazinyl; quinolinyl; isoquinolinyl; pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, tetrahydrofuryl, dihydrofuranyl, or pyrrolyl, each of which may be optionally substituted.

In a further embodiment, Y is Cl, Br, F, O-aryl, NH(aryl), piperidyl, or morpholinyl, each of which is optionally substituted.

In one embodiment, the invention provides a compound of formula I-B, selected from the following:

| X | Y |
|---|---|
| Br | 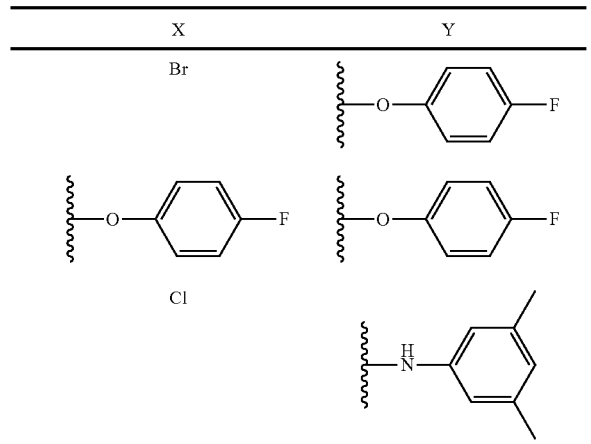 |
| Cl | |
| Cl | |
| COOH | |
| COOH | |

In another aspect, the invention provides a compound of formula II:

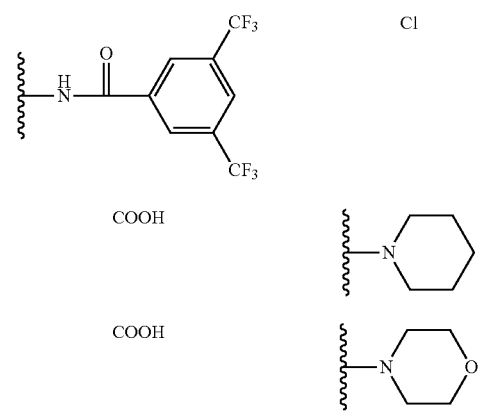

(II)

or a pharmaceutically acceptable salt thereof,
wherein,

Z is absent, (CR$_B$R$_C$)$_m$, O(CR$_B$R$_C$)$_m$, or NR$_D$(CR$_B$R$_C$)$_m$;

W is NR$_D$R$_D$, NR$_D$C(O)R$_D$, N=C(R$_E$)alkyl, N=C(R$_E$)aryl, N=C(R$_E$)heteroaryl, N=C(R$_E$)aralkyl, or NR$_D$CR$_B$=N—OH;

R' is H, OR$_B$, or NR$_A$R$_B$;

Q is H, C(O)OR$_B$, C(O)R$_A$, OR$_B$, NR$_A$R$_B$, NR$_A$C(O)R$_A$, or SO$_3$R$_A$; or

R' and Q, together with the atoms to which each is attached, forms a heterocycloalkyl, or heteroaryl, each of which is optionally substituted;

V is H, C(O)OR$_B$, C(O)R$_A$, OR$_B$, NR$_A$R$_B$, NR$_A$C(O)R$_A$, or SO$_3$R$_A$;

each m is independently 1, 2, or 3;

each R$_B$ is independently H, optionally substituted alkyl, optionally substituted aralkyl, or optionally substituted aryl;

each R$_C$ is independently H, optionally substituted alkyl, optionally substituted aralkyl, or optionally substituted aryl;

each R$_D$ is independently H, optionally substituted alkyl, optionally substituted aralkyl, optionally substituted heteroaralkyl, or optionally substituted aryl;

each R$_E$ is independently H, optionally substituted alkyl, optionally substituted aralkyl, optionally substituted heteroaralkyl, or optionally substituted aryl; and each $R_A$ is independently H, OH, halo, an optionally substituted alkyl, or an optionally substituted aryl.

In certain embodiments, W is $NR_DR_D$, $NR_DC(O)R_D$, or $NR_DCR_B$=N—OH.

In other embodiments, R' is H or $OR_B$; and $R_B$ is an optionally substituted alkyl.

In various embodiments, Q is H or $OR_B$; and $R_B$ is an optionally substituted alkyl.

In still other embodiments, R' and Q, together with the atoms to which each is attached, forms a heterocycloalkyl or heteroaryl, each of which is optionally substituted.

In various embodiments, V is H or $OR_B$, and $R_B$ is an optionally substituted alkyl.

In a first embodiment, the invention provides a compound of formula II-A:

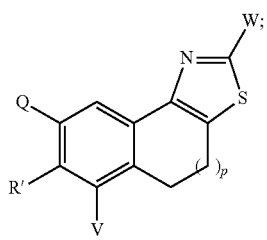

(II-A)

or a pharmaceutically acceptable salt thereof,
wherein,
W is $NR_DR_D$, $NR_DC(O)R_D$, or $NR_DCR_B$=N—OH;
R' is H or $OR_B$;
Q is H or $OR_B$; or
R' and Q, together with the atoms to which each is attached, forms a heterocycloalkyl, which is optionally substituted;
V is H or $OR_B$;
p is 0 or 1;
each $R_B$ is independently H, optionally substituted alkyl, optionally substituted aralkyl, optionally substituted heteroaralkyl, or optionally substituted aryl; and
each $R_D$ is independently H, optionally substituted alkyl, optionally substituted aralkyl, optionally substituted heteroaralkyl, or optionally substituted aryl.

In a second embodiment, the invention provides a compound of formula II-B:

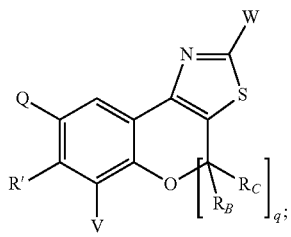

(II-B)

or a pharmaceutically acceptable salt thereof,
wherein,
W is $NR_DR_D$, $NR_DC(O)R_D$ or $NR_DCR_B$=N—OH;
R' is H or $OR_B$;
Q is H or $OR_B$; or
R' and Q, together with the atoms to which each is attached, forms a heterocycloalkyl, which is optionally substituted;

V is H or $OR_B$;
q is 0, 1 or 2;
each $R_B$ is independently H, optionally substituted alkyl, optionally substituted aralkyl, or optionally substituted aryl;
each $R_D$ is independently H, optionally substituted alkyl, optionally substituted aralkyl, optionally substituted heteroaralkyl, or optionally substituted aryl.

In a third embodiment, the invention provides a compound of formula II-C:

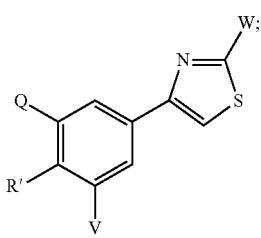

(II-C)

or a pharmaceutically acceptable salt thereof,
wherein,
W is $NR_DR_D$, $NR_DC(O)R_D$, or $NR_DCR_B$=N—OH;
R' is H or $OR_B$;
Q is H or $OR_B$; or
R' and Q, together with the atoms to which each is attached, forms a heterocycloalkyl, which is optionally substituted;
V is H or $OR_B$;
each $R_B$ is independently H, optionally substituted alkyl, optionally substituted aralkyl, or optionally substituted aryl; and
each $R_D$ is independently H, optionally substituted alkyl, optionally substituted aralkyl, optionally substituted heteroaralkyl, or optionally substituted aryl.

In another embodiment, the invention provides for compounds of formula II, selected from the following:

| Z | W | Q | R' | V |
|---|---|---|----|---|
| —CH₂—CH₂— | —NHC(O)CH(OH)Me | H | OMe | H |
| —CH₂—CH₂— | —NHCH₂(2-furyl) | H | OMe | H |
| —CH₂—CH₂— | —NH—CH=NOH | OMe | H | H |
| —CH₂—CH₂— | —NH—CH=NOH | H | H | OMe |
| —CH₂—CH₂— | —NH—CH=NOH | OMe | OMe | H |
| —CH₂—CH₂— | —NH—CH=NOH | —OCH₂O-R' | — | H |
| —OCH₂— | —NH—CH=NOH | —OCH₂O-R' | — | H |
| —OCH₂— | —NH—CH=NOH | H | OMe | H |
| —OCH(Ph)— | —NH—CH=NOH | H | OMe | H |
| —CH₂— | —NH—CH=NOH | H | OMe | H |
| —CH₂—CH₂—CH₂— | —NH—CH=NOH | —OCH₂O-R' | — | H |
| —O—CH₂—CH₂— | —NH—CH=NOH | —OCH₂O-R' | — | H |
| — | —NH—CH=NOH | OMe | OMe | H |

In another aspect, the invention provides a pharmaceutical composition comprising a therapeutically effective amount of a compound described herein, or an embodiment or example described herein, or a pharmaceutically acceptable salt, ester, or prodrug thereof, in combination with a pharmaceutically acceptable carrier or excipient.

In other embodiments, the invention provides a pharmaceutical composition further comprising another anti-viral, anti-bacterial, anti-fungal or anti-cancer agent, and/or an immune modulator, or a pharmaceutically acceptable salt thereof.

In another aspect, the invention provides a kit comprising an effective amount of a compound of formula I, formula II, or formula III in unit dosage form, together with instructions for administering the compound to a subject suffering from or susceptible to a methionine aminopeptidase-related disease.

In one aspect, the invention provides a method of treating a disease or disorder associated with methionine aminopeptidase (MetAP) in a subject, the method comprising the step of administering to the subject an effective amount of a compound of formula I:

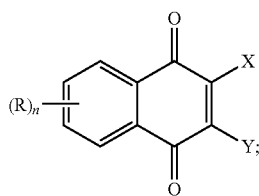

(I)

or a pharmaceutically acceptable salt thereof, wherein,

R is H, hydroxy, nitro, halo, an optionally substituted alkyl, an optionally substituted cycloalkyl, an optionally substituted alkenyl, an optionally substituted aryl, an optionally substituted heteroaryl, optionally substituted heterocycloalkyl, $OR_B$, or $NR_AR_B$;

X is H, halo, nitro, halo, hydroxy, an optionally substituted alkyl, an optionally substituted cycloalkyl, an optionally substituted aryloxy, an optionally substituted alkenyl, an optionally substituted aryl, an optionally substituted heteroaryl, optionally substituted heterocycloalkyl, $C(O)OR_B$, $C(O)R_A$, $OR_B$, $NR_AR_B$, $NR_AC(O)R_A$, or $SO_3R_A$;

Y is H, halo, nitro, halo, hydroxy, an optionally substituted alkyl, an optionally substituted cycloalkyl, an optionally substituted aryloxy, an optionally substituted alkenyl, an optionally substituted aryl, an optionally substituted heteroaryl, optionally substituted heterocycloalkyl, $C(O)OR_B$, $C(O)R_A$, $OR_B$, $NR_AR_B$, $NR_AC(O)R_A$, or $SO_3R_A$;

each $R_A$ is independently H, OH, halo, an optionally substituted alkyl, or an optionally substituted aryl;

each $R_B$ is independently H, optionally substituted alkyl, optionally substituted aralkyl, or optionally substituted aryl; and n is 1, 2, or 3;

formula II:

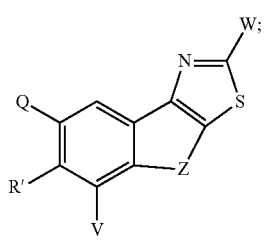

(II)

or a pharmaceutically acceptable salt thereof, wherein,

Z is absent, $(CR_BR_C)_m$, $O(CR_BR_C)_m$, or $NR_D(CR_BR_C)_m$;

W is $NR_DR_D$, $NR_DC(O)R_D$, $N=C(R_E)$alkyl, $N=C(R_E)$aryl, $N=C(R_E)$heteroaryl, $N=C(R_E)$aralkyl, or $NR_DCR_B=N-OH$;

R' is H, hydroxy, nitro, halo, an optionally substituted alkyl, an optionally substituted cycloalkyl, an optionally substituted alkenyl, an optionally substituted aryl, an optionally substituted heteroaryl, optionally substituted heterocycloalkyl, $OR_B$, or $NR_AR_B$;

Q is H, halo, nitro, halo, hydroxy, an optionally substituted alkyl, an optionally substituted cycloalkyl, an optionally substituted aryloxy, an optionally substituted alkenyl, an optionally substituted aryl, an optionally substituted heteroaryl, optionally substituted heterocycloalkyl, $C(O)OR_B$, $C(O)R_A$, $OR_B$, $NR_AR_B$, $NR_AC(O)R_A$, or $SO_3R_A$; or R' and Q, together with the atoms to which each is attached, forms a cycloalkyl, heterocycloalkyl, aryl, or heteroaryl, each of which is optionally substituted;

V is H, halo, nitro, halo, hydroxy, an optionally substituted alkyl, an optionally substituted cycloalkyl, an optionally substituted aryloxy, an optionally substituted alkenyl, an optionally substituted aryl, an optionally substituted heteroaryl, optionally substituted heterocycloalkyl, $C(O)OR_B$, $C(O)R_A$, $OR_B$, $NR_AR_B$, $NR_AC(O)R_A$, or $SO_3R_A$;

each $R_B$ is independently H, optionally substituted alkyl, optionally substituted aralkyl, or optionally substituted aryl;

each $R_C$ is independently H, optionally substituted alkyl, optionally substituted aralkyl, or optionally substituted aryl;

each $R_D$ is independently H, optionally substituted alkyl, optionally substituted aralkyl, optionally substituted heteroaralkyl, or optionally substituted aryl;

each $R_E$ is independently H, optionally substituted alkyl, optionally substituted aralkyl, optionally substituted heteroaralkyl, or optionally substituted aryl; and each $R_A$ is independently H, OH, halo, an optionally substituted alkyl, or an optionally substituted aryl; or formula III:

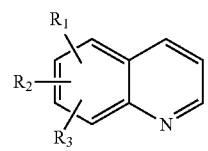

(III)

or a pharmaceutically acceptable salt thereof, wherein, $R_1$ is H, hydroxy, nitro, halo, an optionally substituted alkyl, an optionally substituted cycloalkyl, an optionally substituted alkenyl, an optionally substituted aryl, an optionally substituted heteroaryl, optionally substituted heterocycloalkyl, $OR_B$, or $NR_AR_B$;

$R_2$ is H, hydroxy, nitro, halo, an optionally substituted alkyl, an optionally substituted cycloalkyl, an optionally substituted alkenyl, an optionally substituted aryl, an optionally substituted heteroaryl, optionally substituted heterocycloalkyl, $OR_B$, or $NR_AR_B$;

$R_3$ is $OR_B$ or $NR_AR_B$; or $R_2$ and $R_3$, together with the atoms to which each is attached, may form an optionally substituted heterocyclic or an optionally substituted heteroaryl;

each $R_A$ is independently H, OH, halo, an optionally substituted alkyl, or an optionally substituted aryl, $C(O)NR_BR_B$, or $C(O)R_B$; and each $R_B$ is independently H, optionally substituted alkyl, optionally substituted aralkyl, or optionally substituted aryl.

In one embodiment, the invention provides a method wherein the compound is a compound of formula I:

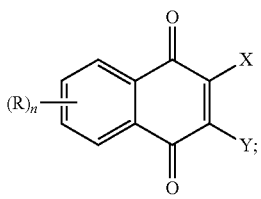

(I)

or a pharmaceutically acceptable salt thereof,
wherein,

R is H, hydroxy, nitro, halo, an optionally substituted alkyl, an optionally substituted alkenyl, an optionally substituted cycloalkyl, an optionally substituted aryl, an optionally substituted heteroaryl, optionally substituted heterocycloalkyl, $OR_B$, or $NR_AR_B$;

X is H, halo, nitro, hydroxy, an optionally substituted alkyl, an optionally substituted cycloalkyl, an optionally substituted aryloxy, an optionally substituted alkenyl, an optionally substituted aryl, an optionally substituted heteroaryl, optionally substituted heterocycloalkyl, $C(O)OR_B$, $C(O)R_A$, $OR_B$, $NR_A$, $OR_B$, $NR_AC(O)R_A$, or $SO_3R_A$;

Y is H, halo, nitro, halo, hydroxy, an optionally substituted alkyl, an optionally substituted cycloalkyl, an optionally substituted aryloxy, an optionally substituted alkenyl, an optionally substituted aryl, an optionally substituted heteroaryl, optionally substituted heterocycloalkyl, $C(O)OR_B$, $C(O)R_A$, $OR_B$, $NR_AR_B$, $NR_AC(O)R_A$, or $SO_3R_A$;

each $R_A$ is independently H, OH, halo, an optionally substituted alkyl, or an optionally substituted aryl;

each $R_B$ is independently H, optionally substituted alkyl, optionally substituted aralkyl, or optionally substituted aryl; and n is 1, 2, or 3.

In a further embodiment, X is H, Cl, Br, F, methyl, ethyl, propyl, i-propyl, butyl, s-butyl, t-butyl, OH, $NH_2$, O-Ph, NH(alkyl), NH(aryl), NHCO(aryl), C(O)OH, piperidyl, phthaloyl, imidazolyl; furanyl; thiophenyl (or thienyl or thiofuranyl); pyrazolyl; oxazolyl; isoxazolyl; thiazolyl; 1,2,3-, 1,2,4-, 1,2,5-, and 1,3,4-oxadiazolyl; isothiazolyl; pyridinyl; pyrazinyl; pyrimidinyl; pyridazinyl; 1,3,5-, 1,2,4-, 1,2,3-triazinyl; benzothiofuranyl, isobenzothiofuranyl, benzisoxazolyl, benzoxazolyl, purinyl, anthranilyl; quinolinyl; isoquinolinyl; benzoxazinyl; [1,3]dioxolane, pyrrolidinyl, pyrazolinyl, pyrazolidinyl, imidazolinyl, piperidinyl, piperazinyl, oxazolidinyl, isoxazolidinyl, morpholinyl, thiazolidinyl, isothiazolidinyl, tetrahydrofuryl, furanyl, dihydrofuranyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiodiazolyl, oxathiazolyl, oxadiazoly, pyranyl, dihydropyranyl, pyridinyl, piperidinyl, pyridazinyl, pyrimidinyl, pyrazinyl, piperazinyl, triazinyl, isoxazinyl, oxazolidinyl, isoxazolidinyl, oxathiazinyl, oxadiazinyl, morpholinyl, azepinyl, oxepinyl, thiepinyl, diazepinyl, naphthyridinyl, thiazolpyrimidinyl, thienopyrimidinyl, pyrimidopyrimidinyl, or pyridopyrimidinyl; each of which may be optionally substituted.

In another further embodiment, Y is H, Cl, Br, F, methyl, ethyl, propyl, i-propyl, butyl, s-butyl, t-butyl, phythyl, OH, $NH_2$, O-Ph, NH(alkyl), NH(aryl), NHCO(aryl), C(O)OH, piperidyl, phthaloyl, imidazolyl; furanyl; thiophenyl (or thienyl or thiofuranyl); pyrazolyl; oxazolyl; isoxazolyl; thiazolyl; 1,2,3-, 1,2,4-, 1,2,5-, and 1,3,4-oxadiazolyl; isothiazolyl; pyridinyl; pyrazinyl; pyrimidinyl; pyridazinyl; 1,3,5-, 1,2,4-, 1,2,3-triazinyl; benzothiofuranyl, isobenzothiofuranyl, benzisoxazolyl, benzoxazolyl, purinyl, anthranilyl; quinolinyl; isoquinolinyl; benzoxazinyl; [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, tetrahydrofuryl, furanyl, dihydrofuranyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiodiazolyl, oxathiazolyl, oxadiazoly, pyranyl, dihydropyranyl, pyridinyl, piperidinyl, pyridazinyl, pyrimidinyl, pyrazinyl, piperazinyl, triazinyl, isoxazinyl, oxazolidinyl, isoxazolidinyl, oxathiazinyl, oxadiazinyl, morpholinyl, azepinyl, oxepinyl, thiepinyl, diazepinyl, naphthyridinyl, thiazolpyrimidinyl, thienopyrimidinyl, pyrimidopyrimidinyl, or pyridopyrimidinyl; each of which may be optionally substituted.

In another embodiment, the invention provides a method of treating a disease or disorder associated with methionine aminopeptidase (MetAP) in a subject, the method comprising the step of administering to the subject an effective amount of a compound of formula I-A:

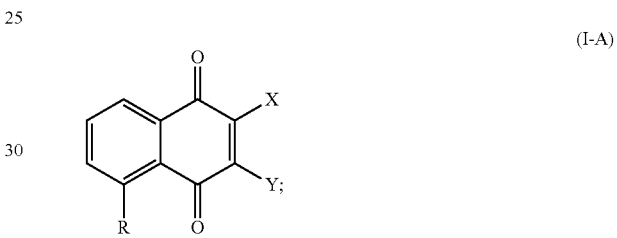

(I-A)

or a pharmaceutically acceptable salt thereof,
wherein,

R is H or hydroxy;

X is H, Cl, Br, F, methyl, OH, $NH_2$, O-Ph, NH(alkyl), NH(aryl), NHCO(aryl), C(O)OH, piperidyl, or phthaloyl, each of which may be optionally substituted; and Y is H, Cl, Br, F, methyl, phythyl, OH, $NH_2$, O-Ph, NH(alkyl), NH(aryl), NHCO(aryl), C(O)OH, piperidyl, or phthaloyl, each of which may be optionally substituted.

In another embodiment, the invention provides a method of treating a disease or disorder associated with methionine aminopeptidase (MetAP) in a subject, the method comprising the step of administering to the subject an effective amount of a compound of formula II:

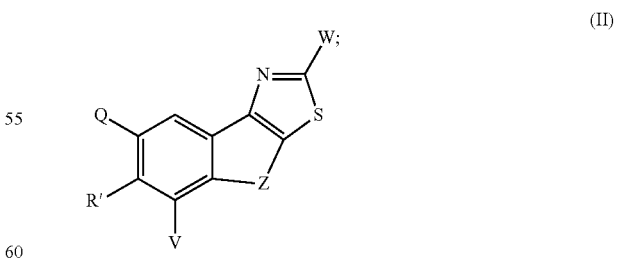

(II)

or a pharmaceutically acceptable salt thereof,
wherein,

Z is absent, $(CR_BR_C)_m$, $O(CR_BR_C)_m$, or $NR_D(CR_BR_C)_m$;

W is $NR_DR_D$, $NR_DC(O)R_D$, $N=C(R_E)$alkyl, $N=C(R_E)$aryl, $N=C(R_E)$heteroaryl, $N=C(R_E)$aralkyl, or $NR_DCR_B=N-OH$;

R' is H, hydroxy, nitro, halo, an optionally substituted alkyl, an optionally substituted cycloalkyl, an optionally substituted alkenyl, an optionally substituted aryl, an optionally substituted heteroaryl, optionally substituted heterocycloalkyl, $OR_B$, or $NR_AR_B$;

Q is H, halo, nitro, halo, hydroxy, an optionally substituted alkyl, an optionally substituted cycloalkyl, an optionally substituted aryloxy, an optionally substituted alkenyl, an optionally substituted aryl, an optionally substituted heteroaryl, optionally substituted heterocycloalkyl, $C(O)OR_B$, $C(O)R_A$, $OR_B$, $NR_AR_B$, $NR_AC(O)R_A$, or $SO_3R_A$; or R' and Q, together with the atoms to which each is attached, forms a cycloalkyl, heterocycloalkyl, aryl, or heteroaryl, each of which is optionally substituted;

V is H, halo, nitro, halo, hydroxy, an optionally substituted alkyl, an optionally substituted cycloalkyl, an optionally substituted aryloxy, an optionally substituted alkenyl, an optionally substituted aryl, an optionally substituted heteroaryl, optionally substituted heterocycloalkyl, $C(O)OR_B$, $C(O)R_A$, $OR_B$, $NR_AR_B$, $NR_AC(O)R_A$, or $SO_3R_A$;

each $R_B$ is independently H, optionally substituted alkyl, optionally substituted aralkyl, or optionally substituted aryl;

each $R_C$ is independently H, optionally substituted alkyl, optionally substituted aralkyl, or optionally substituted aryl;

each $R_D$ is independently H, optionally substituted alkyl, optionally substituted aralkyl, optionally substituted heteroaralkyl, or optionally substituted aryl;

each $R_E$ is independently H, optionally substituted alkyl, optionally substituted aralkyl, optionally substituted heteroaralkyl, or optionally substituted aryl; and each $R_A$ is independently H, OH, halo, an optionally substituted alkyl, or an optionally substituted aryl.

In a further embodiment, the invention provides a method wherein the compound is of formula II-A:

(II-A)

or a pharmaceutically acceptable salt thereof, wherein,

W is $NR_DR_D$, $NR_DC(O)R_D$, $N=C(R_E)$alkyl, $N=C(R_E)$aryl, $N=C(R_E)$heteroaryl, $N=C(R_E)$aralkyl, or $NR_DCR_B=N-OH$;

R' is H or $OR_B$;

Q is H or $OR_B$; or

R' and Q, together with the atoms to which each is attached, forms a heterocycloalkyl, which is optionally substituted;

V is H or $OR_B$;

each $R_B$ is independently H, optionally substituted alkyl, optionally substituted aralkyl, optionally substituted heteroaralkyl, or optionally substituted aryl;

each $R_D$ is independently H, optionally substituted alkyl, optionally substituted aralkyl, optionally substituted heteroaralkyl, or optionally substituted aryl; and each $R_E$ is independently H, optionally substituted alkyl, optionally substituted aralkyl, optionally substituted heteroaralkyl, or optionally substituted aryl.

In another embodiment, the invention provides a method wherein the compound is of formula II-B:

(II-B)

or a pharmaceutically acceptable salt thereof, wherein,

W is $NR_DR_D$, $NR_DC(O)R_D$, $N=C(R_E)$alkyl, $N=C(R_E)$aryl, $N=C(R_E)$heteroaryl, $N=C(R_E)$aralkyl, or $NR_DCR_B=N-OH$;

R' is H or $OR_B$;

Q is H or $OR_B$; or

R' and Q, together with the atoms to which each is attached, forms a heterocycloalkyl, which is optionally substituted;

V is H or $OR_B$;

each $R_B$ is independently H, optionally substituted alkyl, optionally substituted aralkyl, or optionally substituted aryl;

each $R_C$ is independently H, optionally substituted alkyl, optionally substituted aralkyl, or optionally substituted aryl;

each $R_D$ is independently H, optionally substituted alkyl, optionally substituted aralkyl, optionally substituted heteroaralkyl, or optionally substituted aryl; and each $R_E$ is independently H, optionally substituted alkyl, optionally substituted aralkyl, optionally substituted heteroaralkyl, or optionally substituted aryl.

In another embodiment, the invention provides a method wherein the compound is of formula II-C:

(II-C)

or a pharmaceutically acceptable salt thereof, wherein,

W is $NR_DR_D$, $NR_DC(O)R_D$, $N=C(R_E)$alkyl, $N=C(R_E)$aryl, $N=C(R_E)$heteroaryl, $N=C(R_E)$aralkyl, or $NR_DCR_B=N-OH$;

R' is H or $OR_B$;

Q is H or $OR_B$; or

R' and Q, together with the atoms to which each is attached, forms a heterocycloalkyl, which is optionally substituted;

V is H or $OR_B$;

each $R_B$ is independently H, optionally substituted alkyl, optionally substituted aralkyl, or optionally substituted aryl;

each $R_D$ is independently H, optionally substituted alkyl, optionally substituted aralkyl, optionally substituted heteroaralkyl, or optionally substituted aryl; and each $R_E$ is independently H, optionally substituted alkyl, optionally substituted aralkyl, optionally substituted heteroaralkyl, or optionally substituted aryl.

In certain embodiments, the invention provides a method of treating a disease or disorder associated with methionine aminopeptidase (MetAP) in a subject, the method comprising the step of administering to the subject an effective amount of a compound of formula III:

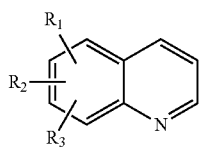
(III)

or a pharmaceutically acceptable salt thereof,
wherein, $R_1$ is H, hydroxy, nitro, halo, an optionally substituted alkyl, an optionally substituted cycloalkyl, an optionally substituted alkenyl, an optionally substituted aryl, an optionally substituted heteroaryl, optionally substituted heterocycloalkyl, $OR_B$, or $NR_AR_B$;

$R_2$ is H, hydroxy, nitro, halo, an optionally substituted alkyl, an optionally substituted cycloalkyl, an optionally substituted alkenyl, an optionally substituted aryl, an optionally substituted heteroaryl, optionally substituted heterocycloalkyl, $OR_B$, or $NR_AR_B$;

$R_3$ is $OR_B$ or $NR_AR_B$; or $R_2$ and $R_3$, together with the atoms to which each is attached, may form an optionally substituted heterocyclic or an optionally substituted heteroaryl;

each $R_A$ is independently H, OH, halo, an optionally substituted alkyl, or an optionally substituted aryl, C(O)$NR_BR_B$, or C(O)$R_B$;

each $R_A$ is independently H, OH, halo, an optionally substituted alkyl, or an optionally substituted aryl; and each $R_B$ is independently H, optionally substituted alkyl, optionally substituted aralkyl, or optionally substituted aryl.

In a further embodiment, the invention provides a method wherein the compound is of formula III-A:

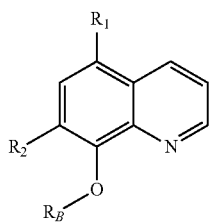
(III-A)

or a pharmaceutically acceptable salt thereof,
wherein, $R_1$ is H or halo;

$R_2$ is H, halo, or an optionally substituted alkyl;

$R_3$ is $OR_B$ or $NR_AR_B$; or $R_2$ and $R_3$, together with the atoms to which each is attached, may form an optionally substituted heterocyclic or an optionally substituted heteroaryl;

each $R_A$ is independently H, OH, halo, an optionally substituted alkyl, or an optionally substituted aryl, C(O)$NR_BR_B$, or C(O)$R_B$; and each $R_B$ is independently H, optionally substituted alkyl, optionally substituted aralkyl, or optionally substituted aryl.

In another aspect, the invention provides a method of treating a disease or disorder associated with methionine aminopeptidase in a subject, wherein the subject is identified as being in need of a type 2 methionine aminopeptidase inhibitor, the method comprising the step of administering to the subject an effective amount of a compound of formula I:

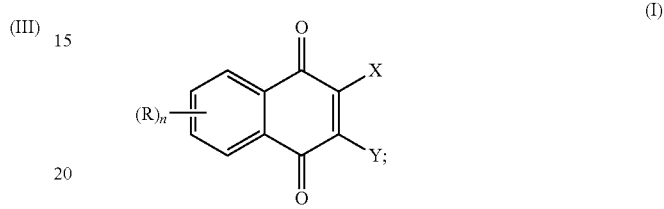
(I)

or a pharmaceutically acceptable salt thereof,
wherein,

R is H, hydroxy, nitro, halo, an optionally substituted alkyl, an optionally substituted cycloalkyl, an optionally substituted alkenyl, an optionally substituted aryl, an optionally substituted heteroaryl, optionally substituted heterocycloalkyl, $OR_B$, or $NR_AR_B$;

X is H, halo, nitro, halo, hydroxy, an optionally substituted alkyl, an optionally substituted cycloalkyl, an optionally substituted aryloxy, an optionally substituted alkenyl, an optionally substituted aryl, an optionally substituted heteroaryl, optionally substituted heterocycloalkyl, C(O)$OR_B$, C(O)$R_A$, $OR_B$, $NR_AR_B$, $NR_AC(O)R_A$, or $SO_3R_A$;

Y is H, halo, nitro, halo, hydroxy, an optionally substituted alkyl, an optionally substituted cycloalkyl, an optionally substituted aryloxy, an optionally substituted alkenyl, an optionally substituted aryl, an optionally substituted heteroaryl, optionally substituted heterocycloalkyl, C(O)$OR_B$, C(O)$R_A$, $OR_B$, $NR_AR_B$, $NR_AC(O)R_A$, or $SO_3R_A$;

each $R_A$ is independently H, OH, halo, an optionally substituted alkyl, or an optionally substituted aryl;

each $R_B$ is independently H, optionally substituted alkyl, optionally substituted aralkyl, or optionally substituted aryl; and n is 1, 2, or 3;

formula II:

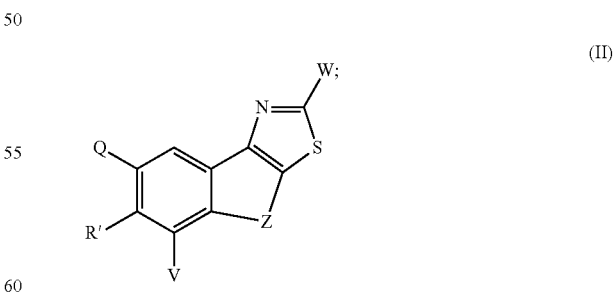
(II)

or a pharmaceutically acceptable salt thereof,
wherein,

Z is absent, $(CR_BR_C)_m$, $O(CR_BR_C)_m$, or $NR_D(CR_BR_C)_m$;

W is $NR_DR_D$, $NR_DC(O)R_D$, N=C($R_E$)alkyl, N=C($R_E$)aryl, N=C($R_E$)heteroaryl, N=C($R_E$)aralkyl, or $NR_DCR_B$=N—OH;

R' is H, hydroxy, nitro, halo, an optionally substituted alkyl, an optionally substituted cycloalkyl, an optionally substituted alkenyl, an optionally substituted aryl, an optionally substituted heteroaryl, optionally substituted heterocycloalkyl, $OR_B$, or $NR_AR_B$;

Q is H, halo, nitro, halo, hydroxy, an optionally substituted alkyl, an optionally substituted cycloalkyl, an optionally substituted aryloxy, an optionally substituted alkenyl, an optionally substituted aryl, an optionally substituted heteroaryl, optionally substituted heterocycloalkyl, $C(O)OR_B$, $C(O)R_A$, $OR_B$, $NR_AR_B$, $NR_AC(O)R_A$, or $SO_3R_A$; or R' and Q, together with the atoms to which each is attached, forms a cycloalkyl, heterocycloalkyl, aryl, or heteroaryl, each of which is optionally substituted;

V is H, halo, nitro, halo, hydroxy, an optionally substituted alkyl, an optionally substituted cycloalkyl, an optionally substituted aryloxy, an optionally substituted alkenyl, an optionally substituted aryl, an optionally substituted heteroaryl, optionally substituted heterocycloalkyl, $C(O)OR_B$, $C(O)R_A$, $OR_B$, $NR_AR_B$, $NR_AC(O)R_A$, or $SO_3R_A$;

each $R_B$ is independently H, optionally substituted alkyl, optionally substituted aralkyl, or optionally substituted aryl;

each $R_C$ is independently H, optionally substituted alkyl, optionally substituted aralkyl, or optionally substituted aryl;

each $R_D$ is independently H, optionally substituted alkyl, optionally substituted aralkyl, optionally substituted heteroaralkyl, or optionally substituted aryl;

each $R_E$ is independently H, optionally substituted alkyl, optionally substituted aralkyl, optionally substituted heteroaralkyl, or optionally substituted aryl; and each $R_A$ is independently H, OH, halo, an optionally substituted alkyl, or an optionally substituted aryl; or formula III:

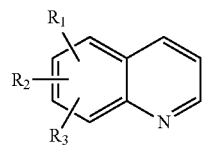

or a pharmaceutically acceptable salt thereof,
wherein, $R_1$ is H, hydroxy, nitro, halo, an optionally substituted alkyl, an optionally substituted cycloalkyl, an optionally substituted alkenyl, an optionally substituted aryl, an optionally substituted heteroaryl, optionally substituted heterocycloalkyl, $OR_B$, or $NR_AR_B$;

$R_2$ is H, hydroxy, nitro, halo, an optionally substituted alkyl, an optionally substituted cycloalkyl, an optionally substituted alkenyl, an optionally substituted aryl, an optionally substituted heteroaryl, optionally substituted heterocycloalkyl, $OR_B$, or $NR_AR_B$;

$R_3$ is $OR_B$ or $NR_AR_B$; or $R_2$ and $R_3$, together with the atoms to which each is attached, may form an optionally substituted heterocyclic or an optionally substituted heteroaryl;

each $R_A$ is independently H, OH, halo, an optionally substituted alkyl, or an optionally substituted aryl, $C(O)NR_BR_B$, or $C(O)R_B$; and each $R_B$ is independently H, optionally substituted alkyl, optionally substituted aralkyl, or optionally substituted aryl.

In certain embodiments, the disease or disorder associated with methionine aminopeptidase is selected from: tuberculosis, bacterial infection, tumor or cancer growth (neoplasia), skin disorders, neovascularization, inflammatory and arthritic diseases, retinoblastoma, cystoid macular edema (CME), exudative age-related macular degeneration (AMD), diabetic retinopathy, diabetic macular edema, or ocular inflammatory disorders.

In another aspect, the invention provides a method of treating tuberculosis in a subject, the method comprising the step of administering to the subject an effective amount of a compound of formula I:

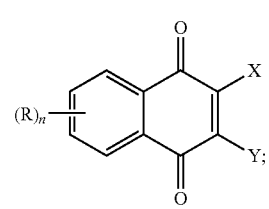

or a pharmaceutically acceptable salt thereof,
wherein,

R is H, hydroxy, nitro, halo, an optionally substituted alkyl, an optionally substituted cycloalkyl, an optionally substituted alkenyl, an optionally substituted aryl, an optionally substituted heteroaryl, optionally substituted heterocycloalkyl, $OR_B$, or $NR_AR_B$;

X is H, halo, nitro, halo, hydroxy, an optionally substituted alkyl, an optionally substituted cycloalkyl, an optionally substituted aryloxy, an optionally substituted alkenyl, an optionally substituted aryl, an optionally substituted heteroaryl, optionally substituted heterocycloalkyl, $C(O)OR_B$, $C(O)R_A$, $OR_B$, $NR_AR_B$, $NR_AC(O)R_A$, or $SO_3R_A$;

Y is H, halo, nitro, halo, hydroxy, an optionally substituted alkyl, an optionally substituted cycloalkyl, an optionally substituted aryloxy, an optionally substituted alkenyl, an optionally substituted aryl, an optionally substituted heteroaryl, optionally substituted heterocycloalkyl, $C(O)OR_B$, $C(O)R_A$, $OR_B$, $NR_AR_B$, $NR_AC(O)R_A$, or $SO_3R_A$;

each $R_A$ is independently H, OH, halo, an optionally substituted alkyl, or an optionally substituted aryl;

each $R_B$ is independently H, optionally substituted alkyl, optionally substituted aralkyl, or optionally substituted aryl; and n is 1, 2, or 3;

formula II:

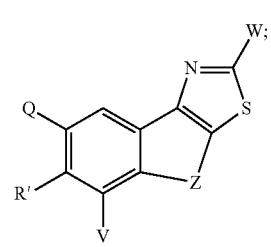

or a pharmaceutically acceptable salt thereof,
wherein,

Z is absent, $(CR_BR_C)_m$, $O(CR_BR_C)_m$, or $NR_D(CR_BR_C)_m$;

W is $NR_DR_D$, $NR_DC(O)R_D$, N=C($R_E$)alkyl, N=C($R_E$)aryl, N=C($R_E$)heteroaryl, N=C($R_E$)aralkyl, or $NR_DCR_B$=N—OH;

R' is H, hydroxy, nitro, halo, an optionally substituted alkyl, an optionally substituted cycloalkyl, an optionally substituted alkenyl, an optionally substituted aryl, an optionally substituted heteroaryl, optionally substituted heterocycloalkyl, $OR_B$, or $NR_AR_B$;

Q is H, halo, nitro, halo, hydroxy, an optionally substituted alkyl, an optionally substituted cycloalkyl, an optionally substituted aryloxy, an optionally substituted alkenyl, an optionally substituted aryl, an optionally substituted heteroaryl, optionally substituted heterocycloalkyl, $C(O)OR_B$, $C(O)R_A$, $OR_B$, $NR_AR_B$, $NR_AC(O)R_A$, or $SO_3R_A$; or R' and Q, together with the atoms to which each is attached, forms a cycloalkyl, heterocycloalkyl, aryl, or heteroaryl, each of which is optionally substituted;

V is H, halo, nitro, halo, hydroxy, an optionally substituted alkyl, an optionally substituted cycloalkyl, an optionally substituted aryloxy, an optionally substituted alkenyl, an optionally substituted aryl, an optionally substituted heteroaryl, optionally substituted heterocycloalkyl, $C(O)OR_B$, $C(O)R_A$, $OR_B$, $NR_AR_B$, $NR_AC(O)R_A$, or $SO_3R_A$;

each $R_B$ is independently H, optionally substituted alkyl, optionally substituted aralkyl, or optionally substituted aryl;

each $R_C$ is independently H, optionally substituted alkyl, optionally substituted aralkyl, or optionally substituted aryl;

each $R_D$ is independently H, optionally substituted alkyl, optionally substituted aralkyl, optionally substituted heteroaralkyl, or optionally substituted aryl;

each $R_E$ is independently H, optionally substituted alkyl, optionally substituted aralkyl, optionally substituted heteroaralkyl, or optionally substituted aryl; and each $R_A$ is independently H, OH, halo, an optionally substituted alkyl, or an optionally substituted aryl; or formula III:

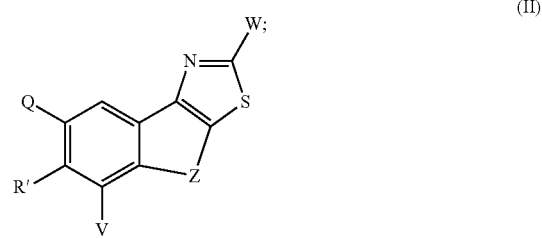

or a pharmaceutically acceptable salt thereof,
wherein, $R_1$ is H, hydroxy, nitro, halo, an optionally substituted alkyl, an optionally substituted cycloalkyl, an optionally substituted alkenyl, an optionally substituted aryl, an optionally substituted heteroaryl, optionally substituted heterocycloalkyl, $OR_B$, or $NR_AR_B$;

$R_2$ is H, hydroxy, nitro, halo, an optionally substituted alkyl, an optionally substituted cycloalkyl, an optionally substituted alkenyl, an optionally substituted aryl, an optionally substituted heteroaryl, optionally substituted heterocycloalkyl, $OR_B$, or $NR_AR_B$;

$R_3$ is $OR_B$ or $NR_AR_B$; or $R_2$ and $R_3$, together with the atoms to which each is attached, may form an optionally substituted heterocyclic or an optionally substituted heteroaryl;

each $R_A$ is independently H, OH, halo, an optionally substituted alkyl, or an optionally substituted aryl, C(O)$NR_BR_B$, or $C(O)R_B$; and each $R_B$ is independently H, optionally substituted alkyl, optionally substituted aralkyl, or optionally substituted aryl.

In one embodiment, the compound inhibits type 2 methionine aminopeptidase to thereby treat the tuberculosis.

In another aspect, the invention provides a method of treating bacterial infection in a subject, the method comprising the step of administering to the subject an effective amount of a compound of formula I:

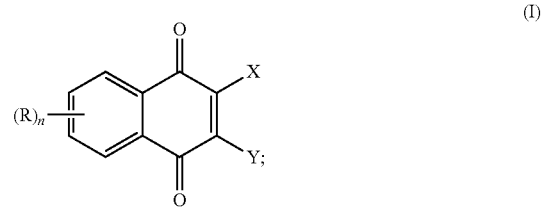

or a pharmaceutically acceptable salt thereof,
wherein,

R is H, hydroxy, nitro, halo, an optionally substituted alkyl, an optionally substituted cycloalkyl, an optionally substituted alkenyl, an optionally substituted aryl, an optionally substituted heteroaryl, optionally substituted heterocycloalkyl, $OR_B$, or $NR_AR_B$;

X is H, halo, nitro, halo, hydroxy, an optionally substituted alkyl, an optionally substituted cycloalkyl, an optionally substituted aryloxy, an optionally substituted alkenyl, an optionally substituted aryl, an optionally substituted heteroaryl, optionally substituted heterocycloalkyl, $C(O)OR_B$, $C(O)R_A$, $OR_B$, $NR_AR_B$, $NR_AC(O)R_A$, or $SO_3R_A$;

Y is H, halo, nitro, halo, hydroxy, an optionally substituted alkyl, an optionally substituted cycloalkyl, an optionally substituted aryloxy, an optionally substituted alkenyl, an optionally substituted aryl, an optionally substituted heteroaryl, optionally substituted heterocycloalkyl, $C(O)OR_B$, $C(O)R_A$, $OR_B$, $NR_AR_B$, $NR_AC(O)R_A$, or $SO_3R_A$; each $R_A$ is independently H, OH, halo, an optionally substituted alkyl, or an optionally substituted aryl;

each $R_B$ is independently H, optionally substituted alkyl, optionally substituted aralkyl, or optionally substituted aryl; and n is 1, 2, or 3;
formula II:

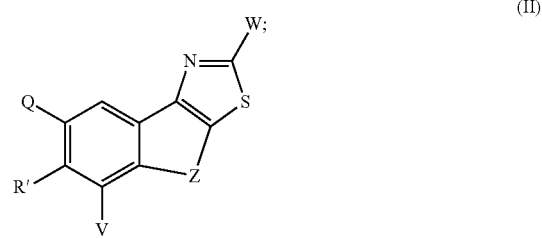

or a pharmaceutically acceptable salt thereof,
wherein,

Z is absent, $(CR_BR_C)_m$, $O(CR_BR_C)_m$, or $NR_D(CR_BR_C)_m$;

W is $NR_DR_D$, $NR_DC(O)R_D$, $N=C(R_E)$alkyl, $N=C(R_E)$aryl, $N=C(R_E)$heteroaryl, $N=C(R_E)$aralkyl, or $NR_DCR_B=N-OH$;

R' is H, hydroxy, nitro, halo, an optionally substituted alkyl, an optionally substituted cycloalkyl, an optionally substituted alkenyl, an optionally substituted aryl, an optionally substituted heteroaryl, optionally substituted heterocycloalkyl, $OR_B$, or $NR_AR_B$;

Q is H, halo, nitro, halo, hydroxy, an optionally substituted alkyl, an optionally substituted cycloalkyl, an optionally substituted aryloxy, an optionally substituted alkenyl, an optionally substituted aryl, an optionally substituted heteroaryl, optionally substituted heterocycloalkyl, C(O)OR$_B$, C(O)R$_A$, OR$_B$, NR$_A$R$_B$, NR$_A$C(O)R$_A$, or SO$_3$R$_A$; or R' and Q, together with the atoms to which each is attached, forms a cycloalkyl, heterocycloalkyl, aryl, or heteroaryl, each of which is optionally substituted;

V is H, halo, nitro, halo, hydroxy, an optionally substituted alkyl, an optionally substituted cycloalkyl, an optionally substituted aryloxy, an optionally substituted alkenyl, an optionally substituted aryl, an optionally substituted heteroaryl, optionally substituted heterocycloalkyl, C(O)OR$_B$, C(O)R$_A$, OR$_B$, NR$_A$R$_B$, NR$_A$C(O)R$_A$, or SO$_3$R$_A$;

each R$_B$ is independently H, optionally substituted alkyl, optionally substituted aralkyl, or optionally substituted aryl;

each R$_C$ is independently H, optionally substituted alkyl, optionally substituted aralkyl, or optionally substituted aryl;

each R$_D$ is independently H, optionally substituted alkyl, optionally substituted aralkyl, optionally substituted heteroaralkyl, or optionally substituted aryl;

each R$_E$ is independently H, optionally substituted alkyl, optionally substituted aralkyl, optionally substituted heteroaralkyl, or optionally substituted aryl; and each R$_A$ is independently H, OH, halo, an optionally substituted alkyl, or an optionally substituted aryl; or formula III:

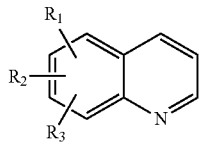

(III)

or a pharmaceutically acceptable salt thereof,
wherein,

R$_1$ is H, hydroxy, nitro, halo, an optionally substituted alkyl, an optionally substituted cycloalkyl, an optionally substituted alkenyl, an optionally substituted aryl, an optionally substituted heteroaryl, optionally substituted heterocycloalkyl, OR$_B$, or NR$_A$R$_B$;

R$_2$ is H, hydroxy, nitro, halo, an optionally substituted alkyl, an optionally substituted cycloalkyl, an optionally substituted alkenyl, an optionally substituted aryl, an optionally substituted heteroaryl, optionally substituted heterocycloalkyl, OR$_B$, or NR$_A$R$_B$;

R$_3$ is OR$_B$ or NR$_A$R$_B$; or

R$_2$ and R$_3$, together with the atoms to which each is attached, may form an optionally substituted heterocyclic or an optionally substituted heteroaryl;

each R$_A$ is independently H, OH, halo, an optionally substituted alkyl, or an optionally substituted aryl, C(O)NR$_B$R$_B$, or C(O)R$_B$; and each R$_B$ is independently H, optionally substituted alkyl, optionally substituted aralkyl, or optionally substituted aryl.

In certain embodiments, the compound inhibits type 2 methionine aminopeptidase to thereby treat the bacterial infection.

In various embodiments, the disease or disorder associated with methionine aminopeptidase is tumor or cancer growth (neoplasia).

In a further embodiment, the disease or disorder is ocular cancer, rectal cancer, colon cancer, cervical cancer, prostate cancer, breast cancer and bladder cancer, oral cancer, benign and malignant tumors, stomach cancer, liver cancer, pancreatic cancer, lung cancer, corpus uteri, ovary cancer, prostate cancer, testicular cancer, renal cancer, brain/cns cancer, throat cancer, skin melanoma, acute lymphocytic leukemia, acute myelogenous leukemia, Ewing's Sarcoma, Kaposi's Sarcoma, basal cell carinoma and squamous cell carcinoma, small cell lung cancer, choriocarcinoma, rhabdomyosarcoma, angiosarcoma, hemangioendothelioma, Wilms Tumor, neuroblastoma, mouth/pharynx cancer, esophageal cancer, larynx cancer, lymphoma, neurofibromatosis, tuberous sclerosis, hemangiomas, and lymphangiogenesis.

In various embodiments, the disease or disorder associated with methionine aminopeptidase is a skin disorder.

In a further embodiment, the disease or disorder is psoriasis, acne, rosacea, warts, eczema, hemangiomas, lymphangiogenesis, Sturge-Weber syndrome, venous ulcers of the skin, neurofibromatosis, and tuberous sclerosis.

In other embodiments, the disease or disorder associated with methionine aminopeptidase is neovascularization.

In a further embodiment, the disease or disorder is diabetic retinopathy, retinopathy of prematurity, corneal graft rejection, neovascular glaucoma, retrolental fibroplasias, epidemic keratoconjunctivitis, vitamin A deficiency, contact lens overwear, atopic keratitis, superior limbic keratitis, pterygium keratitis sicca, Sjogren's, acne rosacea, phylectenulosis, syphilis, *Mycobacteria* infections, lipid degeneration, chemical burns, bacterial ulcers, fungal ulcers, herpes simplex infections, herpes zoster infections, protozoan infections, Kaposi's sarcoma, Mooren's ulcer, Terrien's marginal degeneration, marginal keratolysis, trauma, rheumatoid arthritis, systemic lupus, polyarteritis, Wegener's sarcoidosis, scleritis, Stevens-Johnson disease, pemphigoid, radial keratotomy, corneal graft rejection, macular edema, macular degeneration, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme disease, systemic lupus erythematosus, retinopathy of prematurity, Eales' disease, Behcet's disease, infections causing a retinitis or choroiditis, presumed ocular histoplasmosis, Best's disease, myopia, optic pits, Stargardt's disease, pars planitis, chronic retinal detachment, hyperviscosity syndromes, toxoplasmosis, trauma and post-laser complications, and diseases associated with rubeosis (neovascularization of the ankle).

In other embodiments, the disease or disorder associated with methionine aminopeptidase is inflammatory and arthritic disease.

In a further embodiment, the disease or disorder is: rheumatoid arthritis, osteoarthritis, lupus, scleroderma, Crohn's disease, ulcerative colitis, psoriasis, sarcoidosis, Sarcoidosis, skin lesions, hemangiomas, Osler-Weber-Rendu disease, hereditary hemorrhagic telangiectasia, and osteoarthritis.

In certain aspects, the invention provides a method of inhibiting or reducing methionine aminopeptidase in a subject, the method comprising the step of administering to the subject an effective amount of a compound of formula I:

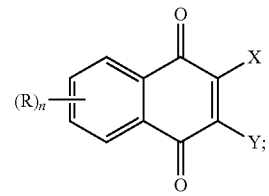

(I)

or a pharmaceutically acceptable salt thereof,
wherein,

R is H, hydroxy, nitro, halo, an optionally substituted alkyl, an optionally substituted cycloalkyl, an optionally substituted alkenyl, an optionally substituted aryl, an optionally substituted heteroaryl, optionally substituted heterocycloalkyl, $OR_B$, or $NR_AR_B$;

X is H, halo, nitro, halo, hydroxy, an optionally substituted alkyl, an optionally substituted cycloalkyl, an optionally substituted aryloxy, an optionally substituted alkenyl, an optionally substituted aryl, an optionally substituted heteroaryl, optionally substituted heterocycloalkyl, $C(O)OR_B$, $C(O)R_A$, $OR_B$, $NR_AR_B$, $NR_AC(O)R_A$, or $SO_3R_A$;

Y is H, halo, nitro, halo, hydroxy, an optionally substituted alkyl, an optionally substituted cycloalkyl, an optionally substituted aryloxy, an optionally substituted alkenyl, an optionally substituted aryl, an optionally substituted heteroaryl, optionally substituted heterocycloalkyl, $C(O)OR_B$, $C(O)R_A$, $OR_B$, $NR_AR_B$, $NR_AC(O)R_A$, or $SO_3R_A$;

each $R_A$ is independently H, OH, halo, an optionally substituted alkyl, or an optionally substituted aryl;

each $R_B$ is independently H, optionally substituted alkyl, optionally substituted aralkyl, or optionally substituted aryl; and n is 1, 2, or 3;

formula II:

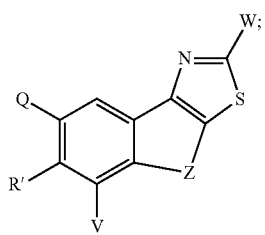

(II)

or a pharmaceutically acceptable salt thereof,
wherein,

Z is absent, $(CR_BR_C)_m$, $O(CR_BR_C)_m$, or $NR_D(CR_BR_C)_m$;

W is $NR_DR_D$, $NR_DC(O)R_D$, $N=C(R_E)$alkyl, $N=C(R_E)$aryl, $N=C(R_E)$heteroaryl, $N=C(R_E)$aralkyl, or $NR_DCR_B=N-OH$;

R' is H, hydroxy, nitro, halo, an optionally substituted alkyl, an optionally substituted cycloalkyl, an optionally substituted alkenyl, an optionally substituted aryl, an optionally substituted heteroaryl, optionally substituted heterocycloalkyl, $OR_B$, or $NR_AR_B$;

Q is H, halo, nitro, halo, hydroxy, an optionally substituted alkyl, an optionally substituted cycloalkyl, an optionally substituted aryloxy, an optionally substituted alkenyl, an optionally substituted aryl, an optionally substituted heteroaryl, optionally substituted heterocycloalkyl, $C(O)OR_B$, $C(O)R_A$, $OR_B$, $NR_AR_B$, $NR_AC(O)R_A$, or $SO_3R_A$; or R' and Q, together with the atoms to which each is attached, forms a cycloalkyl, heterocycloalkyl, aryl, or heteroaryl, each of which is optionally substituted;

V is H, halo, nitro, halo, hydroxy, an optionally substituted alkyl, an optionally substituted cycloalkyl, an optionally substituted aryloxy, an optionally substituted alkenyl, an optionally substituted aryl, an optionally substituted heteroaryl, optionally substituted heterocycloalkyl, $C(O)OR_B$, $C(O)R_A$, $OR_B$, $NR_AR_B$, $NR_AC(O)R_A$, or $SO_3R_A$;

each $R_B$ is independently H, optionally substituted alkyl, optionally substituted aralkyl, or optionally substituted aryl;

each $R_C$ is independently H, optionally substituted alkyl, optionally substituted aralkyl, or optionally substituted aryl;

each $R_D$ is independently H, optionally substituted alkyl, optionally substituted aralkyl, optionally substituted heteroaralkyl, or optionally substituted aryl;

each $R_E$ is independently H, optionally substituted alkyl, optionally substituted aralkyl, optionally substituted heteroaralkyl, or optionally substituted aryl; and each $R_A$ is independently H, OH, halo, an optionally substituted alkyl, or an optionally substituted aryl; or formula III:

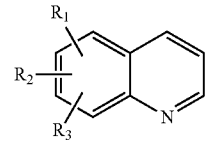

(III)

or a pharmaceutically acceptable salt thereof,
wherein, $R_1$ is H, hydroxy, nitro, halo, an optionally substituted alkyl, an optionally substituted cycloalkyl, an optionally substituted alkenyl, an optionally substituted aryl, an optionally substituted heteroaryl, optionally substituted heterocycloalkyl, $OR_B$, or $NR_AR_B$;

$R_2$ is H, hydroxy, nitro, halo, an optionally substituted alkyl, an optionally substituted cycloalkyl, an optionally substituted alkenyl, an optionally substituted aryl, an optionally substituted heteroaryl, optionally substituted heterocycloalkyl, $OR_B$, or $NR_AR_B$;

$R_3$ is $OR_B$ or $NR_AR_B$; or $R_2$ and $R_3$, together with the atoms to which each is attached, may form an optionally substituted heterocyclic or an optionally substituted heteroaryl;

each $R_A$ is independently H, OH, halo, an optionally substituted alkyl, or an optionally substituted aryl, $C(O)NR_BR_B$, or $C(O)R_B$; and each $R_B$ is independently H, optionally substituted alkyl, optionally substituted aralkyl, or optionally substituted aryl;

wherein said compound is identified in a screening assay.

In one embodiment, the screening assay is selected from MetAP enzyme assay, Double Thymidine synchronization, Cell cycle analysis, and siRNA Transfection, and $^3$H-thymidine incorporation assay. In a further embodiment, the screening assay is selected from MetAP enzyme assay and $^3$H-thymidine incorporation assay. In another further embodiment, the inhibitor has a $IC_{50}$ for inhibiting type 2 methionine aminopeptidase less than about 5 micromolar.

In one embodiment, the invention provides any method as described above, wherein the compound is a compound of formula I:

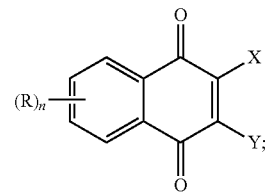

(I)

or a pharmaceutically acceptable salt thereof,
wherein,

R is H, hydroxy, nitro, halo, an optionally substituted alkyl, an optionally substituted alkenyl, an optionally substituted cycloalkyl, an optionally substituted aryl, an optionally substituted heteroaryl, optionally substituted heterocycloalkyl, OR$_B$, or NR$_A$R$_B$;

X is H, halo, nitro, hydroxy, an optionally substituted alkyl, an optionally substituted cycloalkyl, an optionally substituted aryloxy, an optionally substituted alkenyl, an optionally substituted aryl, an optionally substituted heteroaryl, optionally substituted heterocycloalkyl, C(O)OR$_B$, C(O)R$_A$, OR$_B$, NR$_A$, OR$_B$, NR$_A$C(O)R$_A$, or SO$_3$R$_A$;

Y is H, halo, nitro, halo, hydroxy, an optionally substituted alkyl, an optionally substituted cycloalkyl, an optionally substituted aryloxy, an optionally substituted alkenyl, an optionally substituted aryl, an optionally substituted heteroaryl, optionally substituted heterocycloalkyl, C(O)OR$_B$, C(O)R$_A$, OR$_B$, NR$_A$R$_B$, NR$_A$C(O)R$_A$, or SO$_3$R$_A$;

each R$_A$ is independently H, OH, halo, an optionally substituted alkyl, or an optionally substituted aryl;

each R$_B$ is independently H, optionally substituted alkyl, optionally substituted aralkyl, or optionally substituted aryl; and n is 1, 2, or 3.

In a further embodiment, X is H, Cl, Br, F, methyl, ethyl, propyl, i-propyl, butyl, s-butyl, t-butyl, OH, NH$_2$, O-Ph, NH(alkyl), NH(aryl), NHCO(aryl), C(O)OH, piperidyl, phthaloyl, imidazolyl; furanyl; thiophenyl (or thienyl or thiofuranyl); pyrazolyl; oxazolyl; isoxazolyl; thiazolyl; 1,2,3-, 1,2,4-, 1,2,5-, and 1,3,4-oxadiazolyl; isothiazolyl; pyridinyl; pyrazinyl; pyrimidinyl; pyridazinyl; 1,3,5-, 1,2,4-, 1,2,3-triazinyl; benzothiofuranyl, isobenzothiofuranyl, benzisoxazolyl, benzoxazolyl, purinyl, anthranilyl; quinolinyl; isoquinolinyl; benzoxazinyl; [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, tetrahydrofuryl, furanyl, dihydrofuranyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiodiazolyl, oxathiazolyl, oxadiazoly, pyranyl, dihydropyranyl, pyridinyl, piperidinyl, pyridazinyl, pyrimidinyl, pyrazinyl, piperazinyl, triazinyl, isoxazinyl, oxazolidinyl, isoxazolidinyl, oxathiazinyl, oxadiazinyl, morpholinyl, azepinyl, oxepinyl, thiepinyl, diazepinyl, naphthyridinyl, thiazolpyrimidinyl, thienopyrimidinyl, pyrimidopyrimidinyl, or pyridopyrimidinyl; each of which may be optionally substituted.

In another further embodiment, Y is H, Cl, Br, F, methyl, ethyl, propyl, i-propyl, butyl, s-butyl, t-butyl, phythyl, OH, NH$_2$, O-Ph, NH(alkyl), NH(aryl), NHCO(aryl), C(O)OH, piperidyl, phthaloyl, imidazolyl; furanyl; thiophenyl (or thienyl or thiofuranyl); pyrazolyl; oxazolyl; isoxazolyl; thiazolyl; 1,2,3-, 1,2,4-, 1,2,5-, and 1,3,4-oxadiazolyl; isothiazolyl; pyridinyl; pyrazinyl; pyrimidinyl; pyridazinyl; 1,3,5-, 1,2,4-, 1,2,3-triazinyl; benzothiofuranyl, isobenzothiofuranyl, benzisoxazolyl, benzoxazolyl, purinyl, anthranilyl; quinolinyl; isoquinolinyl; benzoxazinyl; [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, tetrahydrofuryl, furanyl, dihydrofuranyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiodiazolyl, oxathiazolyl, oxadiazoly, pyranyl, dihydropyranyl, pyridinyl, piperidinyl, pyridazinyl, pyrimidinyl, pyrazinyl, piperazinyl, triazinyl, isoxazinyl, oxazolidinyl, isoxazolidinyl, oxathiazinyl, oxadiazinyl, morpholinyl, azepinyl, oxepinyl, thiepinyl, diazepinyl, naphthyridinyl, thiazolpyrimidinyl, thienopyrimidinyl, pyrimidopyrimidinyl, or pyridopyrimidinyl; each of which may be optionally substituted.

In another embodiment, the invention provides any method as described above, wherein the compound is a compound of formula I-A:

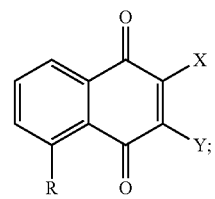

(I-A)

or a pharmaceutically acceptable salt thereof,
wherein,

R is H or hydroxy;

X is H, Cl, Br, F, methyl, OH, NH$_2$, O-Ph, NH(alkyl), NH(aryl), NHCO(aryl), C(O)OH, piperidyl, or phthaloyl, each of which may be optionally substituted; and Y is H, Cl, Br, F, methyl, phythyl, OH, NH$_2$, O-Ph, NH(alkyl), NH(aryl), NHCO(aryl), C(O)OH, piperidyl, or phthaloyl, each of which may be optionally substituted.

In another embodiment, the invention provides any method as described above, wherein the compound is a compound of formula II:

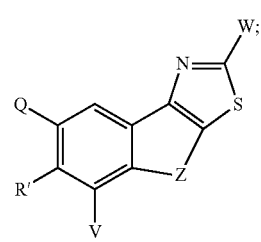

(II)

or a pharmaceutically acceptable salt thereof,
wherein,

Z is absent, (CR$_B$R$_C$)$_m$, O(CR$_B$R$_C$)$_m$, or NR$_D$(CR$_B$R$_C$)$_m$;

W is NR$_D$R$_D$, NR$_D$C(O)R$_D$, N═C(R$_E$)alkyl, N═C(R$_E$)aryl, N═C(R$_E$)heteroaryl, N═C(R$_E$)aralkyl, or NR$_D$CR$_B$═N—OH;

R' is H, hydroxy, nitro, halo, an optionally substituted alkyl, an optionally substituted cycloalkyl, an optionally substituted alkenyl, an optionally substituted aryl, an optionally substituted heteroaryl, optionally substituted heterocycloalkyl, OR$_B$, or NR$_A$R$_B$;

Q is H, halo, nitro, halo, hydroxy, an optionally substituted alkyl, an optionally substituted cycloalkyl, an optionally substituted aryloxy, an optionally substituted alkenyl, an optionally substituted aryl, an optionally substituted heteroaryl, optionally substituted heterocycloalkyl, C(O)OR$_B$, C(O)R$_A$, OR$_B$, NR$_A$R$_B$, NR$_A$C(O)R$_A$, or SO$_3$R$_A$; or R' and Q, together with the atoms to which each is attached, forms a cycloalkyl, heterocycloalkyl, aryl, or heteroaryl, each of which is optionally substituted;

V is H, halo, nitro, halo, hydroxy, an optionally substituted alkyl, an optionally substituted cycloalkyl, an optionally substituted aryloxy, an optionally substituted alkenyl, an optionally substituted aryl, an optionally substituted heteroaryl, optionally substituted heterocycloalkyl, $C(O)OR_B$, $C(O)R_A$, $OR_B$, $NR_AR_B$, $NR_AC(O)R_A$, or $SO_3R_A$;

each $R_B$ is independently H, optionally substituted alkyl, optionally substituted aralkyl, or optionally substituted aryl;

each $R_C$ is independently H, optionally substituted alkyl, optionally substituted aralkyl, or optionally substituted aryl;

each $R_D$ is independently H, optionally substituted alkyl, optionally substituted aralkyl, optionally substituted heteroaralkyl, or optionally substituted aryl;

each $R_E$ is independently H, optionally substituted alkyl, optionally substituted aralkyl, optionally substituted heteroaralkyl, or optionally substituted aryl; and each $R_A$ is independently H, OH, halo, an optionally substituted alkyl, or an optionally substituted aryl.

In a further embodiment, the invention provides any method as described above, wherein the compound is compound of formula II-A:

(II-A)

or a pharmaceutically acceptable salt thereof,
wherein,

W is $NR_DR_D$, $NR_DC(O)R_D$, $N=C(R_E)$alkyl, $N=C(R_E)$aryl, $N=C(R_E)$heteroaryl, $N=C(R_E)$aralkyl, or $NR_DCR_B=N-OH$;

R' is H or $OR_B$;

Q is H or $OR_B$; or

R' and Q, together with the atoms to which each is attached, forms a heterocycloalkyl, which is optionally substituted;

V is H or $OR_B$;

each $R_B$ is independently H, optionally substituted alkyl, optionally substituted aralkyl, optionally substituted heteroaralkyl, or optionally substituted aryl;

each $R_D$ is independently H, optionally substituted alkyl, optionally substituted aralkyl, optionally substituted heteroaralkyl, or optionally substituted aryl; and each $R_E$ is independently H, optionally substituted alkyl, optionally substituted aralkyl, optionally substituted heteroaralkyl, or optionally substituted aryl.

In another embodiment, the invention provides any method as described above, wherein the compound is compound of formula II-B:

(II-B)

or a pharmaceutically acceptable salt thereof,
wherein,

W is $NR_DR_D$, $NR_DC(O)R_D$, $N=C(R_E)$alkyl, $N=C(R_E)$aryl, $N=C(R_E)$heteroaryl, $N=C(R_E)$aralkyl, or $NR_DCR_B=N-OH$;

R' is H or $OR_B$;

Q is H or $OR_B$; or

R' and Q, together with the atoms to which each is attached, forms a heterocycloalkyl, which is optionally substituted;

V is H or $OR_B$;

each $R_B$ is independently H, optionally substituted alkyl, optionally substituted aralkyl, or optionally substituted aryl;

each $R_C$ is independently H, optionally substituted alkyl, optionally substituted aralkyl, or optionally substituted aryl;

each $R_D$ is independently H, optionally substituted alkyl, optionally substituted aralkyl, optionally substituted heteroaralkyl, or optionally substituted aryl; and each $R_E$ is independently H, optionally substituted alkyl, optionally substituted aralkyl, optionally substituted heteroaralkyl, or optionally substituted aryl.

In another embodiment, the invention provides any method as described above, wherein the compound is a compound of formula II-C:

(II-C)

or a pharmaceutically acceptable salt thereof,
wherein,

W is $NR_DR_D$, $NR_DC(O)R_D$, $N=C(R_E)$alkyl, $N=C(R_E)$aryl, $N=C(R_E)$heteroaryl, $N=C(R_E)$aralkyl, or $NR_DCR_B=N-OH$;

R' is H or $OR_B$;

Q is H or $OR_B$; or

R' and Q, together with the atoms to which each is attached, forms a heterocycloalkyl, which is optionally substituted;

V is H or $OR_B$;

each $R_B$ is independently H, optionally substituted alkyl, optionally substituted aralkyl, or optionally substituted aryl;

each $R_D$ is independently H, optionally substituted alkyl, optionally substituted aralkyl, optionally substituted heteroaralkyl, or optionally substituted aryl; and each $R_E$ is independently H, optionally substituted alkyl, optionally substituted aralkyl, optionally substituted heteroaralkyl, or optionally substituted aryl.

In certain embodiments, the invention provides any method as described above, wherein the compound is a compound of formula III:

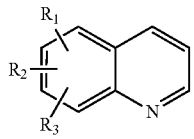

(III)

or a pharmaceutically acceptable salt thereof,
wherein, $R_1$ is H, hydroxy, nitro, halo, an optionally substituted alkyl, an optionally substituted cycloalkyl, an optionally substituted alkenyl, an optionally substituted aryl, an optionally substituted heteroaryl, optionally substituted heterocycloalkyl, $OR_B$, or $NR_AR_B$;

$R_2$ is H, hydroxy, nitro, halo, an optionally substituted alkyl, an optionally substituted cycloalkyl, an optionally substituted alkenyl, an optionally substituted aryl, an optionally substituted heteroaryl, optionally substituted heterocycloalkyl, $OR_B$, or $NR_AR_B$;

$R_3$ is $OR_B$ or $NR_AR_B$; or $R_2$ and $R_3$, together with the atoms to which each is attached, may form an optionally substituted heterocyclic or an optionally substituted heteroaryl;

each $R_A$ is independently H, OH, halo, an optionally substituted alkyl, or an optionally substituted aryl, C(O)$NR_BR_B$, or C(O)$R_B$;

each $R_A$ is independently H, OH, halo, an optionally substituted alkyl, or an optionally substituted aryl; and each $R_B$ is independently H, optionally substituted alkyl, optionally substituted aralkyl, or optionally substituted aryl.

In a further embodiment, the invention provides any method as described above, wherein the compound is a compound of formula III-A:

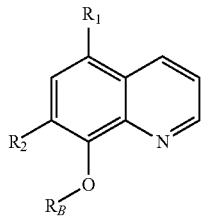

(III-A)

or a pharmaceutically acceptable salt thereof,
wherein, $R_1$ is H or halo;

$R_2$ is H, halo, or an optionally substituted alkyl;

$R_3$ is $OR_B$ or $NR_AR_B$; or $R_2$ and $R_3$, together with the atoms to which each is attached, may form an optionally substituted heterocyclic or an optionally substituted heteroaryl;

each $R_A$ is independently H, OH, halo, an optionally substituted alkyl, or an optionally substituted aryl, C(O)$NR_BR_B$, or C(O)$R_B$; and each $R_B$ is independently H, optionally substituted alkyl, optionally substituted aralkyl, or optionally substituted aryl.

In various embodiments, the invention provides any method as described above, further comprising an additional therapeutic agent.

In a further embodiment, the additional therapeutic agent is a methionine aminopeptidase inhibiting compound.

In a further embodiment, the additional therapeutic agent is an anti-tuberculosis compound.

In a further embodiment, the additional therapeutic agent is an anti-bacterial compound.

In another embodiment, the invention provides any method as described above, wherein the step of administering the compound comprises administering the compound orally, topically, parentally, intravenously or intramuscularly.

In certain embodiments, the step of administering the compound comprises administering the compound in a dosage of between about 0.1 and 120 mg/kg/day.

In other embodiments, the step of administering the compound comprises administering the compound in a dosage of less than about 500 mg/day.

In various embodiments, the invention provides any method as described above wherein the subject is a human.

In another aspect, the invention provides for the use of a compound in the manufacture of a medicament for inhibiting type 2 methionine aminopeptidase in a patient, wherein the compound is a compound of formula I, formula II, or formula III.

The following demonstrates that MtMetAP1a is an anti-tuberculosis target using a combination of chemical and genetic approaches. The two MtMetAPs from *E. coli* were overexpressed and purified to near homogeneity and showed that both MtMetAPs are functional as methionine aminopeptidases in vitro. Using a high-throughput screening approach, 175,000 compounds were screened against MtMetAP1c and identified 1,4-napthoquinone class of compounds as potent inhibitors that were active in both MtMetAP enzymatic assays and mycobacterial culture. Other classes of compounds identified by the screens included hydroxyquinolines and naphthothiazoles. In addition, MtMetAPs were validated as the relevant targets of the newly discovered inhibitors of *M. tuberculosis* in vivo.

A combination of chemical and genetic approaches were applied to investigate the functions of two isoforms of MtMetAP and gathered strong evidence that MtMetAP1a is essential for the viability of *M. tuberculosis* and a promising target for developing anti-TB agents. In addition, we also identified naphthoquinones as an active pharmacophore for developing inhibitors of MtMetAP1. Inhibition of MtMetAP1a by either small molecule inhibitors or through the expression of anti-sense RNA led to significant inhibition of the growth of *M. tuberculosis* in culture, supporting the notion that MtMetAP1a plays an essential role in *M. tuberculosis* and can serve as a target for small molecule inhibitors.

Based on genomic sequences available to date, *M. tuberculosis* possesses two MetAP encoding genes, in contrast to most other prokaryotes that only harbor a single gene for MetAP enzyme. We sought to unravel the similarities and differences in the biochemical properties and cellular functions of the two enzymes. Of the two MtMetAP1 enzymes, MtMetAP1c contains an N-terminal "linker" region while MtMetAP1a is free of the N-terminal domain similar to other prokaryotic MetAP enzymes (FIG. 1). Using nearly homogeneous recombinant proteins, we found that MtMetAP1a is catalytically tenfold less active than MtMetAP1c. It remains unclear whether this difference in activity is due to the use of the artificial dipeptide substrate which significantly deviates from the substrate preference of MtMetAP1a. In addition, we also observed some difference in thermostability, optimal pH and dependence on metal ions. In comparison with MtMetAP1c, MtMetAP1a has a lower optimal temperature, a broader range of optimal pH values spanning one unit of pH and a higher threshold of activation by metal ions. While MtMetAP1c contains an N-terminal SH3 ligand-containing extension, MtMetAP1a contains an internal insertion of about six amino acids in comparison with both MtMetAP1c and *E. coli* MetAP. These differences in primary structure and the accompanying tertiary structures may account for part of the differences in activity, substrate specificity and other biochemical properties of the two MtMetAPs.

The unique presence of two isoforms of MetAP enzymes in TB in contrast to the majority of other prokaryotes called into question whether one or both isoforms are essential for the viability of the mycobacteria. To assess this question, we performed a high-throughput screen against MtMetAP1c and identified a family of structurally related inhibitors sharing a common 1,4-napthoquinone core. Although evaluation of additional structural analogs led to the identification of more potent inhibitors of MtMetAP1c, none of the inhibitors of this structural class are selective towards either MtMetAP1c or MtMetAP1a. The lack of specificity was further shown by the demonstration that overexpression of either MtMetAP conferred resistance to the inhibitor used. The non-selective MtMetAP inhibitors were capable of inhibiting the growth of *M. tuberculosis*, suggesting that either or both MtMetAP enzymes are essential for bacterial growth, leaving unanswered the question of whether the growth inhibition was mediated through one or both isoforms of MtMetAP. Using knockdown with specific antisense RNA, we found that the two MtMetAP enzymes are not functionally redundant. Knockdown of MtMetAP1a, rather than MtMetAP1c, caused inhibition of proliferation of *M. tuberculosis* in culture, suggesting that inhibition of MtMetAP1a is likely to be responsible for the growth inhibition by the MtMetAP inhibitors.

DEFINITIONS

Listed below are definitions of various terms used to describe this invention. These definitions apply to the terms as they are used throughout this specification and claims, unless otherwise limited in specific instances, either individually or as part of a larger group. The number of carbon atoms in a substituent can be indicated by the prefix "$C_x$—$C_y$," where x is the minimum and y is the maximum number of carbon atoms in the substituent. Likewise, a $C_x$ chain means a chain containing, x carbon atoms.

The prefix "halo" indicates that the substituent to which the prefix is attached is substituted with one or more independently selected halogen radicals. For example, "$C_1$-$C_6$ haloalkyl" means a $C_1$-$C_6$ alkyl substituent wherein at least one hydrogen radical is replaced with a halogen radical.

If a linking element in a depicted structure is "absent", or a "bond", then the left element in the depicted structure is directly linked to the right element in the depicted structure. For example, if a chemical structure is depicted as X-(L)$_n$-Y wherein L is absent or n is 0, then the chemical structure is X—Y.

The term "alkyl" as used herein, refers to a saturated, straight- or branched-chain hydrocarbon radical. For example, "$C_1$-$C_8$ alkyl" contains from one to eight carbon atoms. Examples of alkyl radicals include, but are not limited to, methyl, ethyl, propyl, isopropyl, n-butyl, tert-butyl, neopentyl, n-hexyl, heptyl, octyl radicals and the like.

The term "alkenyl" as used herein, denotes a straight- or branched-chain hydrocarbon radical containing one or more double bonds. For example, "$C_2$-$C_8$ alkenyl" contains from two to eight carbon atoms. Alkenyl groups include, but are not limited to, for example, ethenyl, propenyl, butenyl, 1-methyl-2-buten-1-yl, heptenyl, octenyl and the like.

The term "alkynyl" as used herein, denotes a straight- or branched-chain hydrocarbon radical containing one or more triple bonds. For example, "$C_2$-$C_8$ alkynyl" contains from two to eight carbon atoms. Representative alkynyl groups include, but are not limited to, for example, ethynyl, 1-propynyl, 1-butynyl, heptynyl, octynyl and the like.

The terms "carbocycle", "carbocyclic", "carbocyclyl", or "cycloalkyl" refer to a saturated (e.g., "cycloalkyl"), partially saturated (e.g., "cycloalkenyl" or "cycloalkynyl") or completely unsaturated (e.g., "aryl") ring system containing zero heteroatom ring atom. A carbocyclyl may be, without limitation, a single ring, or two or more fused rings, or bridged or spiro rings. A carbocyclyl may contain, for example, from 3 to 10 ring members (i.e., $C_3$-$C_{10}$ carbocyclyl, such as $C_3$-$C_{10}$ cycloalkyl). A substituted carbocyclyl may have either cis or trans geometry. Representative examples of carbocyclyl groups include, but are not limited to, cyclopropyl, cyclobutyl, cyclopentyl, cyclohexyl, cycloheptyl, cyclooctyl, cyclopentenyl, cyclopentadienyl, cyclohexadienyl, adamantyl, decahydro-naphthalenyl, octahydro-indenyl, cyclohexenyl, phenyl, naphthyl, fluorenyl, indanyl, 1,2,3,4-tetrahydro-naphthyl, indenyl, isoindenyl, bicyclodecanyl, anthracenyl, phenanthrenyl, benzonaphthenyl (also known as "phenalenyl"), decalinyl, and norpinanyl and the like. A carbocyclyl group can be attached to the parent molecular moiety through any substitutable carbon atom of the group. The term "cycloalkyl" denotes a monovalent group derived from a monocyclic or polycyclic saturated carbocyclic ring compound. Examples of cycloalkyl include, but not limited to, cyclopropyl, cyclobutyl, cyclopentyl, cyclohexyl, bicyclo [2.2.1] heptyl, and bicyclo [2.2.2] octyl and the like.

The term "aryl" refers to an aromatic carbocyclyl containing from 6 to 14 carbon ring atoms. Non-limiting examples of aryls include phenyl, naphthalenyl, anthracenyl, and indenyl and the like. An aryl group can be connected to the parent molecular moiety through any substitutable carbon atom of the group.

The term "heteroaryl" means an aromatic heterocyclyl typically containing from 5 to 18 ring atoms. A heteroaryl may be a single ring, or two or more fused rings. Non-limiting examples of five-membered heteroaryls include imidazolyl; furanyl; thiophenyl (or thienyl or thiofuranyl); pyrazolyl; oxazolyl; isoxazolyl; thiazolyl; 1,2,3-, 1,2,4-, 1,2,5-, and 1,3,4-oxadiazolyl; and isothiazolyl. Non-limiting examples of six-membered heteroaryls include pyridinyl; pyrazinyl; pyrimidinyl; pyridazinyl; and 1,3,5-, 1,2,4-, and 1,2,3-triazinyl. Non-limiting examples of 6/5-membered fused ring heteroaryls include benzothiofuranyl, isobenzothiofuranyl, benzisoxazolyl, benzoxazolyl, purinyl, and anthranilyl. Non-limiting examples of 6/6-membered fused ring heteroaryls include quinolinyl; isoquinolinyl; and benzoxazinyl (including cinnolinyl and quinazolinyl).

The term "heterocycloalkyl" refers to a non-aromatic 3-, 4-, 5-, 6- or 7-membered ring or a bi- or tri-cyclic group fused system, where at least one of the ring atoms is a heteroatom, and where (i) each 5-membered ring has 0 to 1 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above rings may be fused to a benzene ring. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl and the like.

The terms "heterocyclic" or "heterocycle" or "heterocyclyl" refer to a saturated (e.g., "heterocycloalkyl"), partially unsaturated (e.g., "heterocycloalkenyl" or "heterocycloalkynyl") or completely unsaturated (e.g., "heteroaryl") ring system, where at least one of the ring atoms is a heteroatom (i.e., nitrogen, oxygen or sulfur), with the remaining ring atoms being independently selected from the group consisting of carbon, nitrogen, oxygen and sulfur. A heterocyclyl group can be linked to the parent molecular moiety via any substitutable carbon or nitrogen atom in the group, provided that a stable molecule results. A heterocyclyl may be, without limitation, a single ring. Non-limiting examples of single-ring heterocyclyls include furanyl, dihydrofuranyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiodiazolyl, oxathiazolyl, oxadiazolyl, pyranyl, dihydropyranyl, pyridinyl, piperidinyl, pyridazinyl, pyrimidinyl, pyrazinyl, piperazinyl, triazinyl, isoxazinyl, oxazolidinyl, isoxazolidinyl, oxathiazinyl, oxadiazinyl, morpholinyl, azepinyl, oxepinyl, thiepinyl, or diazepinyl. A heterocyclyl may also include, without limitation, two or more rings fused together, such as, for example, naphthyridinyl, thiazolopyrimidinyl, thienopyrimidinyl, pyrimidopyrimidinyl, or pyridopyrimidinyl. A heterocyclyl may comprise one or more sulfur atoms as ring members; and in some cases, the sulfur atom(s) is oxidized to SO or $SO_2$. The nitrogen heteroatom(s) in a heterocyclyl may or may not be quaternized, and may or may not be oxidized to N-oxide. In addition, the nitrogen heteroatom(s) may or may not be N-protected.

The terms "optionally substituted", "optionally substituted alkyl", "optionally substituted "optionally substituted alkenyl", "optionally substituted alkynyl", "optionally substituted carbocyclic", "optionally substituted aryl", "optionally substituted heteroaryl", "optionally substituted heterocyclic" and any other optionally substituted group as used herein, refer to groups that are substituted or unsubstituted by independent replacement of one, two, or three or more of the hydrogen atoms thereon with typical substituents including, but not limited to:

—F, —Cl, —Br, —I,
—OH, alkoxy, oxo, thiooxo,
—$NO_2$, —CN, $CF_3$, $N_3$,
—$NH_2$, —NH-alkyl, —NH-alkenyl, —NH-alkynyl, —NH-cycloalkyl, —NH-aryl, —NH-heteroaryl, —NH-heterocyclic, -dialkylamino, -diarylamino, -diheteroarylamino,
—O-alkyl, —O-alkenyl, —O-alkynyl, —O-cycloalkyl, —O-aryl, —O-heteroaryl, —O-heterocyclic,
—C(O)— alkyl, —C(O)— alkenyl, —C(O)— alkynyl, —C(O)— cycloalkyl, —C(O)-aryl, —C(O)-heteroaryl, —C(O)-heterocycloalkyl,
—$CONH_2$, —CONH— alkyl, —CONH— alkenyl, —CONH— alkynyl, —CONH— cycloalkyl, —CONH-aryl, —CONH-heteroaryl, —CONH-heterocycloalkyl,
—$OCO_2$— alkyl, —$OCO_2$— alkenyl, —$OCO_2$— alkynyl, —$OCO_2$— cycloalkyl, —$OCO_2$-aryl, —$OCO_2$-heteroaryl, —$OCO_2$-heterocycloalkyl, —$OCONH_2$, —OCONH— alkyl, —OCONH— alkenyl, —OCONH— alkynyl, —OCONH— cycloalkyl, —OCONH— aryl, —OCONH— heteroaryl, —OCONH-heterocycloalkyl, —NHC(O)— alkyl, —NHC(O)— alkenyl, —NHC(O)— alkynyl, —NHC(O)— cycloalkyl, —NHC(O)-aryl, —NHC(O)-heteroaryl, —NHC(O)-heterocycloalkyl, —$NHCO_2$— alkyl, —$NHCO_2$-alkenyl, —$NHCO_2$-alkynyl, —$NHCO_2$-cycloalkyl, —$NHCO_2$-aryl, —$NHCO_2$-heteroaryl, —$NHCO_2$-heterocycloalkyl, —$NHC(O)NH_2$, —NHC(O) NH-alkyl, —NHC(O)NH-alkenyl, —NHC(O)NH-alkenyl, —NHC(O)NH-cycloalkyl, —NHC(O)NH-aryl, —NHC(O) NH-heteroaryl, —NHC(O)NH-heterocycloalkyl, NHC(S) $NH_2$, —NHC(S)NH-alkyl, —NHC(S)NH-alkenyl, —NHC(S)NH-alkynyl, —NHC(S)NH-cycloalkyl, —NHC(S)NH-aryl, —NHC(S)NH-heteroaryl, —NHC(S)NH-heterocycloalkyl, —$NHC(NH)NH_2$, —NHC(NH)NH-alkyl, —NHC(NH)NH-alkenyl, —NHC(NH)NH-alkenyl, —NHC(NH)NH-cycloalkyl, —NHC(NH)NH-aryl, —NHC(NH) NH-heteroaryl, —NHC(NH)NH-heterocycloalkyl, —NHC(NH)-alkyl, —NHC(NH)-alkenyl, —NHC(NH)-alkenyl, —NHC(NH)-cycloalkyl, —NHC(NH)-aryl, —NHC(NH)-heteroaryl, —NHC(NH)-heterocycloalkyl, —C(NH)NH-alkyl, —C(NH)NH-alkenyl, —C(NH)NH-alkynyl, —C(NH)NH-cycloalkyl, —C(NH)NH-aryl, —C(NH)NH-heteroaryl, —C(NH)NH-heterocycloalkyl, —S(O)-alkyl, —S(O)-alkenyl, —S(O)-alkynyl, —S(O)-cycloalkyl, —S(O)-aryl, —S(O)-heteroaryl, —S(O)-heterocycloalkyl —$SO_2NH_2$, —$SO_2$NH-alkyl, —$SO_2$NH-alkenyl, —$SO_2$NH-alkynyl, —$SO_2$NH-cycloalkyl, —$SO_2$NH-aryl, —$SO_2$NH-heteroaryl, —$SO_2$NH-heterocycloalkyl, —$NHSO_2$-alkyl, —$NHSO_2$-alkenyl, —$NHSO_2$-alkynyl, —$NHSO_2$-cycloalkyl, —$NHSO_2$-aryl,
—$NHSO_2$-heteroaryl, —$NHSO_2$-heterocycloalkyl,
—$CH_2NH_2$, —$CH_2SO_2CH_3$, -alkyl, -alkenyl, -alkynyl, -aryl, -arylalkyl, -heteroaryl, -heteroarylalkyl, -heterocycloalkyl, -cycloalkyl, -carbocyclic, -heterocyclic, polyalkoxyalkyl, polyalkoxy, -methoxymethoxy, -methoxyethoxy, —SH, —S-alkyl, —S-alkenyl, —S-alkynyl, —S-cycloalkyl, —S-aryl, —S-heteroaryl, —S-heterocycloalkyl, or methylthiomethyl.

It is understood that the aryls, heteroaryls, carbocycles, heterocycles, alkyls, and the like can be further substituted.

The terms "hal," "halo" and "halogen," as used herein, refer to an atom selected from fluorine, chlorine, bromine and iodine.

The term "subject" as used herein refers to a mammal. A subject therefore refers to, for example, dogs, cats, horses, cows, pigs, guinea pigs, and the like. Preferably the subject is a human. When the subject is a human, the subject may be either a patient or a healthy human.

The term "alkylamino" refers to a group having the structure —$N(R_aR_b)$, where $R_a$ and $R_b$ are independently H or alkyl.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in *J. Pharmaceutical Sciences*, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts, or salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, or magnesium salts, and the like. Further pharmaceutically acceptable salts include, when appropriate, nontoxic ammonium, quaternary ammonium, and ammonium ions formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to afford any compound delineated by the formulae of the instant invention. Various forms of prodrugs are known in the art, for example, as discussed in Bundgaard, (ed.), Design of Prodrugs, Elsevier (1985); Widder, et al. (ed.), *Method. Enzymol.* vol. 4, Academic Press (1985); Krogsgaard-Larsen, et al., (ed). "Design and Application of Prodrugs, Textbook of Drug Design and Development, Chapter 5, 113-191 (1991); Bundgaard, et al., *Adv. Drug Deliver. Rev.* 8:1-38 (1992); Bundgaard, *J. Pharm. Sci.* 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism Chemistry, Biochemistry And Enzymology," John Wiley and Sons, Ltd. (2002).

This invention also encompasses pharmaceutical compositions containing, and methods of treating viral infections through administering, pharmaceutically acceptable prodrugs of compounds of the invention. For example, compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxylysine, desmosine, isodesmosine, 3-methylhistidine, norvalin, β-alanine, γ-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxy carbonyls, as outlined in *Adv. Drug Deliver. Rev.* 1996, 19: 1-15. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups, and elixirs. In addition to the active compounds, the liquid dosage forms may contain inert diluents commonly used in the art such as, for example, water, alcohol or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, polysorbate, dimethylformamide, oils (in particular, cottonseed, groundnut, corn, germ, olive, castor, and sesame oils), mono- or diglycerides, glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, antioxidants, sweetening, flavoring, and perfuming agents. The liquid dosage form can also be encapsulated in a gelatin capsule, wherein a compound of the present invention can be dissolved in a pharmaceutically acceptable carrier containing, for example, one or more solubilizating agents (e.g., polysorbate 80 and mono and diglycerides), and other suitable excipients (e.g., an antioxidants such as ascorbyl palmitate, or a sweetening or flavoring agent).

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Immediate release forms are also contemplated by the present invention.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above The solid dosage forms of tablets, dragés, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Preferably, a compound of the invention is formulated in a solid dispersion, where the compound can be molecularly dispersed in a matrix which comprises a pharmaceutically acceptable, hydrophilic polymer. The matrix may also contain a pharmaceutically acceptable surfactant. Suitable solid dispersion technology for formulating a compound of the invention includes, but is not limited to, melt extrusion, spray drying, or solvent evaporation.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, viral infections are treated or prevented in a subject, such as a human or another animal, by administering to the subject a therapeutically effective amount of a compound of the invention (or a pharmaceutically acceptable salt, ester or prodrug thereof), in such amounts and for such time as is necessary to achieve the desired result. The term "therapeutically effective amount" of a compound of the invention, as used herein, means a sufficient amount of the compound so as to decrease the viral load in a subject and/or decrease the subject's HCV symptoms. As is well understood in the medical arts a therapeutically effective amount of a compound of this invention will be at a reasonable benefit/risk ratio applicable to any medical treatment.

An inhibitory amount or dose of the compounds of the present invention may range from about 0.1 mg/Kg to about 500 mg/Kg, alternatively from about 1 to about 50 mg/Kg. Inhibitory amounts or doses will also vary depending on route of administration, as well as the possibility of co-usage with other agents.

The term "effective amount" of a compound of the invention, as used herein, means a sufficient amount of the compound so as to decrease the viral load in a biological sample or in a subject. As well understood in the medical arts, an effective amount of a compound of this invention will be at a reasonable benefit/risk ratio applicable to any medical treatment.

The term "inhibitory amount" of a compound of the present invention means a sufficient amount to decrease the effect of a disorder in a biological sample or a subject. It is understood that when said inhibitory amount of a compound of the present invention is administered to a subject it will be at a reasonable benefit/risk ratio applicable to any medical treatment as determined by a physician. The term "biological sample(s)," as used herein, means a substance of biological origin, which may be intended for administration to a subject. Examples of biological samples include, but are not limited to, blood and components thereof such as plasma, platelets, subpopulations of blood cells and the like; organs such as kidney, liver, heart, lung, and the like; sperm and ova; bone marrow and components thereof; or stem cells. Thus, another embodiment of the present invention is a method of treating a biological sample by contacting said biological sample with an inhibitory amount of a compound or pharmaceutical composition of the present invention.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily inhibitory dose of the compounds of this invention administered to a subject in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In one embodiment, treatment regimens according to the present invention comprise administration to a patient in need of such treatment from about 10 mg to about 1000 mg of the compound(s) of this invention per day in single or multiple doses. In another embodiment, the treatment regimen comprises administration to a patient in need of such treatment from about 25 mg to about 6000 mg of a compound(s) of this invention per day in single or multiple doses. Preferably, a compound(s) of the present invention, or a combination of a compound(s) of the invention and another compound, is administered once daily or twice daily to achieve the desired daily dose amount. For instance, when used alone, a compound of the present invention can be administered to a patient twice a day with a total daily dose of 4000, 4200, 4400, 4600, 4800 or 5000 mg. For another instance, when used in combination with another compound, a compound of the present invention can be administered to a patient once or twice a day with a total daily dose of 200, 400, 600 or 800 mg, where the amount of ritonavir can be 25, 50 or 100 mg per administration.

Synthetic Methods

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present invention. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds of this invention may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

EXAMPLES

The compounds and processes of the present invention will be better understood in connection with the following examples, which are intended as an illustration only and not to limit the scope of the invention. The following examples can be prepared according to the schemes as described above, or according to the synthetic steps as described below. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

The chemical structures herein may contain certain —NH—, —NH$_2$ (amino) and —OH (hydroxyl) groups where the corresponding hydrogen atom(s) may not explicitly appear; however they are to be read as —NH—, —NH$_2$ or —OH as the case may be.

General Remarks on the Synthesis

Thin-layer chromatography (TLC) was performed on Analtech precoated silica gel HLF UV$_{254}$ Uniplates and were visualized using 254 nm UV light, or by staining with iodine, ceric ammonium molybdate stain. Silica gel (60-200 mesh, from Acros) was used for air-flashed chromatography. Reagents were purchased from Acros, TCI-America, or Aldrich companies. NMR data were collected on a Varian Unity-400 (400 MHz $^1$H, 100.6 MHz $^{13}$C) machine. $^1$H NMR spectra were obtained in CDCl$_3$, methanol-d$_4$, acetone-d$_6$ or DMSO-d$_6$ with tetramethylsilane (TMS, δ=0.00) or residual protanated solvent peak as an internal reference. $^{13}$C NMR spectra were proton decoupled and were recorded in CDCl$_3$, methanol-d$_4$, acetone-d$_6$ or DMSO-d$_6$ with tetramethylsilane (TMS, δ=0.00) or residual protanated solvent peak as an internal reference. Chemical shifts are reported in ppm (δ). Multiplicities are indicated by s (singlet), d (doublet), t (triplet), q (quartet), m (multiplet), dd (doublet of doublet), dt (doublet of triplet), br. (broad), app. (apparent) and exch. (exchangeable). Coupling constants, J, are reported in Hertz (Hz); integration is provided; and assignments of individual resonances are supported in most cases by the following NMR experiments: COSY, DEPT, or HMBC and HMQC. Data are presented in the form: chemical shift (multiplicity, coupling constants, integration and assignments where relevant). Low-resolution mass spectra were obtained on a Voyager DE-STR, MALDI-TOF instrument at the AB Mass Spectrometry/Proteomics Facility at the Johns Hopkins University. The MALDI-samples were prepared by mixing droplets of the sample solutions in chloroform or methanol and 2,5-dihydroxybenzoic acid solution in acetone, where the latter served as the matrix. Data are reported in the form m/z (% intensity, interpreted ionic species). The solvents used in reactions were reagent grade. The solvents used for extraction and chromatography were technical grade. The reactions were performed in oven-dried glassware.

Example 1:
2-bromo-3-(4-fluoro)phenoxy-naphthoquinone (10)

Sodium hydride (48 mg, 1.2 equiv.; 60% dispersion in mineral oil) was added at once to a solution of 4-fluorophenol (129 mg, 1.15 equiv.) in THF (20 mL) at 0° C. After stirring vigorously for 10 min. 2,3-dibromonaphthoquinone (316 mg, 1 equiv.) in THF (5 mL) was added and the reaction mixture was stirred at room temperature for an hour. The reaction mixture was quenched by adding saturated aqueous ammonium chloride (10 mL) and the mixture was extracted with EtOAc (2×20 mL). The organic layers were pooled, the solvent was evaporated and the crude mixture was purified by flash column chromatography over silica gel (eluent: 10% EtOAc/hexanes) to obtain quinone 10 as a pale yellow solid. Yield: 250 mg, 72%; R$_f$(3:7 EtOAc/hexanes): 0.81 (UV active); $^1$H NMR (400 MHz, CDCl$_3$): δ, 8.23 (ddd, J=7.8, 4.6 & 1.3 Hz, 2H, H-5,8), 8.12 (ddd, J=7.8, 4.6 & 1.3 Hz, 2H, H-6,7), 7.78 (ddd, J=7.8, 7.6 & 1.4 Hz, 2H, H-2',6'), 7.01 (ddd, J=7.8, 7.6 & 1.4 Hz, 2H, H-3',5'); MALDI-TOF: m/z, 267 (82%, M$^+$-Br), 347 (30%, M$^+$), 370 (85%, M+Na$^+$).

Example 2:
2,3-bis(4-fluoro)phenoxy-naphthoquinone (11)

p-Fluorophenol (118 mg in 10 mL THF) was mixed with 4 M NaOH (12 μL) and 2,3-dichloronaphthoquinone (in 10 mLTHF). The resulting mixture was stirred at 50° C. overnight. The reaction mixture was quenched by adding saturated aqueous ammonium chloride (20 mL) and the mixture was extracted with EtOAc (2×20 mL). The organic layers were pooled, the solvent was evaporated and the crude mixture was purified by flash column chromatography over silica gel (eluent: 10% EtOAc/hexanes) to obtain quinone 11 as a pale yellow solid.

Yield: 314 mg, 83%; R$_f$(3:7 EtOAc/hexanes): 0.85 (UV active); $^1$H NMR (400 MHz, CDCl$_3$): δ, 8.24 (ddd, J=7.8, 4.6 & 1.3 Hz, 2H, H-5,8), 8.13 (ddd, J=7.8, 4.6 & 1.3 Hz, 2H, H-6,7), 7.8 (ddd, J=7.8, 7.6 & 1.4 Hz, 2H, H-5'), 7.01 (ddd, J=7.8, 7.6 & 1.4 Hz, 2H, H-3'), 6.85 (ddd, J=7.8, 7.6 & 1.4 Hz, 2H, H-2'), 6.83 (ddd, J=7.8, 7.6 & 1.4 Hz, 2H, H-6'); MALDI-TOF: m/z, 267, 290 (22% & 75%, M$^+$-[fluorophenoxy] & with Na), 378 (100%, M$^+$).

Example 3:
2-chloro-3-(3,5-dimethyl)anilino-naphthoquinone (17)

A mixture of 2,3-dichloronaphthoquinone (450 mg, 1.25 equiv.) and 3,5-dimethylaniline (0.2 mL, 1 equiv.) in absolute ethanol was refluxed overnight and the resulting orange precipitate upon cooling was filtered, washed with absolute ethanol and recrystallized from ethanol to afford pure product.

Yield: 265 mg, 53%; R$_f$(3:7 EtOAc/hexanes): 0.76 (UV active); $^1$H NMR (400 MHz, CDCl$_3$): δ, 8.21 (ddd, J=7.8, 2.9 & 1.4 Hz, 1H, H-5), 8.18 (ddd, J=7.8, 2.9 & 1.4 Hz, 1H, H-8), 7.79 (ddd, J=7.8, 7.5 & 1.4 Hz, 1H, H-6), 7.75 (ddd, J=7.8, 7.5 & 1.4 Hz, 1H, H-7), 7.62 (br s, 1H, NH), 6.83 (s, 1H, H-4'), 6.64 (s, 2H, H-2',6'), 2.26 (s, 6H, methyls); MALDI-TOF: m/z, 313 (100%, MH$^+$), 335 (90%, M+Na$^+$).

Example 4:
2-chloro-3-(3,5-difluoro)anilino-naphthoquinone (24)

Naphthoquinone 24 was prepared in a manner analogous to the one used for making compound 17 described above.

Yield: 286 mg, 56%; R$_f$(3:7 EtOAc/hexanes): 0.82 (UV active); $^1$H NMR (400 MHz, CDCl$_3$): δ, 8.20 (ddd, J=7.8, 2.9 & 1.4 Hz, 1H, H-5), 8.16 (ddd, J=7.8, 2.9 & 1.4 Hz, 1H, H-8), 7.76 (ddd, J=7.8, 7.5 & 1.4 Hz, 1H, H-6), 7.74 (ddd, J=7.8, 7.5 & 1.4 Hz, 1H, H-7), 7.70 (br s, 1H, NH), 7.42 (s, 2H, H-2',6'), 7.12 (s, 1H, H-4'); MALDI-TOF: m/z, 321 (95%, MITE), 343 (85%, M+Na$^+$).

Example 5: 2-(3,5-bistrifluoromethyl)benzamido-2-chloronaphthoquinone (33)

A mixture of 2-amino-3-chloronaphthoquinone (207 mg, 1 equiv.) and NaH (48 mg, 1.2 equiv.; 60% dispersion in mineral oil) in THF was stirred vigorously for 20 min. and 3,5-bistrifluoromethylbenzoyl chloride (200 µL, 1.1 equiv.) was added gradually and stirred at room temperature for an additional 4 h. The reaction mixture was quenched with saturated aqueous ammonium chloride (20 mL) and the organic layer was extracted with EtOAc (2×20 mL). The solvent was evaporated and the crude product was purified by flash column chromatography over silica gel (eluent: 15% EtOAc/hexanes).

Yield: 380 mg, 85%; $R_f$ (3:7 EtOAc/hexanes): 0.85 (UV active); $^1$H NMR (400 MHz, CDCl$_3$): δ, 8.38 (s, 2H, H-2',6'), 8.32 (br s, 1H, NH), 8.20 (ddd, J=7.8, 4.4 & 1.4 Hz, 1H, H-5), 8.15 (ddd, J=7.8, 4.4 & 1.4 Hz, 1H, H-8), 8.12 (s, 1H, H-4'), 7.77 (ddd, J=7.8, 7.5 & 1.4 Hz, 2H, H-6,7); MALDI-TOF: m/z, 448 (100%, MH$^+$).

Example 6:
3-piperidinyl-naphthoquinone-2-carboxylic Acid (35)

A mixture of 2,3-dichloronaphthoquinone (570 mg, 1 equiv.), piperidine (370 µL, 1.5 equiv.), and K$_2$CO$_3$ was refluxed in ethanol for 16 h. The reaction mixture was concentrated redissolved in CH$_2$Cl$_2$ (25 mL) and washed with saturated ammonium chloride (20 mL), water (20 mL) and brine (20 mL). The organic layer was pooled, concentrated to dryness, and subjected to column chromatography over silica gel (eluent: 5%→15% EtOAc/hexanes).

Yield: 80 mg, 10% (2,3-bispiperidinyl-1,4-naphthoquinone, 32) and 300 mg, 42% (naphthoquinone 35);

$R_f$ (3:7 EtOAc/hexanes): 0.79 (UV active, compound 32) and 0.42 (UV active, compound 35); Other data on naphthoquinone carboxylic acid 35: $^1$H NMR (400 MHz, CDCl$_3$): δ, 8.15 (dd, J=7.8, 1.4 Hz, 1H, H-5), 7.87 (ddd, J=7.8, 7.4 & 1.4 Hz, 1H, H-8), 7.61 (ddd, J=7.8, 4.4 & 1.4 Hz, 2H, H-6,7), 3.58-3.37 (m, 4H, H-2',6'), 1.82-1.63 (m, 6H, H-3',4',5'); MALDI-TOF: m/z, 285 (100%, M$^+$).

Example 7:
3-morpholinyl-naphthoquinone-2-carboxylic Acid (36)

The same procedure delineated above was applied in preparing the naphthoquinone acid 36 where piperidine was replaced with morpholine.

Yield: 311 mg, 43%; $R_f$ (3:7 EtOAc/hexanes): 0.42 (UV active); $^1$H NMR (400 MHz, CDCl$_3$): δ, 8.12 (dd, J=7.8, 1.4 Hz, 1H, H-5), 7.89 (ddd, J=7.8, 7.4 & 1.4 Hz, 1H, H-8), 7.65-7.61 (m, 2H, H-6,7), 4.21-4.16 (m, 2H, H-2',6'), 3.82-3.80 & 3.51-3.45 (m, 6H, H-2',3',5',6'); MALDI-TOF: m/z, 288 (100%, MHz).

Example 8: Amidoxime Derivatives of Naphtho[1,2-d]thiazoles

These derivatives were prepared using a three-step protocol starting from an appropriate ketone. As a representative example, synthesis of amidoxime 49 is described below.

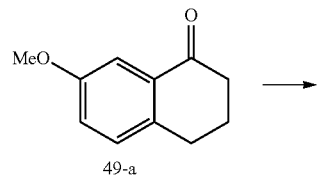

49-a

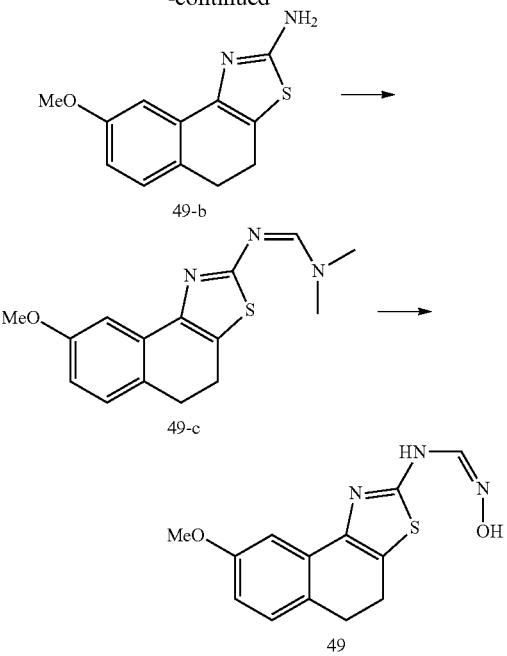

Synthesis of 8-methoxy-4,5-dihydronaphtho[1,2-d]thiazol-2-amine (49-a)

Thiourea (3.88 g, 51 mmol) and iodine (4.75 g, 18.7 mmol) were added to a solution of tetralone 49-a (3 g, 17 mmol) in absolute ethanol. The reaction mixture was heated at 100° C. in an open vessel for 3 h, and at the end all the solvent was allowed to evaporate. The residue was washed with ether (3×15 mL), dissolved in water (50 mL) and heated for 0.5 h and cooled. The white solid was filtered dried and recrystallized from 9:1 EtOH—H$_2$O and dried under vacuum to afford the hydroidide salt of 49-b. Upon a quick free-basing by washing with 5% NaOH and evaporating the dichloromethane layer, the sample was characterized by $^1$H NMR and MALDI-TOF and it was carried over to the next step.

Synthesis of N'-hydroxy-N-(8-methoxy-4,5-dihydronaphtho[1,2-d]thiazol-2-yl)formimidamide 49

Aminothiazole 49-b (1.4 mmol) from the previous step was heated at 100° C. with N,N-dimethylform-amide dimethyl acetal (220 µL, 1.64 mmol) in toluene (15 mL) for 5 h and the solvent was evaporated. The residue was recrystallized from cyclohexane and the resulting solid (49-c) was stirred with hydroxylamine hydrochloride (575 mg, 8.3 mmol) in methanol (20 mL) at room temperature for 16 h. The reaction mixture was concentrated and it was neutralized by adding 10% Na$_2$CO$_3$ solution dropwise (pH 9). A brown precipitate was formed and it was filtered and washed with water and recrystallized further from 1,4-dioxane to afford pure amidoxime 49.

Example 9: 2-Lactoylamino-7-methoxy-4,5-dihydronaphtho[1,2-d]thiazole (42)

2-Amino-7-methoxy-4,5-dihydro-naphtho[1,2-d]thiazole (Chordia, et al. 2002, *Bioorg. Med. Chem. Lett.*, 12:1563-66) (85 mg, 365 µmmol) was coupled with (S)—O-(tert-butyldiphenyl-silyl)lactic acid (Faure, et al. 2002, *J. Org. Chem.*, 67:1061-70) using HBTU (152 mg, 1.1 equiv.) and i-PrNEt$_2$ (230 µL, 3.5 equiv.) in THF (10 mL). After stirring the reaction mixture overnight, water (10 mL) was added and the product was extracted into EtOAc (2×15 mL). The pooled organic phase was evaporated and the product was diluted with THF (10 mL) and treated with n-Bu$_4$NF (1.2 mL, 1 M in THF) at room temperature for 4 h. The reaction mixture was concentrated and subjected to flash column chromatography over silica gel (eluent: 20% EtOAc/hexanes) to yield an off-white solid.

Yield: 59 mg, 53% (over two steps); R$_f$ (3:7 EtOAc/hexanes): 0.21 (UV active); $^1$H NMR (400 MHz, CDCl$_3$): δ, 7.55 (d, J=9.1, 1H, H-9), 7.37 (br s, 1H, NH), 6.79 (m, 2H, H-6,7), 4.54 (m, 1H, H-1'), 3.83 (s, 3H, OMe), 3.07-2.86 (m, 4H, H-4,5), 1.28 (d, J=6.7 Hz, 3H, H-3'); MALDI-TOF: m/z, 305 (30%, MH$^+$), 327 (80%, M+Na$^+$).

Example 10: 2-(2-Furyl)methylamino-7-methoxy-4,5-dihydro-naphtho[1,2-d]thiazole (43)

2-Amino-7-methoxy-4,5-dihydro-naphtho[1,2-d]thiazole (325 mg, 1.4 mmol) and freshly distilled furfural (162 µL, 1.7 mmol) were added to 1:1 CH$_2$Cl$_2$-MeOH containing anhydrous MgSO$_4$ (1 g) and stirred under argon for 6 h (the solution turned yellow after 30 min). The mixture was filtered and the filtrate was concentrated. The previously known product (45) was purified by chromatography over silica gel (eluent: 10% EtOAc/hexanes). Yield: 404 mg, 94%; R$_f$ (3:7 EtOAc/hexanes): 0.75 (UV active); $^1$H NMR (400 MHz, acetone-d$_6$): δ, 7.97 (s, 1H, HC=N), 7.79 (d, J=9.2 Hz, 1H, H-9), 7.35 (d, J=2.1 Hz, 1H, H-5'), 6.85 (m, 3H, H-6,8; H-3'), 6.77 (m, 1H, H-4'), 3.82 (s, 3H, OMe), 2.86-2.82 (m, 4H, H-4,5); MALDI-TOF: m/z, 311 (100%, MH$^+$), 350 (15%, M+K$^+$).

The Schiff base 45 (20 mg, 64.5 µmmol) was dissolved in MeOH (8 mL) and NaBH$_4$ (15 mg, 395 µmol) was added and the mixture was stirred overnight. After concentrating the reaction mixture was purified by flash column chromatography over silica gel (15% EtOAc/hexanes). Yield: 29 mg, 96%; Rf (3:7 EtOAc/hexanes): 0.73 (UV active); $^1$H NMR (400 MHz, acetone-d$_6$): δ, 7.81 (d, J=9.2 Hz, 1H, H-9), 7.34 (d, J=2.1 Hz, 1H, H-5'), 6.89 (m, 3H, H-6,8; H-3'), 6.78 (m, 1H, H-4'), 4.66 (br s, 1H, NH), 4.32 (s, 2H, CH$_2$-furyl), 3.85 (s, 3H, OMe), 2.86-2.82 (m, 4H, H-4,5); MALDI-TOF: m/z, 313 (100%, MH$^+$), 335 (20%, M+Na$^+$).

Example 11

Amidoxime 49

Yield: 52% over 3 steps; R$_f$ (3:7 EtOAc/hexanes): 0.42 (UV active); $^1$H NMR (400 MHz, acetone-d$_6$): δ, 9.38 (br s, 2H, NH, OH), 9.26 (s, 1H, CH=N), 7.52 (d, J=8.6 Hz, 1H, H-6), 7.37 (d, J=1.9 Hz, 1H, H-9), 6.85 (dd, J=8.6, 1.9 Hz, 1H, H-7), 3.75 (s, 3H, OMe), 3.11-2.92 (m, 4H, H-4,5); MALDI-TOF: m/z, 276 (35%, MH$^+$), 298 (20%, M+Na$^+$).

Amidoxime 50 (Prepared from the Commercially Available 5-mehtoxy-1-tetralone):

Final compound was purified by flash chromatography over silica gel (eluent: 2% MeOH-DCM).

Yield: 61% over 3 steps; R$_f$ (3:7 EtOAc/hexanes): 0.33 (UV active); $^1$H NMR (400 MHz, acetone-d$_6$): δ, 9.18 (br s, 2H, NH, OH), 9.12 (s, 1H, CH=N), 8.05 (d, J=8.7 Hz, 1H, H-9), 7.38 (d, J=8.7 Hz, 1H, H-8), 6.85 (d, J=8.6 Hz, 1H, H-7), 3.79 (s, 3H, OMe), 3.21-2.97 (m, 4H, H-4,5); MALDI-TOF: m/z, 276 (60%, MH$^+$), 298 (40%, M+Na$^+$).

Amidoxime 51 (Prepared from the Commercially Available 6,7-dimehtoxy-1-tetralone):

Yield: 48% over 3 steps; R$_f$ (5% MeOH/DCM): 0.28 (UV active); $^1$H NMR (400 MHz, acetone-d$_6$): δ, 9.61 (br s, 2H, NH, OH), 7.81 (s, 1H, CH=N), 7.39 (s, 1H, H-9), 6.83 (s, 1H, H-6), 3.83 & 3.81 (2×s, 6H, OMe), 3.22-2.85 (m, 4H, H-4,5); MALDI-TOF: m/z, 306 (20%, MH$^+$), 328 (M+Na$^+$), 290 (100%, M$^+$-0).

Amidoxime 52 (Prepared from 6,7-(methylenedioxy)-1-tetralone):

Yield: 67% over 3 steps; R$_f$ (3:7 EtOAc/hexanes): 0.39 (UV active); $^1$H NMR (400 MHz, acetone-d$_6$): δ, 9.55 (br s, 2H, NH, OH), 7.89 (s, 1H, CH=N), 7.25 (s, 1H, H-9), 6.85 (s, 1H, H-6), 6.02 (d, J=10.3 Hz, 2H, OCH$_2$O), 3.21-2.95 (m, 4H, H-4,5); MALDI-TOF: m/z, 290 (90%, MH$^+$), 312 (30%, M+Na$^+$).

Amidoxime 53 (Prepared from 6,7-dihydro-8H-1,3-dioxolo[4,5-g][1]benzopyran-8-one):

Yield: 55% over 3 steps; R$_f$ (3:7 EtOAc/hexanes): 0.36 (UV active); $^1$H NMR (400 MHz, acetone-d$_6$): δ, 9.64 & 9.55 (2×br s, 2H, NH & OH), 7.79 (s, 1H, CH=N), 7.17 (s, 1H, H-9), 6.51 (s, 1H, H-6), 6.02 (d, J=10.6 Hz, 2H, OCH$_2$O), 5.33 (d, J=9.8 Hz, 2H, H-4); MALDI-TOF: m/z, 292 (80%, MH$^+$), 314 (45%, M+Na$^+$).

Amidoxime 54 (Prepared from the Commercially Available 7-methoxy-2,3-dihydro-4H-chromen-4-one):

Yield: 69% over 3 steps; R$_f$ (3:7 EtOAc/hexanes): 0.43 (UV active); $^1$H NMR (400 MHz, acetone-d$_6$): δ, 9.51 & 9.48 (2×br s, 2H, NH & OH), 9.36 (s, 1H, CH=N), 7.65 (d, J=9.2 Hz, 1H, H-9), 7.57 (d, J=9.2 Hz, 1H, H-8), 6.70 (d, J=6 Hz, 1H, H-6), 5.35 (d, J=9.6 Hz, 2H, H-4); MALDI-TOF: m/z, 278 (76%, MH$^+$), 300 (55%, M+Na$^+$).

Amidoxime 55 (Prepared from the Commercially Available 7-methoxyflavanone):

Yield: 61% over 3 steps; R$_f$ (3:7 EtOAc/hexanes): 0.54 (UV active); $^1$H NMR (400 MHz, methanol-d$_4$): δ, 8.31 (br s, 2H, NH & OH, partially exchanged), 7.75 (dd, J=8.8, 1.4 Hz, 1H, H-9), 7.52-7.33 (m, 6H, CH=N, phenyl), 6.55 (dd, J=8.8 & 2.4 Hz, 1H, H-8), 6.49 (dd, J=2.4 & 1.4 Hz, 1H, H-6), 5.08 (s, 1H, H-4), 3.78 (s, 3H, OMe); MALDI-TOF: m/z, 354 (65%, MH$^+$), 376 (40%, M+Na$^+$).

Amidoxime 56 (Prepared from the Commercially Available 5-mehtoxy-1-indanone):

Yield: 71% over 3 steps; R$_f$ (3:7 EtOAc/hexanes): 0.34 (UV active); $^1$H NMR (400 MHz, DMSO-d$_6$): δ, 10.51 (br s, 1H, NH or OH), 10.33 (s, 1H, CH=N), 7.63 (s, 1H, NH or OH), 7.40 (d, J=8.8 Hz, 1H, H-8), 7.18 (d, J=1.4 Hz, 1H, H-5), 6.88 (d, J=8.8 Hz, 1H, H-6), 3.79 (s, 3H, OMe), 3.76 (d, J=11.2 Hz, 2H, H-4); MALDI-TOF: m/z, 262 (66%, MH$^+$), 284 (20%, M+Na$^+$).

Amidoxime 57 (Prepared from 6,7,8,9-tetrahydro-5H-cyclohepta[f]-1,3-benzodioxol-5-one):

Yield: 37% over 3 steps; R$_f$ (3:7 EtOAc/hexanes): 0.45 (UV active); $^1$H NMR (400 MHz, acetone-d$_6$): δ, 9.57 (br s, 2H, NH, OH), 7.90 (s, 1H, CH=N), 7.27 (s, 1H, H-10), 6.88 (s, 1H, H-7), 6.05 (d, J=10.3 Hz, 2H, OCH$_2$O), 3.11-2.85 (m, 4H, H-4,6), 2.28 (m, 2H, H-5); MALDI-TOF: m/z, 304 (70%, MH$^+$), 326 (40%, M+Na$^+$).

Amidoxime 58 (Prepared from 7,8-dihydro-1,3-dioxolo[4,5-h][1]benzoxepin-9(6H)-one):

Yield: 51% over 3 steps; R$_f$ (3:7 EtOAc/hexanes): 0.32 (UV active); $^1$H NMR (400 MHz, methanol-d$_4$): δ, 7.69 (s, 1H, CH=N), 6.49 (s, 1H, H-10), 5.92 (s, 1H, H-7), 5.91 (d, J=6 Hz, 2H, OCH$_2$O), 4.28 (t, J=5.6 Hz, 2H, H-5) 3.18 (t, J=5.6 Hz, H-4); MALDI-TOF: m/z, 306 (85%, MH$^+$), 328 (50%, M+Na$^+$).

Amidoxime 59 (Prepared from the Commercially Available 3,4-methylenedioxy-acetophenone):

Yield: 75% over 3 steps; $R_f$ (5% MeOH/DCM): 0.42 (UV active); $^1$H NMR (400 MHz, acetone-$d_6$): δ, 8.67 (br s, 2H, NH & OH), 7.18 (s, 1H, CH=N), 6.91 (d, J=8.8 Hz, 1H, H-6), 6.62 (d, J=2.4 Hz, 1H, H-10), 6.41 (s, 1H, H-5), 6.03 (d, J=8.8 Hz, 1H, H-7), 2.94 & 2.91 (2xs, 6H, OMe); MALDI-TOF: m/z, 280 (70%, MH$^+$), 263 (MH$^+$—OH).

Example 12: MetAP Variants

Materials and Methods
Subcloning of the Two MetAPs from *M. tuberculosis*.
MtMetAP1c The N-terminal polyHis-tag MtMetAP1c gene was amplified by polymerase chain reaction (PCR) from *M. tuberculosis* (CDC1551) genomic DNA using Taq polymerase. The *M. tuberculosis* (CDC1551 strain) genomic DNA was generously provided by Dr. William Bishai. The primers used were 5'-GCG GGA TCC CCT AGT CGT ACC GCG CTC-3' (SEQ ID NO: 1) and 5'-GCG CTC GAG CTA CAG ACA GGT CAG GAT C-3' (SEQ ID NO: 2) for forward and reverse directions, respectively. The PCR fragments were cloned into pET28a, using the BamHI and XhoI restriction sites respectively.
MtMetAP1a The C-terminal polyHis-tag MTMAP1A gene was amplified by PCR from pET28a (MtMAP1a) plasmid (this plasmid was also sub-cloned from *M. tuberculosis* genomic DNA generously provided by Dr. William Bishai). The primers used were 5'-GCG CCA TGG GCC CAC TGG CAC GGC TGC GGG GTC-3' (SEQ ID NO: 3) and 5'-GCG CTC GAG ACC GAG CGT CAG AAT TCG GGG CCC-3' (SEQ ID NO: 4) for forward and reverse directions, respectively. The PCR fragments were cloned into pET28b, using the NcoI and XhoI restriction sites, respectively. Both MtMetAP1a and MtMetAP1c clones were confirmed by sequencing.
Overexpression and Purification of Recombinant MetAP from *M. tuberculosis*.
MtMetAP1a

*E. coli* BL21 cells (DE3) containing the expression plasmid were cultured at 37° C. in 1 Liter of *Listeria* Broth (LB) containing 30 mg kanamycin until OD600 reached about 1.0. The expression of MtMetAP1a was induced by addition of isopropyl β-D-thiogalactopyranoside (IPTG) to a final concentration of 1 mM followed by continued shaking of the culture flask at 280 rpm, at 16° C. for 48 hrs. The cells were harvested and washed with 1×PBS (137 mM NaCl, 2.7 mM KCl, 4.3 mM $Na_2HPO_4 \cdot 7H_2O$, 1.4 mM $KH_2PO_4$ pH 7.3). The cells were sonicated in +TG buffer (50 mM Hepes pH 8.0, 0.5M KCl, 10% glycerol, 5 mM imidazole, and 0.1% Triton-X-100) with EDTA-free Protease Inhibitor tablets. The resulting lysate was centrifuged at 8000×g for 10 min. The supernatant was loaded onto pre-equilibrated (+TG buffer) Talon resin (Clontech). After equilibration for 30 min, the beads were washed three times with −TG buffer (50 mM Hepes pH 8.0, 0.5 M KCl, and 5 mM imidazole). The enzyme was eluted with 100 mM imidazole in −TG buffer. The protein was quantified using the Bradford assay. The average yield for MtMetAP1a was 4.3 mg/L of culture.
MtMetAP1c

*E. coli* cells (BL21) containing the expression plasmid were cultured at 37° C. in 1 Liter of LB containing 30 mg kanamycin until OD600 reached about 0.6-0.7. The expression was induced by addition of IPTG to a final concentration of 1 mM followed by shaking the culture flask at 37° C., and 275 rpm for 4 hr. The cells were harvested and washed with 1×PBS. The cells were sonicated in 1×PBS with 0.2% Triton-X-100 and EDTA-free protease inhibitor tablets. The resulting cell free lysate was centrifuged at 8000×g for 10 min. The supernatant was loaded onto pre-equilibrated (1×PBS) Talon resin (Clontech). After equilibration for 30 min, the beads were washed three times with basic buffer (10 mM Hepes pH 8.0, 100 mM KCl, 1.5 mM $MgCl_2$, and 10% glycerol). The enzyme was eluted with 75 mM imidazole in Basic buffer. The protein was quantified using the Bradford assay. The average yield for MtMetAP1c was 13.2 mg/L of culture.
Metal Dependence of MtMetAPs
MtMetAP1c After purification, recombinant MtMetAP1c was dialyzed into Buffer A (40 mM Hepes buffer (p.H 7.5), 100 mM NaCl and 5 mM EDTA) at 4° C. for 22 hr and the buffer was exchanged to Buffer B (40 mM Hepes buffer (p.H 7.5), and 100 mM NaCl) at 4° C. The metal dependence of MtMetAP1c was determined by measuring enzymatic activity in the presence and absence of 0.1 μM-10 mM $CoCl_2$ or $MnCl_2$, using the coupled methionine-proline aminopeptidase assay. The reactions were carried out in 96-well plates at room temperature and monitored at 405 nm on a spectrophotometer. The total reaction volume was 50 μL and each reaction contained 40 mM Hepes buffer (p.H 7.5), 100 mM NaCl, 100 μg/mL BSA, 0.1 U/mL ProAP, 600 μM substrate (Met-Pro-pNA), and 51 nM MtMetAP1c. The MetAP reaction was allowed to go for 30 min at room temperature followed by addition of ProAP. The background hydrolysis was corrected and the activities were determined relative to the optimal metal concentration.
MtMetAP1a After purification, recombinant MtMetAP1a was dialyzed into Buffer C (50 mM Hepes buffer (p.H 7.0), 10 mM NaCl and 5 mM EDTA) at 4° C. overnight and the buffer was exchanged to Buffer D (50 mM Hepes buffer (p.H 7.0), and 10 mM NaCl) at 4° C. The metal dependence of MtMetAP1a was determined by measuring enzymatic activity in the presence of 1 μM-10 mM $CoCl_2$ and $MnCl_2$, using the methionine-proline aminopeptidase assay. The reactions were carried out in 96-well plates at room temperature and monitored at 405 nm on a spectrophotometer. The total reaction volume was 50 μL and each reaction contained 40 mM Hepes buffer (p.H 7.5), 100 mM NaCl, 100 μg/mL BSA, 0.1 U/mL ProAP, 600 μM substrate (Met-Pro-pNA), and 323 nM MtMetAP1a. The MetAP reaction was allowed to go at room temperature followed by addition of ProAP. The background hydrolysis was corrected and the activities were determined relative to the optimal metal concentration.
Determination of Kinetic Constants of MtMetAPs The kinetic constants of the mycobacterial MetAPs were determined using a coupled methionine-proline aminopeptidase assay developed by Dr. Dehua Pei at The Ohio State University (Zhou, Y., et al. 1999. Anal. Biochem. 280:159-165). The substrate used in this assay is a dipeptide, Met-Pro coupled to p-nitroaniline. The dipeptide substrate, Met-Pro-pNA was synthesized by Dr. Keechung Han. The kinetic constants were obtained by measuring enzyme activity at different substrate concentrations. The reactions were carried out in 96-well plates at room temperature and monitored at 405 nm on a spectrophotometer. The total reaction volume was 100 μL and each reaction contained 40 mM Hepes buffer (pH 7.5), 100 mM NaCl, 1 μM $CoCl_2$, 100 μg/mL BSA, 0.1 U/mL ProAP, O-800 μM substrate (Met-Pro-pNA), 334 nM MtMetAP1c and 3.29 μM MtMetAP1a, respectively. The background hydrolysis was corrected and the data was fitted against the Michealis-Menten equation: V=Vmax*[S]/(Km+[5]) using the Graphpad prism software for one-site binding hyperbola.

pH Dependence of MtMetAPs

The reactions were carried out in 96-well plates at room temperature by measuring the activities of both MtMetAPs using buffers at different pH. The total reaction volume was 50 µL and each reaction contained buffer (50 mM Sodium acetate p.H 4.0-5.5, or 50 mM MES p.H 5.5-7.0, or 50 mM HEPES p.H 7.0-8.5, or 50 mM Tricine p.H 8.0-9.0 or 50 mM Ethanolamine p.H 8.5-10.0), 10 mM NaCl, 1 µM $CoCl_2$, 100 µg/mL BSA, 0.1 U/mL ProAP, 600 µM substrate (Met-Pro-pNA), 328 nM MtMetAP1c and 1.78 µM MtMetAP1a, respectively. The reaction was allowed to go for 30 min at room temperature. Then the reaction was terminated with 1 µL 10% TFA, and neutralized with 1.4 µL of 1M NaOH. The pH was adjusted to 8.0 by addition of 5 µL of 1M HEPES buffer. Thereafter, ProAP was added and the reaction was monitored at 405 nm on a spectrophotometer. The background hydrolysis was corrected and the activities were determined relative to the optimal pH for each MtMetAP.

Determination of Optimal Temperature of MtMetAPs

The activity of both mycobacterial MtMetAPs were determined at different temperatures from 4° C. to 65° C. The total reaction volume was 50 µL and each reaction contained 40 mM Hepes buffer (p.H 7.5), 100 mM NaCl, 100 µg/mL BSA, 0.1 U/mL ProAP, 600 µM substrate (Met-Pro-pNA), 315 nM MtMetAP1c and 2.14 µM MtMetAP1a, respectively. The reaction was allowed to go for 30 min and monitored at 405 nm on a spectrophotometer. The background hydrolysis was corrected and the activities were determined relative to the optimal temperature.

High-Throughput Screening for MtMetAP1c Inhibition

About 175,000 compounds were screened against MetAP1c at concentrations of 30 µM in 384-well plates, using the dipeptide substrate. The compounds were dissolved in Dimethylsulfoxide (DMSO). The initial screen was conducted using a titertek instrument with liquid handling capabilities coupled to a spectrophotometer. The total reaction volume was 50 µL and each reaction contained 40 mM Hepes buffer (pH 7.5), 100 mM NaCl, 100 µg/mL BSA, 0.1 U/mL ProAP, 1.5 mM $CoCl_2$, 600 µM substrate (Met-Pro-pNA), and 252 nM MtMetAP1c. The enzyme was pre-incubated with compounds for 20 min at room temperature followed by addition of 600 µM substrate. The reaction was incubated at room temperature for 30 min and monitored at 405 nm on a spectrophotometer. The Compounds that showed greater than 30-40% inhibition were chosen as "hits".

Determination of $IC_{50}$ of Inhibitors of MtMetAPs and Clustering of Structural Classes of Inhibitors (ASDI-ISIS)

We determined the concentration needed for 50% inhibition in 96-well plates at final concentrations ranging from 100 µM-300 nM (for 81 compounds that were available in larger quantities). The total reaction volume was 50 µL and each reaction contained each MtMetAP1 respectively and 40 mM Hepes buffer (p.H 7.5), 100 mM NaCl, 100 µg/mL BSA, 0.1 U/mL ProAP, 1.5 µM $CoCl_2$, 600 µM substrate (Met-Pro-pNA). The enzyme was pre-incubated with compounds for 20 min at room temperature followed by addition of substrate. The reaction was incubated at room temperature for 30 min and monitored at 405 nm on a spectrophotometer. The background hydrolysis was corrected and the data was fitted against the sigmoidal-dose response (variable slope) equation using GraphPad Prism software.

Determination of Minimum Inhibitory Concentration in *M. tuberculosis*

The primary screen against replicating *M. tuberculosis* was conducted with 14 MtMetAP inhibitors at concentrations ranging from 50 to 0.05 µg/mL. The MetAP inhibitors were serially diluted in DMSO and added to 7H9 broth and OADC (without Tween 80) to give final concentrations of 50, to 0.05 µg/mL. A culture of *M. tuberculosis* H37Rv was grown till O.D. of 1.0, and diluted to 1/100. Then each tube containing compound was inoculated with 0.1 mL of culture to give a total assay volume of 5 mL. The controls were DMSO, Isoniazid (a positive control) and a blank (drug free media). The 15-ml conical assay tubes containing mycobacteria were incubated at 37° C. and 5% $CO_2$. Formation of granulation was monitored for two weeks. The primary screen against non-replicating *M. tuberculosis* was conducted with of 21 MtMetAP inhibitors against non-replicating *M. tuberculosis* at concentrations ranging from 0.5 to 100 µM for three weeks.

Determination of Minimum Inhibitory Concentration in Aged-cultured *M. tuberculosis*

The screen against aged-cultured *M. tuberculosis* was conducted using a persister model as described by Byrne et al., 2007 (Byrne, S., et al. 2007. *Antimicrob. Agents Chemother.* 51:4495-7). Briefly, a 2 month old *M. tuberculosis* H37Ra culture grown in 7H9 medium (Difco) with 10% albumin-dextrose-catalase (ADC) and 0.05% Tween 80 was resuspended in acid 7H9 medium (pH5.5) without ADC. The bacterial cell suspension was used as inocula for assaying the activity of the compounds for persister bacilli. The compounds were diluted from the stock solution (10 mM in DMSO) to 10 µM (final) followed by incubation with the bacilli in 200 µl in acid pH5.5 7H9 medium without ADC in 96-well plates without shaking under 1% oxygen in a hypoxic chamber. The assay was done in duplicate. Rifampin (5 µg/ml) was used as a positive control. After 3 day drug exposure, the viability of the bacilli was determined by adding 20 µl of 1 mg/ml XTT (2,3-bis-(2-methoxy-4-nitro-5-sulfophenyl)-2H-tetrazolium-5-carboxanilide) and incubated at 37° C. up to 7 days when the plates were read at OD485 nm.

Sub-Cloning of MtMetAP1a and MtMetAP1c into pSCW35ΔsigF.

The entire ORFs of MtMetAP1a and MtMetAP1c genes were amplified by polymerase chain reaction (PCR) in the sense orientation from *M. tuberculosis* strain CDC1551 genomic DNA. Then the PCR fragments were cloned into pSCW35 vector, using the NdeI and PacI restriction sites. The primers used were: For MtMetAP1a: for forward 5' CGCATTAATGCCCACTGGCACGGCTGCGGGGTC'3 (SEQ ID NO: 5) and reverse direction 5' CCTTAAT-TAACTAACCGAGCGTCAGAATTCGGGGC'3 (SEQ ID NO: 61 respectively. For MtMetAP1c: for forward 5' GGAATTCCATATGCCTAGTCGTACCGCGC'3 (SEQ ID NO: 7) and reverse direction 5' CCTTAATTAACTACA-GACAGGTCAGGATC'3 (SEQ ID NO: 8) respectively. The pSCW35ΔsigF-(MtMetAP1a) and pSCW35ΔsigF-(MtMetAP1c) clones were verified by DNA sequencing (GeneID: 888564 for MtMetAP1a and 888596 for MtMetAP1c).

Over-Expression of MtMetAP1a and MtMetAP1c in *M. tuberculosis* in the Presence of Inhibitor.

We constructed knock-in strains of both MtMetAP1s by transforming *M. tuberculosis* CDC 1551 with pSCW35ΔsigF-(MtMetAP1a) and pSCW35ΔsigF-(MtMetAP1c) respectively. In addition, we transformed *M. tuberculosis* with a control plasmid, pSCW35ΔsigF which is an empty vector kindly provided by Dr. Tirumalai. All three transformants were grown until early log phase and expression was induced by addition of 0.2% acetamide followed by incubation for 24 hr. We diluted the cells to an OD600 of 0.05 and cultured them separately in the presence of 10 µg/mL 2,3-dichloro-1,4-naphthoquinone or DMSO. Then growth was followed by recording OD600 every 24 hr for 7 days. The *M. tuberculosis* cultures were grown in Middlebrook 7H9 medium and supplemented with 2% glycerol, 0.05% Tween-80 and 10% albumin/dextrose complex (ADC).

Sub-cloning of Anti-Sense of MtMetAP1a and MtMetAP1c into pSCW35ΔsigF.

In order to study the requirement of MtMetAP1a and MtMetAP1c for growth and survival of *M. tuberculosis*, each of the mycobacterial MetAP1s was cloned in the reverse orientation downstream of the acetamide regulated promoter ($P_{ace}$) in pSCW35ΔsigF. The entire ORFs of MtMetAP1a and MtMetAP1c genes were amplified by polymerase chain reaction (PCR) in the anti-sense orientation from *M. tuberculosis* strain CDC1551 genomic DNA. Then, the PCR fragments were cloned into pSCW35ΔsigF vector, using the NdeI and Pad restriction sites. The pSCW35ΔsigF-(α-MtMetAP1a) and pSCW35ΔsigF-(α-MtMetAP1c) clones were verified by restriction digestion and DNA sequencing.

Knock-down of MtMetAP1a and MtMetAP1c in *M. tuberculosis*.

Knock-down strains of both MtMetAP1s were constructed by transforming *M. tuberculosis* CDC 1551 with the anti-sense constructs: pSCW35ΔsigF-(α-MtMetAP1a) and pSCW35ΔsigF-(α-MtMetAP1c). Then, *M. tuberculosis* was transformed with a control plasmid, pSCW35ΔsigF. All three transformants were grown until early log phase and expression was induced by addition of 0.2% acetamide for 24 hr. Then the cultures were grown for three weeks on plates in the presence and absence of acetamide. The *M. tuberculosis* culture plates (Middlebrook 7H10 agar) were supplemented with 5% glycerol and 10% ADC. The colony counts were conducted after three weeks and percent viability was determined using the formula below:

Viability %=100×[number of colonies on 7H10 K15+0.2% Acetamide/number of colonies on 7H10 K15]

Mycobacterial RNA Isolation

To confirm that the levels of both mycobacterial MetAP1s were altered as expected, RNA was extracted from the acetamide induced transformants and real-time quantitative PCR was used to quantitate the transcript levels of both enzymes as described below. *M. tuberculosis* cultures containing plasmids over-expressing sense and anti-sense constructs of MtMetAP1a and MtMetAP1c and the control plasmid pSCW35ΔsigF were grown to exponential phase and induced with 0.2% acetamide for 24 hr. Following induction cells were pelleted by centrifugation at 3000 rpm for 10 min. The pellet was washed once with PBS and resuspended in 1 mL of Trizol reagent (Invitrogen technologies, Carlsbad, Calif., USA) in 2 mL O-ring tubes. Cells were lysed by 8 bead beating cycles of 30s each (with 0.1 mm Silica Zirconia beads-Biospec products), on a bead beater (Biospec products). The tubes were then centrifuged at 13,000 rpm for 5 min to recover the supernatant; the beads and cell debris were discarded at this point. 200 μL of chloroform was added to the supernatant, and centrifuged at 13,000 rpm for 5 min following a 30s vortex cycle. To precipitate the RNA, one volume of isopropanol was added to the aqueous phase, mixed and incubated at RT for 10 min. RNA was pelleted by centrifuging at 13,000 rpm for 10 min at 4° C. The pellet was washed twice with 70% ethanol and dried at RT. The RNA samples were resuspended in DEPC water and quantitated by measuring $A_{260}$. The quality of the RNA was assessed by the $A_{260}/A_{280}$ ratio and by agarose gel electrophoresis.

Real Time RT-PCR Analysis

To quantitate transcript levels of MtMetAP1a and MtMetAP1c under conditions where the levels of the genes was being perturbed, RNA was isolated from the acetamide induced cultures (as described above), treated with RNase-free DNase (Ambion) and 0.5 μg of RNA subjected to reverse transcription using the iScript cDNA synthesis kit (Biorad). This was followed by real-time quantitative PCR using the SYBR Green Supermix (Bio-Rad Laboratories). MtMetAP1a and MtMetAP1c were amplified using gene specific primers, both sets of primers amplify 200 nt of the respective gene. The primers used were: For MtMetAP1a: for forward 5'-CCGAGGTGCTCGCGCCCGGTG-3' (SEQ ID NO: 9) and reverse direction 5'-TTCGATGGCATGCGC-GACG-3' (SEQ ID NO: 10) respectively. For MtMetAP1c: for forward 5'-GCTGGGCTACAAGGGATTCCCGAAG-3' (SEQ ID NO: 11) and reverse direction 5' TCCGGTCAAC-GAGCAACCGGTG-3' (SEQ ID NO: 12) respectively. The relative fold change of mRNA of the two genes under each of the experimental conditions was measured by normalizing its transcript level to that of *M. tuberculosis* sigma factor A (sigA). The fold differences in transcript levels were derived by comparing the Ct values in the test (sense 1a, sense 1c, anti-sense 1a, anti-sense 1c) samples with that of the control sample (pSCW35ΔsigF) (GeneID: 888564 for MtMetAP1a and 888596 for MtMetAP1c).

Results

Overexpression, Purification and Enzymatic Characterization of MtMetAP1a and MtMetAP1c A BLAST search of the recently disclosed genome of *M. tuberculosis* (Cole, S. T. et al. 1998. *Nature* 393:537-544) revealed the existence of two orthologs of *E. coli* MetAP and their N-terminal extension suggested that they belong to MtMetAP1a and MtMetAP1c classes, respectively (FIG. 1A). Previously, we have succeeded in cloning, overexpressing and purifying recombinant MtMetAP1c with an N-terminal poly-histidine tag for crystallographic studies (Addlagatta, A., M. Quillin, O. Omotoso, J. O. Liu, and B. W. Matthews. 2005. Biochemistry 44:7166-7174). Recombinant MtMetAP1a was overexpressed and purified in a similar manner, except that the expression vector pET-28b was used to obtain a C-terminal poly-His tag on the protein. Both proteins were efficiently purified to near homogeneity by immobilized metal affinity chromatography using Talon® resins. Upon purification, C-terminal poly-His-tag MtMetAP1a, and N-terminal poly-His-tag MtMetAP1c were seen at about 28 kDa, and 32 kDa on Coomassie blue-stained SDS-PAGE respectively (FIG. 1B). The average yield from 1 Liter of *E. coli* culture for MtMetAP1a, and MtMetAP1c were 4.3, and 13.2 mg, respectively.

The enzymatic activities of the purified *M. tuberculosis* MetAPs were assessed using a chromogenic substrate (Met-Pro-pNA) in a coupled enzymatic assay with proline aminopeptidase as the coupling enzyme (Zhou, Y., et al. 1999. *Anal. Biochem.* 280:159-165). Both purified recombinant proteins were found to be catalytically active in this assay (FIG. 3). The kinetic constants for MtMetAP1a and MtMetAP1c were determined by measuring enzyme activity at different substrate concentrations ranging from 0 to 800 μM. The $K_m$ for the artificial substrate was similar for both enzymes, while the $k_{cat}$ for MtMetAP1c was catalytically 10-fold higher than that for MtMetAP1a (Table 1).

TABLE 1

Kinetic Constants for MetAPs from *M. tuberculosis* using a Dipeptide Substrate (Met-Pro-pNA)

| Kinetic Constants | MtMetAP1a | MtMetAP1c |
|---|---|---|
| Km (μm) | 122 ± 22 | 113 ± 31 |
| Kcat (s$^{-1}$) | 0.03 | 0.38 |
| Kcat/Km (M$^{-1}$min$^{-1}$) | 1.3 × 10$^4$ | 2.0 × 10$^5$ |
| Vmax (μM/min) | 5.1 ± 0.2 | 7.6 ± 0.5 |

Using the same enzymatic assay, we also determined the effects of temperature on both enzymes. The temperature profile of MtMetAP1a gave a bell-shaped curve, with an optimal temperature of 42° C. In contrast, the activity of MtMetAP1c increased by smaller increments as temperatures were increased from 4° C. to 50° C. before loss of activity was seen at 65° C. These results suggested that MtMetAP1c had a slightly higher thermostability than MtMetAP1a. The pH profiles of both MtMetAPs were determined by measuring the enzymatic activity in different buffers. The optimal pH for both MtMetAPs was found to be 8.0 using 50 mM HEPES as buffer. It is noteworthy that MtMetAP1a had optimal activity from pH 6.5 to pH 8.0 while MtMetAP1c had a much steeper decline in activity upon pH changes from 8.0.

Since the physiological metal cofactor for MetAPs remains controversial, it was determined the metal dependence of both MtMetAPs. Both MtMetAPs were found to be active in the presence of Co$^{2+}$ or Mn$^{2+}$. For MtMetAP1c, concentration-dependent inhibition was observed in the presence of increasing amounts of CoCl$_2$. In contrast, MtMetAP1c retained its optimal activity in the presence of 0.1-10 μM of Mn$^{2+}$ and only a slight decrease in activity was seen when Mn$^{2+}$ concentration was increased beyond 100 μM. Unlike MtMetAP1c, MtMetAP1a showed optimal activity at 10 μM of Co$^{2+}$, and 0.1-1 mM of Mn$^{2+}$.

Example 2: Identification of MtMetAP Inhibitors Via High-Throughput Screening

In collaboration with ASDI Inc., a structurally diverse small molecule library of 175,000 compounds was screened against MtMetAP1c at final concentration of 30 μM in 384-well plates using the coupled enzymatic assay (Zhou, Y., et al. *Anal. Biochem.* 280:159-165). A total of 439 hits were identified that exhibited greater than 40% inhibition of MtMetAP1c at a final concentration of 10 μM. A number of the hits were found to contain 2, 3-dichloro-1,4-naphthoquinone core structure. A total of 28 structural analogs were acquired for structure activity relationship studies (Table 2). For MtMetAP1a, it was found that any substitution at positions 2 or 3, other than halogens reduced activity of the naphthoquinone. In contrast, MtMetAP1c tolerated both mono- or di-p-fluorophenyl and dibromo substitutions (compound 21, 22 and 20 respectively) (Table 2). In addition, we also determined the effects of some naturally occurring 1,4-naphthoquinones including Vitamin K derivatives (Table 2) against both MtMetAP1a and MtMetAP1c. None of them were active against either MtMetAP enzymes. Among all analogs we obtained and tested, 2,3-dibromo-1,4-naphthoquinone (compound 20) was found to be the most potent against both MtMetAP1a and MtMetAP1c with IC$_{50}$ values of around 1 μM (Table 2).

TABLE 2

Effect of Naphthoquinones on MtMetAPs

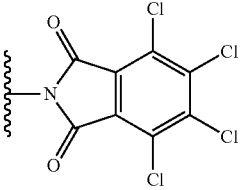 [SMILES: *N1C(=O)c2c(Cl)c(Cl)c(Cl)c(Cl)c2C1=O]

| ID | R1 | R2 | R3 | IC50 (μM) MtMetAP1a | IC50 (μM) MtMetAP1c |
|---|---|---|---|---|---|
| 2 | 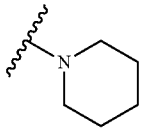 [SMILES: *N1CCCCC1] | Cl | H | 4.0 ± 0.3 | 8.7 ± 0.2 |
| 3 | (piperidinyl-N) | Cl | H | 8.0 ± 1.3 | 17.2 ± 1.8 |
| 4 | Cl | Cl | H | 3.3 ± 0.3 | 6.6 ± 1.2 |
| 5 | NH$_2$ | Cl | H | >100 | >100 |

TABLE 2-continued

Effect of Naphthoquinones on MtMetAPs

| | | | | IC50 (μM) | |
|---|---|---|---|---|---|
| ID | R1 | R2 | R3 | MtMetAP1a | MtMetAP1c |
| 6 | NH—C₆H₄—Cl (4-chlorobenzylamino) | Cl | H | >100 | >100 |
| 7 | 4-methylpiperazin-1-yl | Cl | H | >100 | >100 |
| 8 | 4-(3-chlorophenyl)piperazin-1-yl | Cl | H | >100 | >100 |
| 9 | 4-(3,4-dichlorophenyl)piperazin-1-yl | Cl | H | >100 | >100 |
| 10 | 4-(5-chloro-2-methylphenyl)piperazin-1-yl | Cl | H | >100 | >100 |
| 12 | NH-(3-trifluoromethylphenyl) | Cl | H | >30 | >50 |
| 13 | NH-(3-fluorophenyl) | Cl | H | >30 | >50 |

TABLE 2-continued
Effect of Naphthoquinones on MtMetAPs
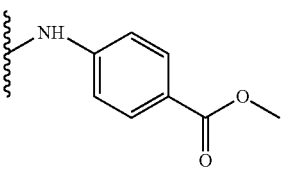 [SMILES: *Nc1ccc(C(=O)OC)cc1]
| | | | | IC50 (μM) | |
|---|---|---|---|---|---|
| ID | R1 | R2 | R3 | MtMetAP1a | MtMetAP1c |
| 14 | 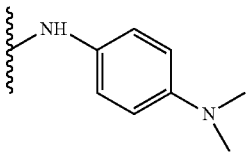 [SMILES: *Nc1ccc(N(C)C)cc1] | Cl | H | >30 | >50 |
| 15 | 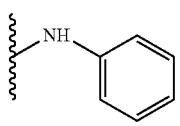 [SMILES: *Nc1ccccc1] | Cl | H | >30 | >50 |
| 16 | 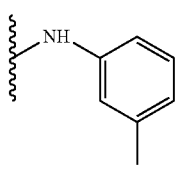 [SMILES: *Nc1cccc(C)c1] | Cl | H | >50 | >50 |
| 17 | 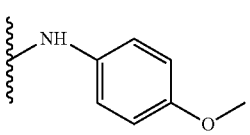 [SMILES: *Nc1ccc(OC)cc1] | Cl | H | 18.6 ± 6.1 | 21.3 ± 10.6 |
| 18 | 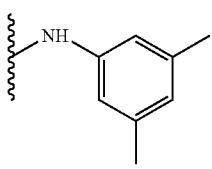 [SMILES: *Nc1cc(C)cc(C)c1] | Cl | H | 15.9 ± 0.6 | 22.5 ± 1.5 |
| 19 | 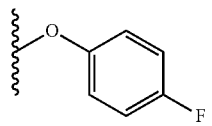 [SMILES: *Oc1ccc(F)cc1] | Cl | H | 13.9 ± 1.0 | 16.4 ± 6.8 |
| 20 | Br | Br | H | 1.14 ± 0.25 | 0.71 ± 0.02 |
| 21 | 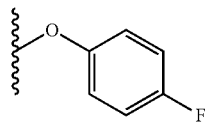 | 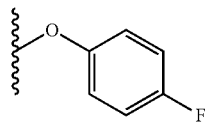 | H | 4.93 ± 0.20 | 1.79 ± 0.49 |
| 22 | 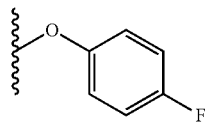 | Cl | H | 7.58 ± 0.28 | 3.74 ± 0.52 |

TABLE 2-continued

Effect of Naphthoquinones on MtMetAPs

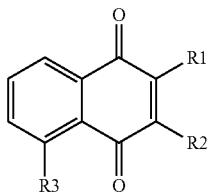

| ID | R1 | R2 | R3 | IC50 (µM) MtMetAP1a | IC50 (µM) MtMetAP1c |
|---|---|---|---|---|---|
| 23 | H | H | OH | >50 | >30 |
| 24 | CH$_3$ | H | OH | >50 | >50 |
| 25 | OH | H | H | >50 | >50 |
| 26 | ~N(propyl)(propyl) | Cl | H | >50 | >30 |
| 27 | NH-C(O)-3,5-bis(CF$_3$)phenyl | Cl | H | >50 | >50 |
| 28 | phytyl chain | CH$_3$ | H | >50 | >50 |
| 29 | CH$_3$ | H | H | >50 | >50 |

Figure 5:
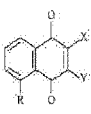
FIG. 5. Effect of Naphthoquinones on MtMetAPs.

Additional compounds and biological data, including IC$_{50}$ (µM) in assays with MtMetAP1a and MtMetAP1c, can be found in FIGS. 5, 6, and 7. The dibromonaphthoquinone (8, FIG. 5) is still the most potent MtMetAP inhibitor among the expanded collection of naphthoquinones. The halo naphthoquinones 7 and 34 did not exhibit good selectivity in inhibiting MtMetAPs where they also were found to inhibit HsMetAP2 with even better avidity (0.91 and 2.31 µM for 7 and 34 respectively). However, one derivative 19, does better in discriminating against orthologous MetAPs. The anilino-naphthoquinone 19 lacks the desired pontency against MtMetAPs, but it should serve as a starting point for inhibitor design in this class of compounds.

The most potent MtMetAP inhibitors we have found to date belong to the naphthothiazole class (FIG. 6). Amidoxime 48 had been identified as a lead-like hit in the primary screen of ASDI library. A systematic SAR study was conducted on this class of compounds. All of the permutations done to amidoxime moiety (compounds 37 through 46, see FIG. 6) resulted in completely inactive compounds, suggesting perhaps, that the amidoxime group is an indispensable pharmacophore in this class. With the thiazolylamidoxime moiety fixed as being optimal, we then turned our attention onto the A-ring (compounds 47 through 52). Amidoxime 48 carries a methoxy group at position 7 on the A-ring, and we eventually discovered that the presence of a methoxy group on the A-ring slightly decreases the potency against MtMetAP1a without affecting the activity against MtMetAP1c that much (48 through 52 versus 47). The only position for methoxy group that was somewhat detrimental to the activity was position 8 on the A-ring (compound 49, two times less potent against MtMetAP1c when compared to 48). Besides that, a methoxy group can be placed on position 7 or 6 (48 and 50), two methoxy groups may be attached to 7 and 8 positions simultaneously (51), or even positions 7 and 8 may be tied with methylenedioxy group (52) without sacrificing the potency. Our final SAR exploration was devoted to altering the B-ring (53 to 59). Ring contraction giving rise to a 5-membered ring (56) or totally eliminating the B-ring (59) turned out to be a huge disaster for the inhibition capacity of these amidoximes. The B-ring can be a 6-membered ring, and may even contain an oxygen atom in the ring (53 and 54), however, if a substituent like a phenyl group were placed on the B-ring it would lose all the activity against MtMetAPs (amidoxime 55). Turning the B-ring into a 7-membered ring produced very potent TB MetAP inhibitors (57 and 58). In both 6- and 7-membered ring cases going from a carbocyclic B-ring to an oxacycle gave rise to highly enhanced potency (that is 48→53 and 57→58). Gratifyingly, with a methodical SAR investigation we arrived at benzoxepinothiazole 58, a pretty potent inhibitor of MtMetAP1a (760 nM) and MtMetAP1c (60 nM)

which is an improvement of 48 and 7 fold respectively for the two MtMetAPs over the lead-like hit 48 that we commenced with.

In our high-throughput screening efforts to identify inhibitors of MetAPs from *M. tuberculosis*, we serendipitously discovered 7-bromo-5-chloroquinolin-8-ol (69 in FIG. 7), a congener of clioquinol as a novel inhibitor of MetAPs. Clioquinol is a compound in the hydroxyquinoline class that was used to treat traveler's diarrhea and is now studied in phase II clinical trials for use in treatments for Alzheimer's disease (Raman, et al. 2005, *J. Biol. Chem.* 280: 16157-62). We characterized the effects of clioquinol and three of its analogs (60, 66, 69 and 70) on MtMetAPs. All the four compounds inhibited both the enzymes at low micromolar range, with quinolinol 69 being the most potent. In addition, all the compounds tested in the hydroxyquinoline class displayed specificity for cobalt loaded MtMetAP1c compared to manganese loaded MtMetAP1c Next, the effects of the most potent inhibitors on the growth of *M. tuberculosis* in culture were determined. Compounds 4 and 20 were found to be most potent against *M. tuberculosis* with MIC values of 10.0 and 10.0-25 µg/mL, respectively (Table 3). Interestingly, the other analogs which had slightly higher $IC_{50}$ values for either MtMetAP1c (compounds 2 and, from Table 2) or MtMetAP1a (compound 21 and 22) showed about a two-fold increase in MIC values (Table 3). In addition to replicating *M. tuberculosis*, we also tested these MtMetAP inhibitors in aged-cultured *M. tuberculosis* (Table 3). Interestingly, the active inhibitors, compounds 4 and 20, were equally effective against the aged-cultured form of *M. tuberculosis* as the replicating form.

TABLE 3

Minimum Inhibitory Concentration (MIC) of MtMetAP inhibitors on *M. tuberculosis* M.I.C. (µg/mL)

| Compound-ID | *M. tuberculosis* | Aged-cultured *M. tuberculosis* |
|---|---|---|
| 2 | 25 | 23.8 |
| 3 | >25 | >27.6 |
| 4 | 10 | 5.7-11.4 |
| 20 | 10.0-25 | ND |
| 21 | >25 | ND |
| 22 | >25 | ND |

Example 3: Overexpression of MtMetAP1a or MtMetAP1c Confers Resistance to *M. tuberculosis* to the Newly Identified MetAP Inhibitors If MtMetAP is the in vivo target of the inhibitors, it is expected that their overexpression will cause resistance. In order to perturb the cellular levels of MtMetAPs, we first cloned each of the mycobacterial MetAP1s into pSCW35ΔsigF (FIG. 3), a vector whose promoter is regulated by acetamide ($P_{ace}$). This vector also has an attP site that allows for stable integration of a single copy of the plasmid into the attB site in the chromosome of *M. tuberculosis* (Raghunand, T. R., W. R. Bishai, and P. Chen. 2006. *Int. J. Antimicrob. Agents* 28:36-41). The entire ORFs of MtMetAP1a and MtMetAP1c genes were amplified by PCR in the sense orientation from *M. tuberculosis* strain CDC1551 genomic DNA and were then subcloned into pSCW35ΔsigF vector. The pSCW35-(MtMetAP1a) and pSCW35-(MtMetAP1c) clones were verified by DNA sequencing.

To overexpress MtMetAP1a and MtMetAP1c in *M. tuberculosis*, knock-in strains for both MtMetAPs were constructed by transforming *M. tuberculosis* CDC1551 with pSCW35ΔsigF-(MtMetAP1a) and pSCW35ΔsigF-(MtMetAP1c), respectively. In addition, we also transformed *M. tuberculosis* with a control empty plasmid, pSCW35ΔsigF. All three transformants were grown until early logarithmic phase and expression was induced by addition of 0.2% acetamide followed by incubation for an additional 24 hrs. To confirm that the levels of both MtMetAP1s were increased, real-time quantitative PCR was used to quantitate the transcript levels of both enzymes. The mRNA levels of MtMetAP1a and MtMetAP1c were about 4.5- and 6-fold higher than that of the control (FIG. 3B). We examined the growth of the knock-in *M. tuberculosis* strains in the presence of 2,3-dichloro-1,4-naphthoquinone. Both the wild-type and control *M. tuberculosis* strains were inhibited in the presence of 10 µg/mL 2,3-dichloro-1,4-naphthoquinone (FIG. 4). In contrast, both MtMetAP1a and MtMetAP1c knock-in strains gained resistance to the inhibitor (FIG. 4), suggesting that both MtMetAP1a and MtMetAP1c are capable of binding and sequestering the inhibitor in vivo.

Knockdown of MtMetAP1a and MtMetAP1c in *M. tuberculosis*.

It has been shown that MetAP plays an essential role in bacteria, as knockout in *Escherichia coli* and other bacteria is lethal (Chang, S. Y., et al. 1989. *J. Bacteriol.* 171:4071-4072; Miller, C. G., et al. 1989. *J. Bacteriol.* 171:5215-5217). Since *M. tuberculosis* possesses two MetAP genes, it was unclear whether knocking out either or both of these genes in *M. tuberculosis* is sufficient to cause lethality. In order to study the requirement of MtMetAP1a and MtMetAP1c for viability of *M. tuberculosis*, we cloned each of the mycobacterial MetAP1s in the reverse orientation downstream of the acetamide regulated promoter ($P_{ace}$) in pSCW35ΔsigF (FIG. 3Aiii). The resulting plasmids, pSCW35ΔsigF-(α-MtMetAP1a) and pSCW35ΔsigF-(α-MtMetAP1c), were verified by DNA sequencing. These anti-sense vectors, as well as the empty control vector were used to transform *M. tuberculosis*. The three transformants were grown till early log phase at which point the antisense RNA was induced by addition of 0.2% acetamide followed by incubation for 24 hrs. Then the cultures were grown for three weeks on plates in the presence and absence of acetamide. To confirm that the levels of both mycobacterial MetAP1s were altered, we employed real-time quantitative PCR to quantitate the transcript levels of both enzymes. The mRNA levels of MtMetAP1a and MtMetAP1c were reduced by about 1.7- and 2.3-fold in comparison to that of the control (FIG. 3C). The colony counts after three weeks (Table 4) showed that knock-down of MtMetAP1c in *M. tuberculosis* had a marginal effect on bacterial growth in comparison to the control, indicating that MtMetAP1c is probably a non-essential gene. However, knockdown of MtMetAP1a decreased the viability by 76.0% in *M. tuberculosis* (Table 4). These results suggested that MtMetAP1a is likely an essential gene in *M. tuberculosis*, while MtMetAP1c may not be required for viability.

TABLE 4

Viability of Knock-down strains of MtMetAP1s in *M. tuberculosis*.

| *M. tuberculosis* Knock-down Construct | Viability (%) |
|---|---|
| pSCW35-(_-MtMetAP1a) | 76.0 ± 4.0 |
| pSCW35-(_-MtMetAP1c) | 95.3 ± 4.7 |
| pSCW35_ sigF | 94.6 ± 4.4 |

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

Those skilled in the art will recognize, or be able to ascertain using no more than routine experimentation, many equivalents of the specific embodiments of the invention described herein. Such equivalents are intended to be encompassed by the following claims.

What is claimed is:

1. A method of treating a disease or disorder associated with a bacterial infection in a subject, the method comprising the step of administering to the subject an effective amount of a compound of formula II-A:

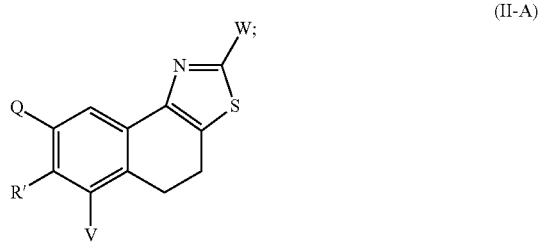

(II-A)

or a pharmaceutically acceptable salt thereof, wherein,

W is $NR_DC(O)R_D$, $N=C(R_E)$alkyl, $N=C(R_E)$aryl, $N=C(R_E)$heteroaryl, $N=C(R_E)$aralkyl, or $NR_DCR_B=N-OH$;

R' is H or $OR_B$;

Q is H or $OR_B$; or

R' and Q, together with the atoms to which each is attached, forms a heterocycloalkyl, which is optionally substituted;

V is H or $OR_B$;

each $R_B$ is independently H, optionally substituted alkyl, optionally substituted aralkyl, optionally substituted heteroaralkyl, or optionally substituted aryl;

each $R_D$ is independently H, optionally substituted alkyl, optionally substituted aralkyl, optionally substituted heteroaralkyl, or optionally substituted aryl; and each $R_E$ is independently H, optionally substituted alkyl, optionally substituted aralkyl, optionally substituted heteroaralkyl, or optionally substituted aryl.

2. The method of claim 1, wherein the bacterial infection is a Mycobacterial infection.

3. The method of claim 2, wherein the type of Mycobacterial infection is a *M. tuberculosis* infection.

4. The method of claim 1, wherein the step of administering the compound comprises administering the compound in a dosage of between about 0.1 and 120 mg/kg/day.

5. The method of claim 1, wherein the step of administering the compound comprises administering the compound in a dosage of less than about 500 mg/day.

* * * * *